US011226392B1

(12) United States Patent
Castagnoli et al.

(10) Patent No.: US 11,226,392 B1
(45) Date of Patent: Jan. 18, 2022

(54) ESTIMATING USER RISK BASED ON WIRELESS LOCATION DETERMINATION

(71) Applicant: Juniper Networks, Inc., Sunnyvale, CA (US)

(72) Inventors: Neal Dante Castagnoli, Las Vegas, NV (US); Mohammad Zohoorian, San Francisco, CA (US)

(73) Assignee: Juniper Networks, Inc., Sunnyvale, CA (US)

(*) Notice: Subject to any disclaimer, the term of this patent is extended or adjusted under 35 U.S.C. 154(b) by 0 days.

(21) Appl. No.: 16/999,422

(22) Filed: Aug. 21, 2020

(51) Int. Cl.
| | |
|---|---|
| G01S 5/02 | (2010.01) |
| G01S 5/14 | (2006.01) |
| G16H 50/80 | (2018.01) |
| G08B 21/02 | (2006.01) |
| G16H 50/30 | (2018.01) |
| G16H 70/60 | (2018.01) |
| H04W 4/02 | (2018.01) |

(52) U.S. Cl.
CPC .......... *G01S 5/0289* (2013.01); *G01S 5/0278* (2013.01); *G01S 5/14* (2013.01); *G08B 21/02* (2013.01); *G16H 50/30* (2018.01); *G16H 50/80* (2018.01); *G16H 70/60* (2018.01); *H04W 4/023* (2013.01)

(58) Field of Classification Search
None
See application file for complete search history.

(56) References Cited

U.S. PATENT DOCUMENTS

| | | | | |
|---|---|---|---|---|
| 10,198,779 | B2* | 2/2019 | Pittman | H04W 4/02 |
| 10,803,993 | B2* | 10/2020 | Huang | G16H 50/30 |
| 2013/0275160 | A1 | 10/2013 | Lev et al. | |
| 2013/0318027 | A1* | 11/2013 | Almogy | G16H 50/20 |
| | | | | 706/52 |
| 2019/0239029 | A1* | 8/2019 | Hostyn | H04W 4/023 |

OTHER PUBLICATIONS

Extended Search Report from counterpart European Application No. 20207482.9, dated May 3, 2021, 12 pp.

* cited by examiner

*Primary Examiner* — Thomas S McCormack
(74) *Attorney, Agent, or Firm* — Shumaker & Sieffert, P.A.

(57) ABSTRACT

Disclosed are embodiments for estimating risk associated with a user of a wireless device. In some embodiments, the risk relates to a risk of infection by a contagious disease. For example, in some embodiments, the contagious disease is Coronavirus 2019. In some embodiments, locations of multiple wireless devices are estimated based on signal strengths of signals associated with the devices. Neighboring devices are identified based on highest probability regions of the devices that are determined based on associated signals. A measure of proximity to other devices is then determined based on probabilities that each device is located in neighboring regions. The risk is then based on the measure of proximity. In some embodiments, a risk of a first user associated with a first wireless device is based, in part, on a risk of a second user within a proximity of the first user.

20 Claims, 28 Drawing Sheets

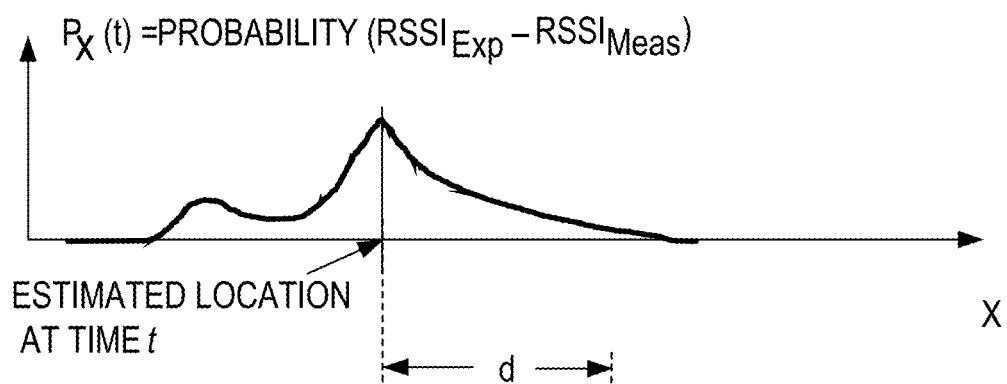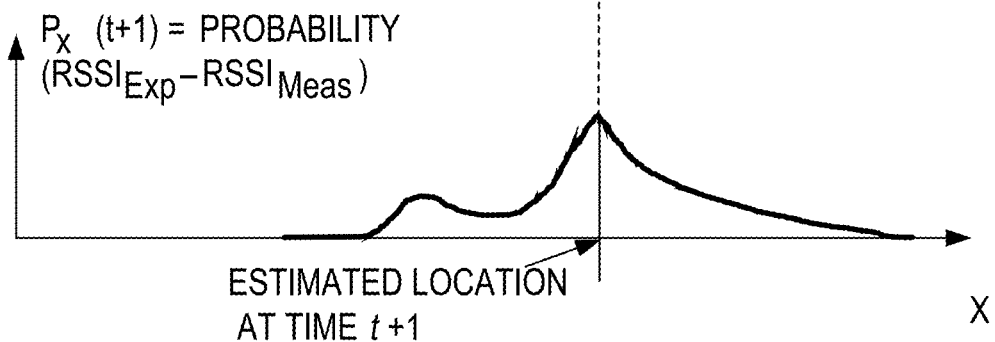
FIG. 7

ESTIMATING USER RISK BASED ON WIRELESS LOCATION DETERMINATION

FIELD

The present application relates to wireless communications and, more particularly, to methods and/or apparatus for estimating risk of exposure of a user of a wireless device to an infectious disease.

BACKGROUND

Wireless devices have become essential to how people live. As such, people generally carry their wireless devices as they move around and travel. There are a variety of techniques which can be used to identify an individual's location based on a location of their associated wireless device. The recent Coronavirus pandemic has increased attention on the importance of maintaining a social distance between individuals, so as to reduce the spread of the infectious disease. The location determining capabilities associated with wireless devices promise to assist with managing social distance.

BRIEF DESCRIPTION OF THE FIGURES

FIG. 7 illustrates an example shift in a location probability curve resulting from projected motion of a wireless terminal.

DETAILED DESCRIPTION

Figure 1:
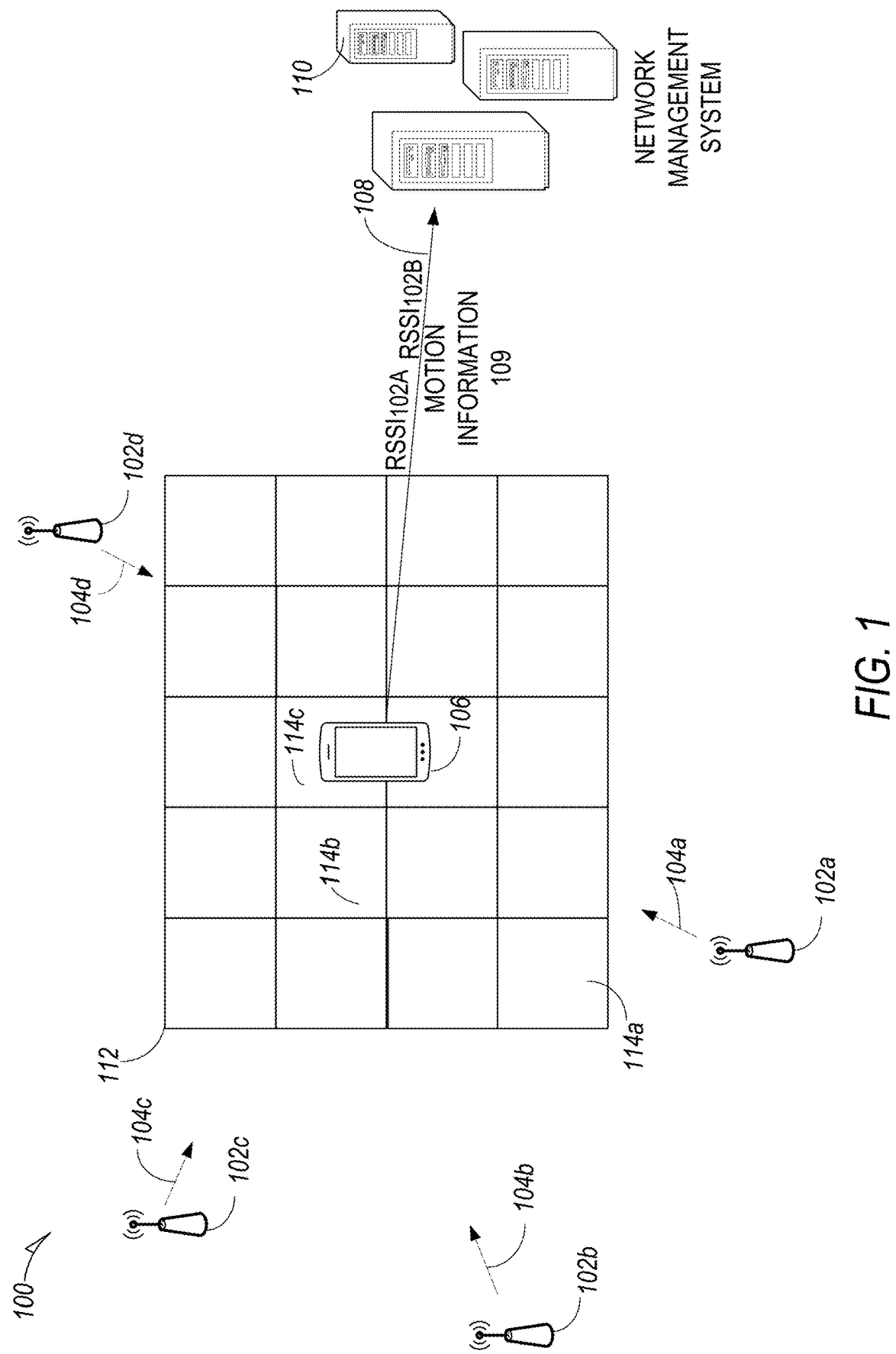
FIG. 1 is an overview diagram of a system that is implemented in one or more of the disclosed embodiments.

Example embodiments determine a probability that two or more wireless devices, or alternatively users associated with these wireless devices, were within a predefined proximity of each other for at least a predefined duration of time. To manage a contagious disease such as the Covid-19, information relating to a proximity of individuals is helpful. Transmission of diseases such as viruses or bacteria frequently depends on a distance between two individuals, which provides an opportunity to expose an uninfected individual to the contagion, and a time duration of the exposure. With respect to Covid-19, the centers for disease control (CDC) has determined that if a first individual is closer than six feet from a second individual who is infected, the first individual is recommended to enter quarantine for two weeks or until tested and found not to be sick.

Some disclosed embodiments determine proximity between individuals via wireless signals, e.g., Wi-Fi, Bluetooth, etc. The wireless signals are used to estimate locations of devices associated with the individuals. Some embodiments estimate location based on strengths of wireless signals received from known locations (e.g. access points at known locations). Some embodiments then estimate a distance to the known locations based on the signal strengths, and then apply traditional triangulation based approaches to the distances to determine a location. Other embodiments measure a phase offset between a signal received at two antennas of a wireless device to estimate a wireless device location, as discussed further below.

Once locations of each of the individual wireless devices are determined, a proximity between any two devices is calculated based on the estimated locations of these devices. Use of location estimates based on RSSI can be problematic, as the location determines are subject to noise included in RSSI measurements. Similar problems exist for location estimates based on phase differences of signals received at a plurality of antennas. The disclosed embodiments solve this problem by delivering a more accurate proximity estimation. This improved accuracy is based, at least in part, on an aggregation of probabilities associated with multiple possible device locations. aggregating multiple probabilities of multiple location determinations. In addition, any noise associated with signaling used to determine the location is mitigated by aggregating probabilities across multiple devices proximate to the first wireless device when estimating a risk associated with the first wireless device.

Unlike transitional systems that determine a location of a wireless terminal using triangulation-based methods (e.g., averaging the areas defined by the intersections of the distances Dist), at least some of the disclosed embodiments rely on location probability surfaces (LPSs) to determine an estimated location.

An LPS represents a plurality of probabilities that a wireless terminal is located within a corresponding plurality of geographic regions. This plurality of geographic regions can be represented in a data structure, such as a two dimensional array, as a grid. In some embodiments, the grid in total may represent a two-dimensional geographic area of 50×50 meters and each cell in the grid or region is 0.5×0.5 meters for example. Other grid and cell/region sizes are within the scope of the disclosed embodiments. In some embodiments, each of the plurality of geographic regions is a two dimensional geographic area. In other embodiments, the plurality of geographic regions are each three-dimensional geographic volumes. Thus, in some embodiments, a location probability surface represents a probability that the WT is located in each of a plurality of different geographic volumes of, for example, 50×50×50 meters, with each volume or region of the plurality of regions representing an area of, 0.5×0.5×0.5 meters in this example. Other region sizes are contemplated and within the scope of the disclosed embodiments.

To generate an LPS, the disclosed embodiments receive a signal strength measurement from a wireless terminal. This signal strength measurement is referred to as $SS_{Meas}$ in the discussion below. The signal strength measurement is of a signal generated and transmitted by a wireless transmitter and received by the wireless terminal. In some embodiments, a received signal strength indication (RSSI) represents the signal strength measurement.

From the signal strength measurement, the disclosed embodiments determine the plurality of probabilities that the wireless terminal is located within each of the corresponding plurality of geographic regions.

A general equation describing behavior of radio signals is as follows:

$$SS_i = PLE * \log(Dist_i) + Int + Dir_i \qquad \text{Eq. 1}$$

where:
$SS_i$ a signal strength of an $i^{th}$ wireless transmitter as experienced (and measured) by the wireless terminal,
PLE a path loss exponent; (e.g. −20 db for line of sight loss; <−20 db for those environments with attenuation, such as the signal being transmitted through translucent objects),
$Dist_i$ distance between the wireless terminal and an $i^{th}$ transmitter,
Int an intercept function of the power of the transmitter,
$Dir_i$ a directional adjustment reflecting a gain of antennas in a direction along a path between the $i^{th}$ transmitter and wireless terminal.

As part of a determination of probabilities in a location probability surface, the disclosed embodiments determine an expected signal strength of each of the plurality of regions. An expected signal strength for a region is based on one or more of a transmit power of the wireless transmitter, and a distance between the wireless transmitter and the respective region. Thus, these embodiments determine each of the respective expected signal strength measurements based on a respective distance between the respective region and the wireless transmitter as described in Equation 1 above. The distance between the respective region and wireless transmitter is determined, in some embodiments, based on known locations of both the respective region and the wireless transmitter. For example, some embodiments receive configuration information that defines locations of known wireless transmitters. Additionally, these embodiments receive configuration input defining locations of the plurality of regions. In some embodiments, locations of the plurality of regions is inferred based on locations of the known wireless transmitters (e.g. a geographic area between the known wireless transmitters is divided into the plurality of regions).

Signal strength measurements by a wireless terminal are affected by noise. Under some circumstances, the measured signal strengths contain approximately six (6) db of noise (SD=6 db). Thus, one difference between $SS_{Meas}$ and $SS_{Exp}$ is attributable to the noise. There are one or more additional factors, including multipath, a gain of the receiver, and other parameters associated with a model of the channel. Gaussian noise can contribute to the difference between $SS_{Exp}$ and $SS_{meas}$.

Some of the disclosed embodiments then determine a difference between the measured and expected signal strengths based Equation 2 below:

$$SS_{Error} = SS_{Exp} - SS_{Meas} \qquad \text{Eq. 2}$$

where:
$SS_{Error}$ difference between expected and measured signal strengths,
$SS_{Exp}$ an expected signal strength value as calculated, is some embodiments, via Equation 1, and
$SS_{meas}$ a measured signal strength values (as measured by the wireless terminal).

As a noise level can be empirically measured to be ~six (6) db, a probability curve of $SS_{Error}$ is assumed to be Gaussian with Sigma=6 in some embodiments. Other curves may be used in other embodiments. For each dimension of the $SS_{Error}$ and for each cell the Probability(i, x, y) is determined where i is the index of the ith dimension corresponding to the $i^{th}$ measured signal strength received from the $i^{th}$ radio transmitter, and x & y are the consistent coordinates of a specific cell in the grid.

Thus, to generate a location probability surface, an expected signal strength of a signal in each of a plurality of regions is determined. In at least some embodiments, this determination is based on at least a location of a wireless transmitter generating the signal. corresponding differences between the expected signal strength of a region and the measured signal strength are also determined. Probabilities that the wireless terminal is located in each of the regions is then determined based on the corresponding differences.

Some of the disclosed embodiments determine multiple location probability surfaces, one surface for each wireless transmitter received and measured by the wireless terminal. To support this, the wireless terminal performs a plurality of signal strength measurements (one for each wireless transmitter). These signal strength measurements are transmitted, in some embodiments, by the wireless terminal to a network management system for further processing. The signal strength measurements are used to determine signal strength errors for each cell. The signal strength error is then used to determine a probability that the mobile device is located in each specific cell. These probability surfaces are referred to throughout this disclosure as $P_i$ ($SS_{Exp} - SS_{Meas}$) where the index i represent an $i^{th}$ dimension of a signal strength measurement upon which the probability surface is derived.

Some wireless terminal embodiments determine signal strength measurements periodically, iteratively, continuously, or upon command from a user. These measurements are then transmitted to a network management system. For each dimension of the measured signal strength and for each cell in the grid, the system calculates the probability that the wireless terminal is in the specific cell based on the value of the specific dimension of the $SS_{Error}$ value.

To determine the probability that a wireless terminal is within a particular region or cell of the grid, some embodiments multiply corresponding probability values from multiple location probability surfaces. Corresponding values in this context are values representing probability values within an equivalent region or grid cell. One or more of the disclosed embodiments implement this approach via Equation 3 below:

$$P_{x,y} = P1,x,y * P2,x,y * \ldots * P_{n-1,x,y} * P_{n,x,y} \qquad \text{Eq. 3}$$

where:
$P_{x,y}$ Probability that the wireless terminal is in a cell associated with the x, y, coordinates,
P1,x,y—Probability that the wireless terminal is in the x, y cell based on the first dimension of $SS_{Error}$,
P2,x,y Probability that the wireless terminal is in the x, y cell based on the second dimension of $SS_{Error}$,
$P_{n-1,x,y}$ Probability that the wireless terminal is in the x, y cell based on the $(n-1)^{th}$ dimension of $SS_{Error}$,
$P_{n,x,y}$ Probability that the wireless terminal is in the x, y cell based on the $n^{th}$ dimension of $SS_{Error}$,
*—Multiplication operator As the probabilities of each location probability surface are independent, peak or maximum probabilities within each location probability surface may vary. Consequently, a cell-wise multiplication of n surfaces yields a new probability surface which may have multiple peaks and valleys. This new probability surface is referred to in this disclosure as a composite location probability surface. Some embodiments determine an estimated location of the wireless terminal based on the composite location probability surface. For example, in some embodiments, a region corresponding to a highest probability in the composite location probability surface is used as an estimated location of the wireless terminal. In other embodiments, a weighted value for each region or cell of the composite location probability surface is used to estimate the location of the wireless terminal. For example, in some aspects, weighted values along a first dimension or a second dimension may be determined for each cell or region (e.g. regions higher associated probability may be more heavily weighted than regions with lower associated probability).

The explanation above treats each region or cell of a location probability surface and/or the composite location probability surface as a singular point for which an expected signal strength at the center of the region is evaluated. Other embodiments may perform this calculation in the continuous domain. In this case the probability of the wireless terminal being in a specific region (e.g. cell x,y) is calculated for each dimension of the $i^{th}$ received signal by $$P_{x,y,i} = \int \int_{x,y} P_{x,y}(SS_{Exp} - SS_{Meas}) dxdy \qquad \text{Eq. 4}$$

In some embodiments, the location probability surface(s) and/or composite location probability surface are calculated periodically, (e.g., once per second) based on updated signal strength measurements performed by the wireless terminal and reported to a network management server.

Some of the disclosed embodiments generate a predicted location probability surface for a future time, e.g. T+1, based on information available at a previous time, e.g. time T. The predicted location probability surface for time T+1 is then utilized to generate a blended location probability surface for time T+1. The blended location probability surface at time T+1 is also generated based on a composite location probability surface for time T+1.

The predicted location probability surface is generated based on motion estimates for the wireless terminal. The motion estimates are based, in part, based on accelerometer and/or gyro information received from the wireless terminal itself. The motion estimates are also based, at least in some embodiments, on previous blended location probability surfaces of the wireless terminal. Thus, for example, a motion estimate at time T+2 is based, in some embodiments, on one or more of a blended location probability surface at times T=0 and/or T=1.

Each of the motion estimates of the wireless terminal is associated with a probability that the respective motion estimate is accurate for the wireless terminal. A combination of the motion estimates and their associated probabilities can be organized, in some embodiments, into a motion probability surface. Each cell of the surface represents a set of motion parameters for the wireless terminal, and a probability that those parameters accurately represent the motion of the wireless terminal.

In some embodiments, motion estimates are generated based on motion information received from the wireless terminal. Information received from the wireless terminal can include accelerations in each of an x, y, and z dimension. An accuracy associated with each of the acceleration measurements is also obtained from the wireless terminal in some embodiments. In other embodiments, the accuracy information is configured or hard coded at a network management system performing these calculations. The acceleration measurements provided by the wireless terminal are applied to a distribution (e.g. Gaussian) in order to generate a plurality of different motion estimates (and their associated probabilities), any one of which can reflect the true motion of the wireless terminal at an applicable time. For example, a motion estimation and its associated probability takes the form, in at least some embodiments, of [Vx, Vy, Vz, Prob] where Vx is speed in an X direction, Vy is speed in a Y direction, Vz is speed in a Z direction, and Prob is a probability that the wireless terminal exhibits the motion described by [Vx, Vy, Vz]. In some embodiments, only two dimensions of motion are estimated. In these embodiments, the motion estimate and its associated probability takes the form, in at least some embodiments, of [Vx, Vy, Prob].

An example equation demonstrating generation of a motion probability surface is provided by Equation 5 below. Equation 5 is used in at least some of the disclosed embodiments:

$$P_m(t) = (P_{blended}(t-3) \oplus_{ab} P_{blended}(t-2) \oplus_{ab}$$
$$P_{blended}(t-1)) \oplus_{acc} WT_{acc} \qquad \text{Eq. 5}$$

where:
$P_m(t)$ motion probability surface at time t,
$P_{blended}(t)$ blended location probability surface at time t,
$WT_{acc}$ velocity or acceleration information from wireless terminal (e.g. Vx, Vy, Vz, or $A_x$, $A_y$, $A_z$),
$\oplus_{ab}$ an aggregating blended location probability surface operator. In some embodiments, the aggregating blended location probability surface operator averages probabilities in corresponding regions or cells of two blended location probability surfaces,
$\oplus_{acc}$ an operator that applies motion information from the wireless terminal ($WT_{acc}$) to an aggregated blended location probability surface (produced via $\oplus_{ab}$). FIG. 13B below describes one embodiment of $\oplus_{acc}$.

Note that in some embodiments, multiple prior blended location probability surfaces are used when generating a motion probability surface. For example, additional surfaces $P_{blended}(t-2)$, $P_{blended}(t-3)$, and/or $P_{blended}\text{-x}(t-4)$ may be utilized to generate $P_m(t+1)$.

Figure 3:
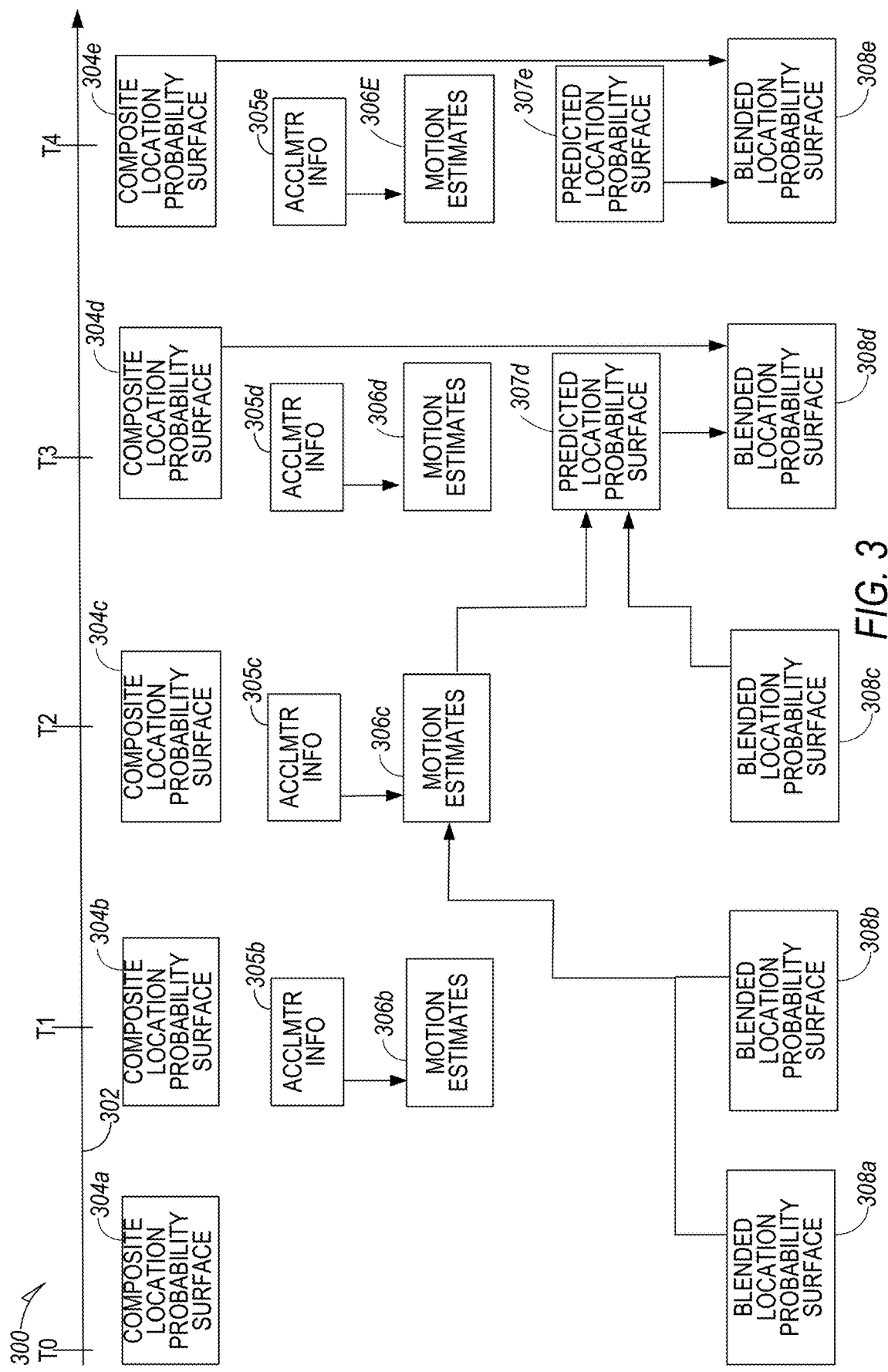
FIG. 3 is a diagram of data flow that is implemented in one or more of the disclosed embodiments.
Figure 14:
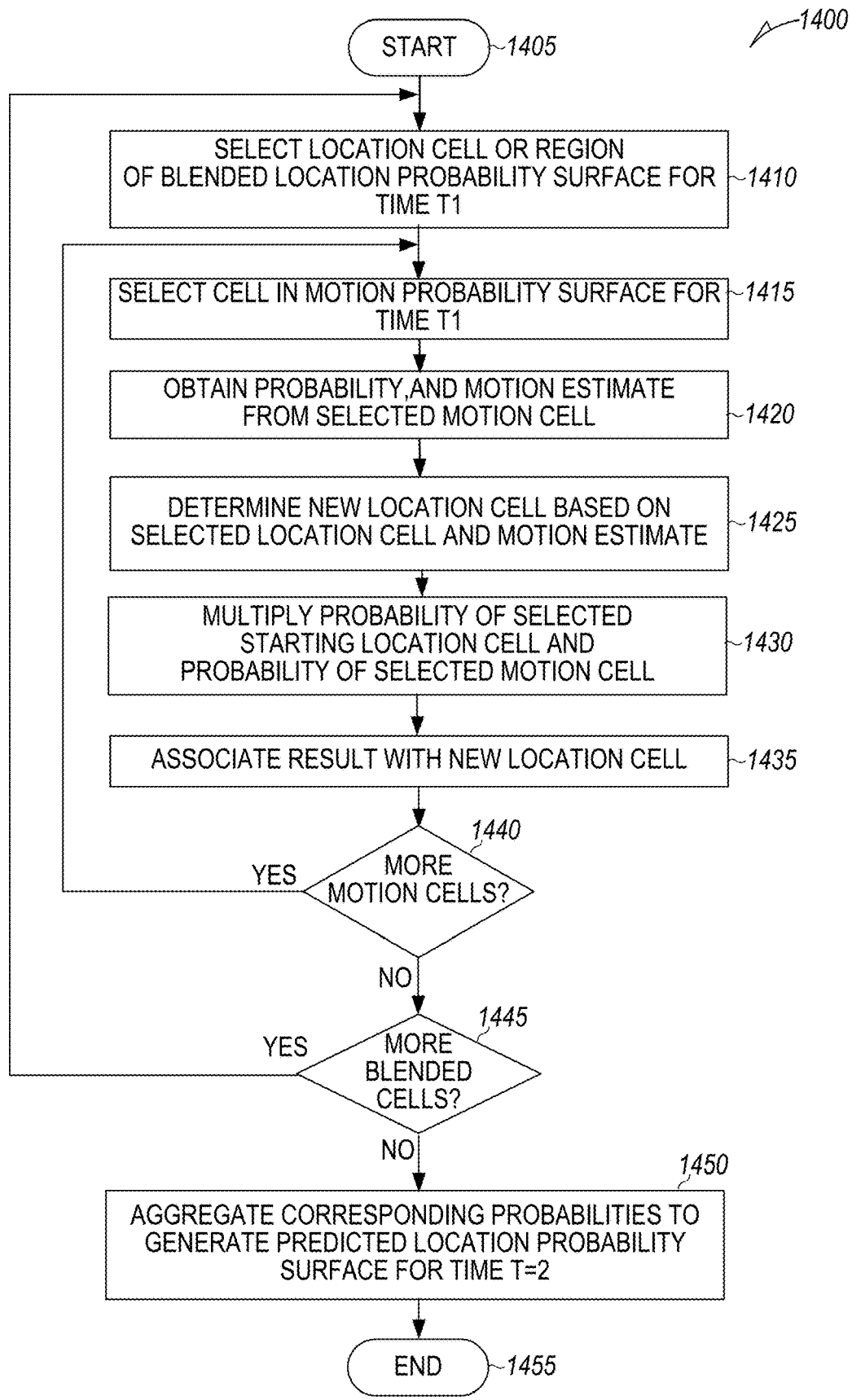
FIG. 14 is a flowchart of a method for applying a motion probability surface to a composite location probability surface.

Some estimates apply the plurality of motion estimates (e.g. a motion probability surface) to one or more prior blended location probability surfaces to generate a predicted location probability surface. An example for generating a predicted location probability surface is given by Equation 6 below:

$$P_{predicted}(t+1) = P_{blended}(t) \oplus {}_m P_m(t) \qquad \text{Eq. 6}$$

where:

$P_{predicted}(t+1)$ predicted location probability surface of wireless terminal at time t+1, $P_{blended}(t)$ blended location probability surface at time t, $\oplus_m$ motion operator. FIG. 14 below describes one embodiment of $\oplus_m$, and $P_m(t)$ motion probability surface at time t Operation of Equation 6 is illustrated in FIG. 3 discussed below. In some embodiments, a blended location probability surface at time t is based on the predicted location probability surface at time t and a composite location probability surface at time t. This is shown via Equation 7 below:

$$P_{blended}(t) = P_{predicted}(t) \oplus {}_b P_{composite}(t) \qquad \text{Eq. 7}$$

where:

$P_{blended}(t)$ is a blended location probability surface at time t, $P_{predicted}(t)$ is a predicted location probability surface at time t, and $P_{composite}(t)$ is a composite location probability surface at time t, and $\oplus_b$ is a blended operator for combining the predicted and composite location probability surfaces. In one example embodiment, $\oplus_b$ averages corresponding probabilities in a predicted location probability surface and a composite location probability surface.

In some embodiments, the blended location probability surface at time t is generated via a weighted sum of a predicted location probability surface and a composite location probability surface at time t. This is illustrated by Equation 8 below:

$$P_{blended}(t) = \alpha * P_{composite}(t) + \beta * P_{predicted}(t) \qquad \text{Eq. 8}$$

where:

$P_{blended}(t)$ blended location probability at time t, $P_{composite}(t)$ composite location probability surface at time t, $P_{predicted}(t)$ predicted location probability surface for time t, $\alpha$ and $\beta$ parameters e.g., $\alpha+\beta=1$. In some embodiments, each of $\alpha$ and $\beta$ have a value of 0.5.

Some embodiments use a blended location probability surface at time t+1 and a motion probability surface at time t+1 to estimate a predicated location probability surface of the device at time t+2. Some of the disclosed embodiments iteratively calculate new composite location probability surfaces, motion estimates, predicted location probability surfaces, and blended location probability surfaces, and iteratively estimate locations of a mobile terminal based on these iteratively determined data structures.

In some embodiments, a location of the device is determined to be in a region having the largest probability. One embodiment of such an approach is represented by Equation 9 below:

$$\{x,y\}(t) = \text{Max}(P_{Blended}(t)) \qquad \text{Eq. 9}$$

where:

$\{x, y\}$ (t) estimated location of the device at time t, $P_{blended}(t)$—blended location probability surface at time t, and $\text{Max}(P_{Blended}(t))$ Max function returns identification (e.g. x, y coordinates) of largest probability in $P_{Blended}(t)$.

Some embodiments rank regions according to their associated probabilities. A highest ranked set of these regions (e.g. k regions) are then selected. The location is then based on the k highest ranked regions (and not on regions ranked below the $k^{th}$ highest ranked region). One embodiment of this approach is represented mathematically by Equation 10 below:

$$x, y \text{ (location)} = \sum_{i=1}^{k} (x_i, y_i) * P(x_i, y_i) \bigg/ \sum_{i=1}^{k} (P(x_i, y_i)) \qquad \text{Eq. 10}$$

where:

x,y (location)—estimated location based on a blended location probability surface, k a limit on a number of probability maximums considered when determining the estimated location, $(x_i, y_i)$ x, y coordinate of the $i^{th}$ ranked peak, and $P(x_i, y_i)$ a probability of the wireless terminal being at location $x_i, y_i$.

FIG. 1 is an overview diagram of a system 100 that is implemented in one or more of the disclosed embodiments. The system 100 includes four access points 102a-d. Each of the four access points 102a-d generates corresponding signals 104a-d. Signal 104a, signal 104b, signal 104c, and signal 104d are received by a wireless terminal 106. The wireless terminal 106 measures a strength of each of the signals 104a-d and generates a message 108 indicating the signal strengths. For example, FIG. 1 shows the message 108 indicating a received signal strength indication (RSSI) for a signal from access point 102a and a second RSSI value for a signal from access point 102b. RSSI is just one example of a signal strength measurement and other embodiments use different measurements for signal strength.

The wireless terminal 106 transmits the message 108 to a network management system 110. The network management system 110 utilizes the signal strength measurements included in the message 108 to estimate a position or geographic location of the wireless terminal 106. In some embodiments, the network management system 110 divides a geographic area 112 into a plurality of regions. Region 114a, region 114b, and region 114c are illustrated in FIG. 1, while other regions within the geographic area 112 are not labeled to preserve figure clarity. In some of the disclosed embodiments, the network management system 110 calculates a probability that the wireless terminal 106 is located in each of the plurality of regions (including the regions 114a-c). These probabilities are based on the signals 104a-d received by the wireless terminal 106. In particular, the probabilities are based on strengths of the signals 104a-d as measured by the wireless terminal. In some embodiments, the access points 102a-d are at known locations. Thus, a distance between each access point 102a-d and each region (e.g. 114a-c) can be determined by the network management system. From these distances, the network management system 110 determines an expected signal strength of a signal received from each of the access points 102a-d at each of the regions (e.g. 114a-c). By comparing the expected received signal strength to the signal strength measured by the wireless terminal, the network management system can determine a probability that the wireless terminal is in the region.

In some embodiments, these probabilities are refined via additional probabilities of the wireless terminal's location that are based on motion information for the wireless terminal. For example, in some embodiments, the wireless terminal provides motion information 109 to the network management system in the message 108. In other embodiments, a different message is used to provide motion information 109 from the wireless terminal 106 to the network management system 110. The wireless terminal 106 derives the motion information from, in some embodiments, an accelerometer that is integrated into the wireless terminal 106.

In some embodiments, motion of the wireless terminal 106 is inferred by the network management system 110 via changes in sequential determinations of the wireless terminals location, as explained further below.

Figure 2:
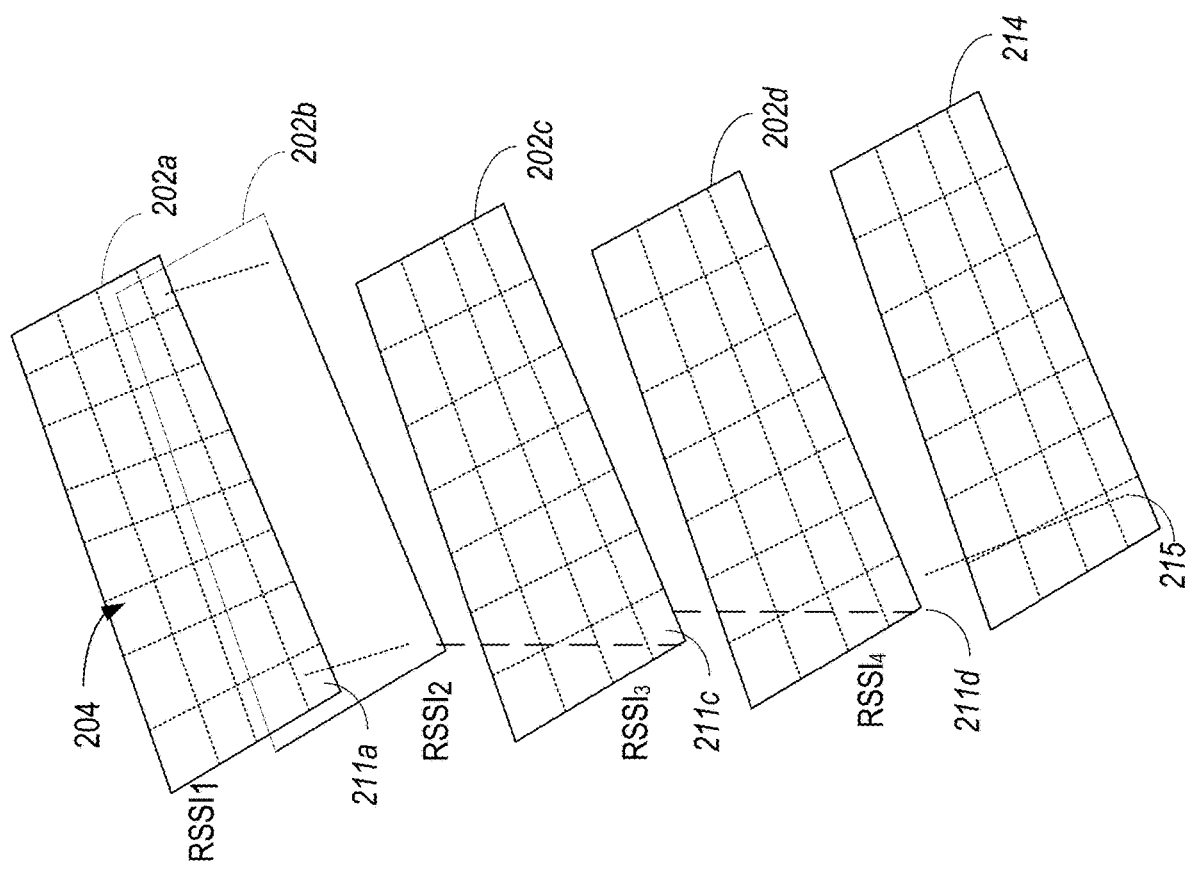
FIG. 2 shows aggregation of a plurality of location probability surfaces.

FIG. 2 shows aggregation of a plurality of location probability surfaces. As discussed above with respect to FIG. 1, the network management system 110 determines a plurality of probabilities that the wireless terminal 106 is within a corresponding plurality of regions (e.g. regions 114a-c). FIG. 2 shows a plurality of location probability surfaces 202a-d Each of the location probability surfaces 202a-d is generated based on signals from different wireless transmitters. For example, in one embodiment, each of the location probably surfaces 202a-d is generated based on signals from access points 102a-d respectively. Each of the location probability surfaces 202a-d includes a plurality of probabilities. This plurality of probabilities is illustrated in FIG. 2 via the grid like structure of the location probability surface 202a, labeled as grid 204. The probabilities included in each of the location probability surfaces 202a-d are not graphically illustrated, so the location probability surfaces appear flat for simplicity of illustration.

Each cell of the grid 204 represents a different probability included in the location probability surface. Each probability corresponds to a region, such as the regions 114a-c discussed above with respect to FIG. 1. In other words, each probability indicates a likelihood that the wireless terminal 106 is located within a region corresponding to the cell containing the probability. In at least some of the disclosed embodiments, a plurality of location probability surfaces (e.g. 202a-d) are generated. Each location probability surface is generated based on one or more single signal strength measurements by the wireless terminal 106 of a signal (e.g. any of 104a-d) from a single wireless transmitter (e.g. any one of AP 102a, AP 102b, AP 102c, or AP 102d). Thus, each of location probability surfaces 202a and 202b and 202c of FIG. 2 are generated based on signal strength measurements of different signals generated by different wireless transmitters.

FIG. 2 shows that the plurality of location probability surfaces 202a-d are aggregated to generate a composite location probability surface 214. Each cell of the composite location probability surface 214 (e.g. cell 215) has corresponding cells in each of the location probability surfaces (e.g. cell 211d for location probability surface 202d, cell 211c for location probability surface 202c, and cell 211a for location probability surface 202a). For figure clarity, a corresponding cell is not labeled for location probability surface 202b. These cells correspond because they each represent equivalent regions or locations. Aggregating corresponding probabilities in multiple location probability surfaces includes multiplying the probabilities in at least some embodiments. Thus, aggregating two or more location probability surfaces, for example, includes aggregating, for each of the plurality of regions represented by the two location probability surfaces, first and second probabilities corresponding to respective regions represented by the two or more location probability surfaces. A location estimate of the wireless terminal is then based, in at least some embodiments, on the aggregated first and second probabilities. The location estimate is based on more than just first and second probabilities in some embodiments, for example, those embodiments aggregating more than two location probability surfaces.

FIG. 3 is a diagram of data flow in a processing pipeline that is implemented in one or more of the disclosed embodiments. The processing pipeline is shown operating on several types of data at each of five time references T0-T5, shown on a time axis 302. An elapsed time between each of the time references T0-T5 is equivalent. An amount of elapsed time between each of the time references can vary by embodiment. Some embodiments generate a new set of data (e.g. composite location probability surface, motion probability surface, predicted location probability surface, and blended location probability surface) every one second, five seconds, ten seconds, 30 seconds, one minute or any elapsed time period. Various embodiments obtain new accelerometer measurements from the wireless terminal (discussed further below) at a different interval or an equivalent interval.

While each type of data shown is generated at each time reference T0-T4 in some embodiments, some data is omitted from the figure for clarity. FIG. 3 shows data flow 300 including composite location probability surfaces 304a-e, accelerometer information 305b-e, motion probability surfaces 306b-e, predicted location probability surfaces 307d-e, and blended location probability surfaces 308a-e.

In some embodiments, any of the composite location probability surfaces 304a-e are analogous to the composite location probability surface 214 discussed above with respect to FIG. 2. FIG. 3 also shows motion probability surfaces 306b-e. (Another motion probability surface which would be labeled 306a is omitted from the figure for clarity). Each of the accelerometer information 305b-e results from motion information provided by a wireless terminal, a location of which is being estimated by the data flow 300 shown in FIG. 3. At each time period T0-T4, FIG. 3 shows that the wireless terminal has provided corresponding motion information, e.g., acceleration information, represented by each of accelerometer information 305b-e.

Each of the motion probability surfaces 306b-e is generated based on motion information received from the mobile device, represented as the accelerometer information 305b-e. For example, the accelerometer information 305b-e indicates, in at least some embodiments, velocities in each of an X, Y, and Z directions. In accordance with other embodiments the accelerometer information 305b-e represents acceleration in the X, Y, and Z directions. The motion probability surfaces 306b-e are also generated, in at least some embodiments, based on one or more blended location probability surfaces from prior time periods. For example, FIG. 3 shows that motion probability surface 306c is generated based on at least the blended location probability surface 308a and 308b (see for example, Equation 5 above). The motion probability surface 306d is generated based on one or more of blended location probability surfaces 308a, 308b, and 308c. Lines indicated a dependency of motion probability surface 306d on any of the blended location probability surface 308a, 308b, or 308c are omitted from FIG. 3 to preserve clarity of the figure.

Each of the motion probability surfaces 306b-d are then used, in at least some embodiments, to generate a respective predicted location probability surface, such as the predicted location probability surface 307d shown in FIG. 3 (generated via motion probability surface 306c as shown) (see also Equation 6 above). The predicted location probability surface 307d is then used, along with the composite location probability surface 304d (which is based on signal strength measurements corresponding to time T3), to generate the blended location probability surface 308d (See also Equation 7 discussed above). While arrows illustrate a particular data flow used to generate blended location probability surface 308d in at least some embodiments, the reader should recognize that similar data flows would be employed to generate each of the blended location probability surface 308a-e. However, arrows illustrating all of these data flows are omitted for clarity.

Thus, FIG. 3 describes how some embodiments progressively or iteratively generate a first composite location probability surface 304a, second composite location probability surface 304b, third composite location probability surface 304c, and then a fourth composite location probability surface 304d. Each of these composite location probability surfaces is associated with a particular time reference, represented as times T0-T4 in FIG. 3. A plurality of motion probability estimates of the wireless terminal are also generated at each time reference. In FIG. 3, this information is represented as motion probability surfaces 306b-e. In some embodiments, the motion estimates are represented as a motion probability surface. In other embodiments, the motion estimates are represented via structures other than a motion probability surface. A blended location probability surface is then used, along with the motion probability surface to generate a predicted location probability surface for a subsequent time period When the subsequent time period arrives, the predicted location probability surface for the subsequent time period, and a composite location probability surface for that time period are then used to generate a blended location probability surface for that time period.

Note that FIG. 3 and the discussion above describe operation of the data flow 300 when it has reached a fully initialized or steady state mode of operation. One of skill would understand that when any one or more of the disclosed embodiments is first initialized, a data pipeline for multiple time periods, such as T0-T4 is not necessarily available. Therefore, some of the operations discussed above are not performed if the data is not available. For example, a first blended location probability surface generated by the disclosed embodiments is not based on prior blended location probability surfaces, since that data is not available. Similarly, when a first blended location probability surface is generated, a predicted location probability surface is not available, as predicted location probability surfaces are generally created for a future time reference. Thus, when a very first blended location probability surface is generated, it may simply be a copy of the corresponding composite location probability surface (e.g. blended location probability surface 308a generated based on composite location probability surface 304a, without use of a predicted location probability surface, at least in some embodiments.

Figure 4:
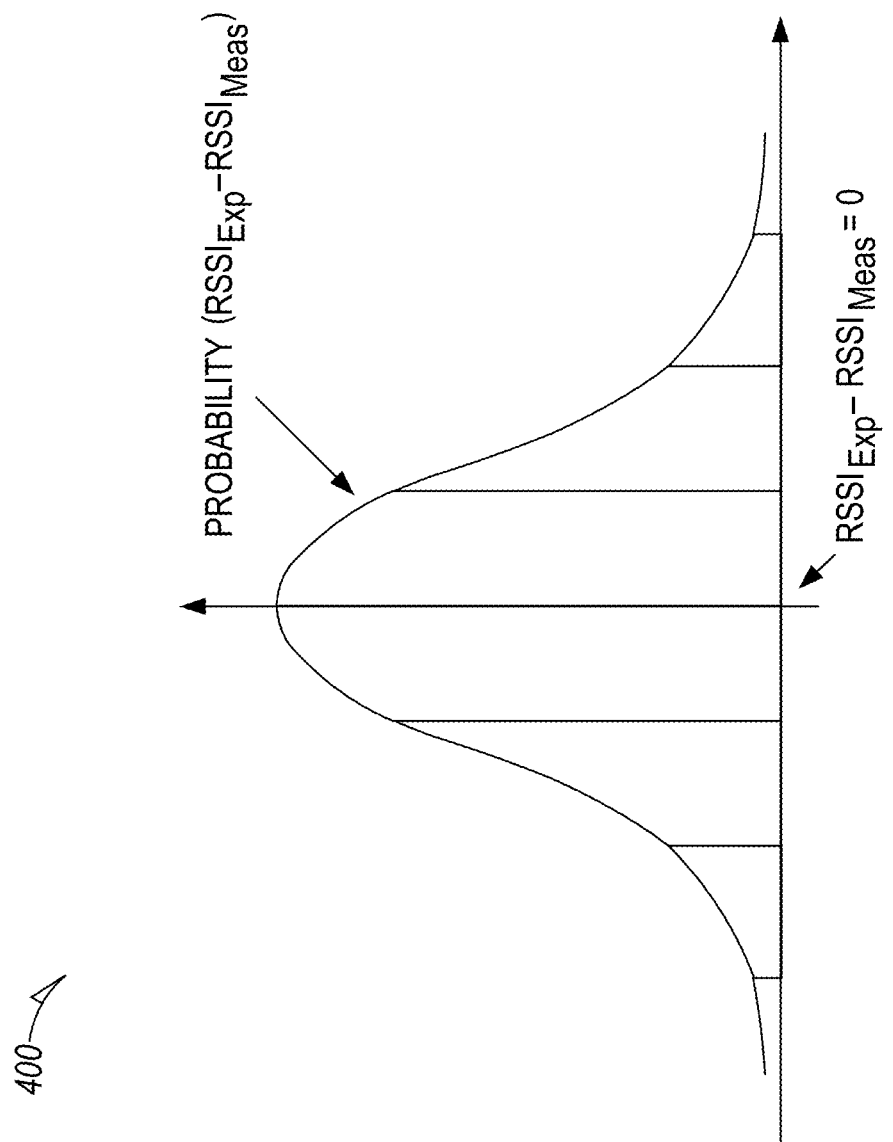
FIG. 4 is an example probability curve of a single dimension of a signal strength error.

FIG. 4 is a graph 400 of an example probability curve of a single dimension of an example $P(SS_{Error})$. A Gaussian probability curve is illustrated but other embodiments may provide for alternative probability distributions.

Figure 5:
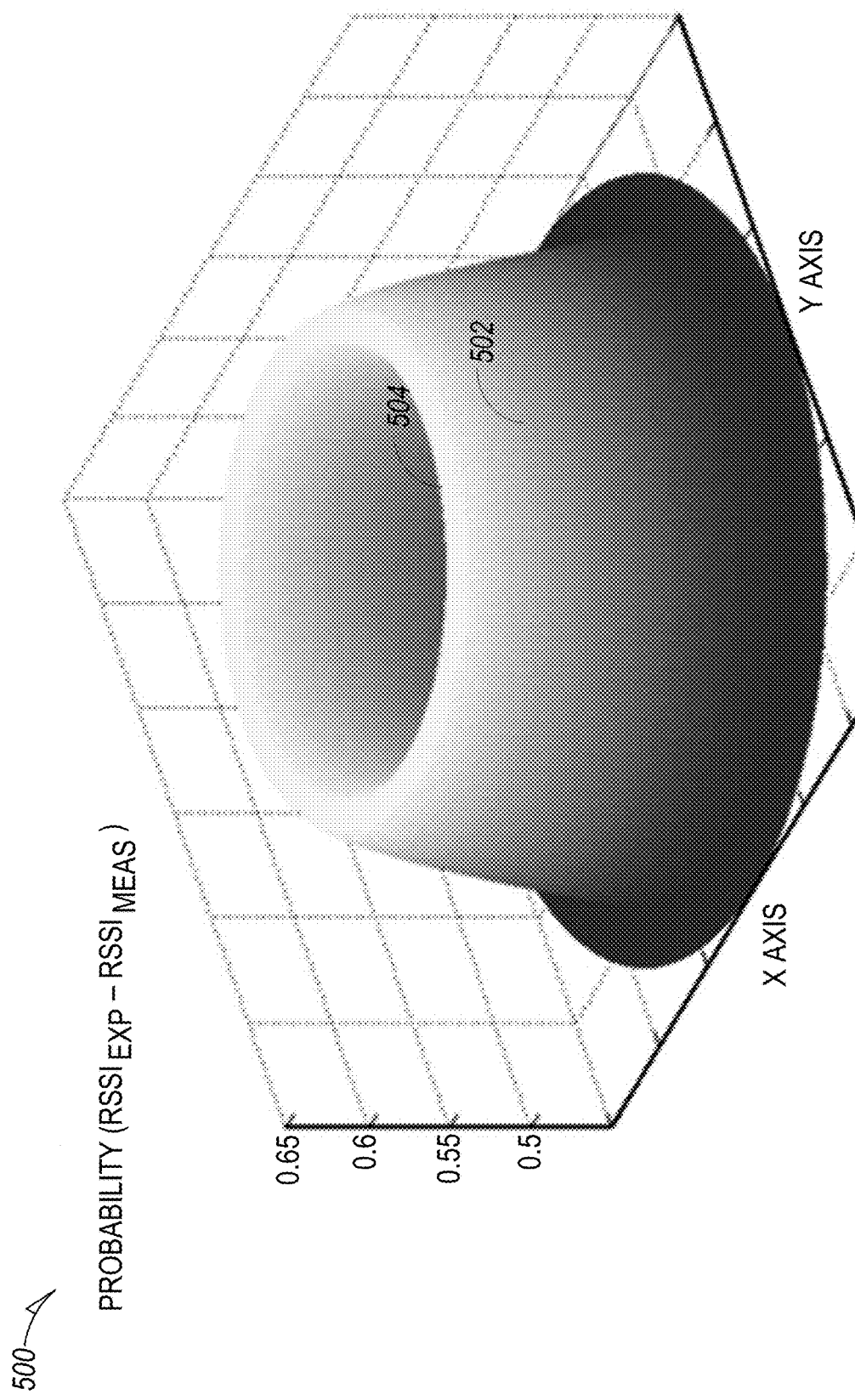
FIG. 5 is a graphical representation of probabilities of an example two-dimensional location probability surface.

FIG. 5 is a graphical representation 500 of probabilities of an example two-dimensional location probability surface. The probabilities 502 exhibit a donut shape. The donut shape illustrates a ring 504 of relatively high probability locations for a subject device, with surrounding regions exhibiting lower probabilities.

Figure 6:
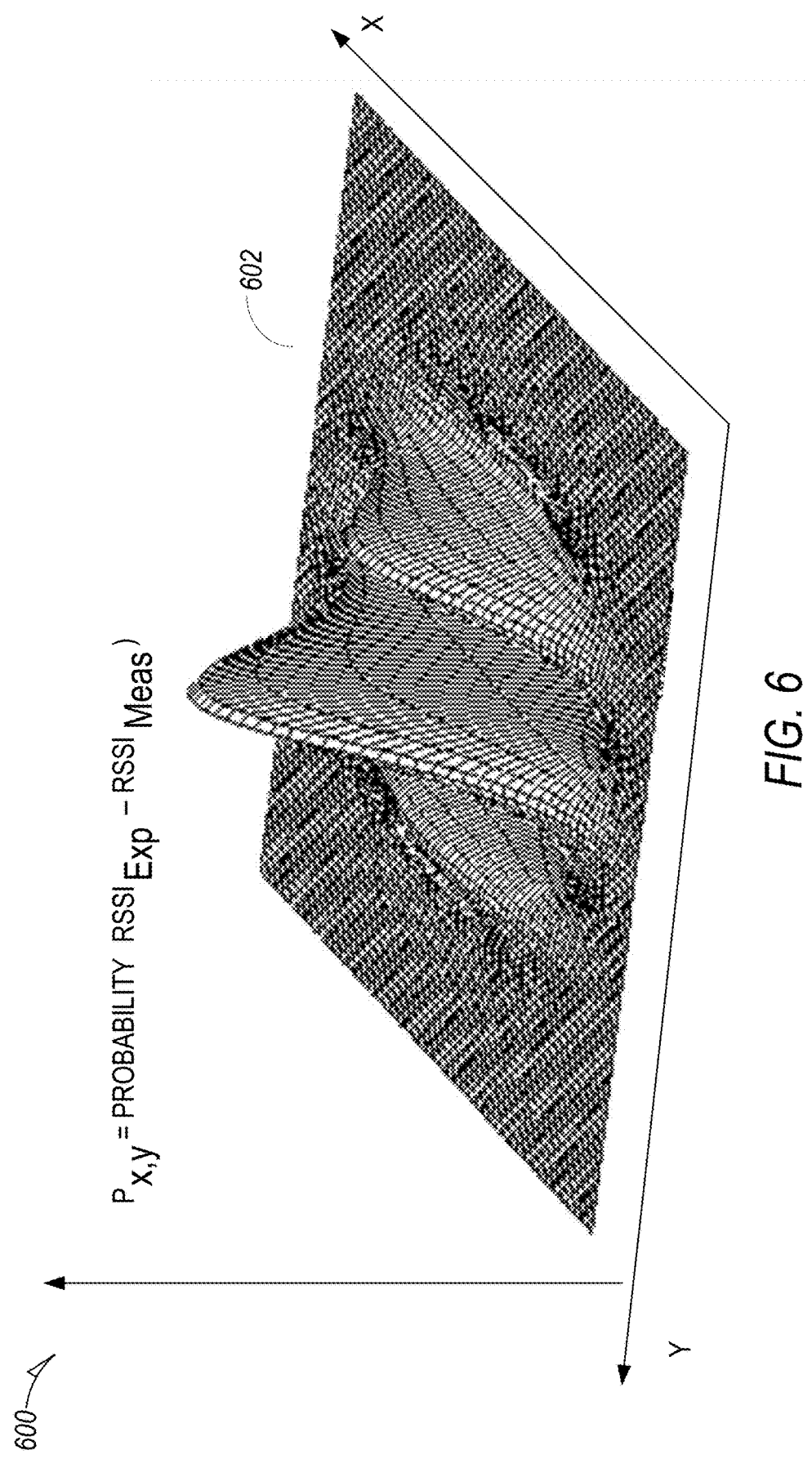
FIG. 6 is a graphical representation of a composite location probability surface.

FIG. 6 is a graphical representation 600 of an example location probability surface. As explained above, location probability surface 602 is generated based on a difference between expected received signal strength values and measured received signal strength values for a plurality of regions.

FIG. 7 illustrates a one dimensional location probability curve of a device at times t and t+1. The first graph 700a and a second graph 700b demonstrate an example shift in a location probability curve resulting from motion of a wireless terminal at a deterministic speed of d meters per second. Since some embodiments estimate speed as a deterministic number (d meters per second) a shape of a derived location probability curve at time t+1 is the same as the shape of a location probability curve at time t. Since the device is moving at a speed of d meters/sec, the location at time t+1 is given by L(t+1)=L(t)+1*d, and the probability of the device of being at any given location P(L(t+1)) is the same probability curve P(L(t)) shifted by d to the right. This is also explained above with reference to Equation 6.

Figure 8:
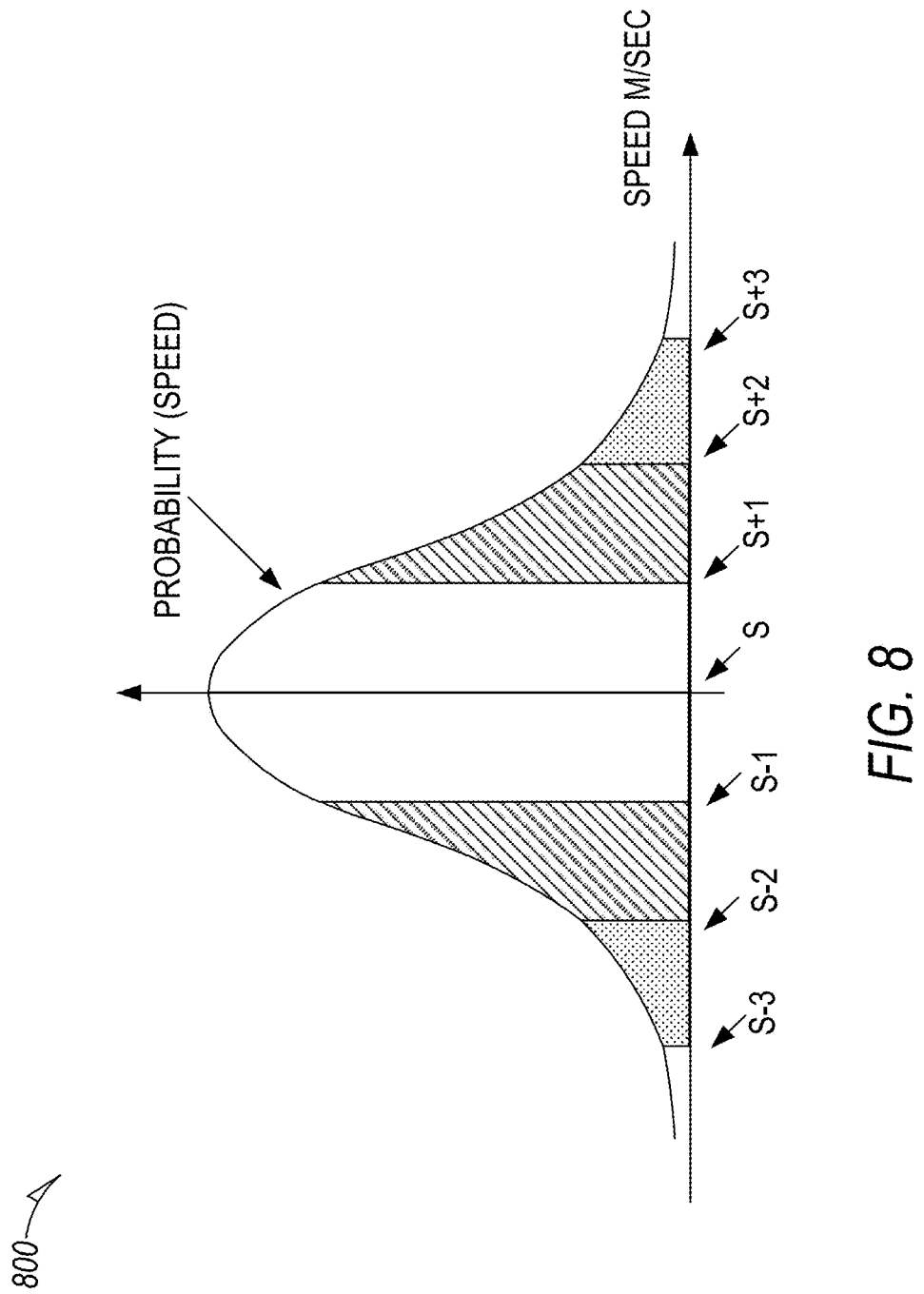
FIG. 8 illustrate a simplified speed probability in a single direction.

FIG. 8 is a graph 800 illustrating a simplified speed probability in a single direction. The curve illustrates a mean speed of s meters per second, with the highest probability. However, the device may be travelling at either higher or lower speed than s meters per second at lower probabilities. Using a motion probability curve to estimate a predicted location probability surface of a device at time t+1 based on a blended location probability surface at time t results in a predicted location probability surface at time t+1 which looks different than a location probability surface at time t or the blended location probability surface at time t.

Figure 9:
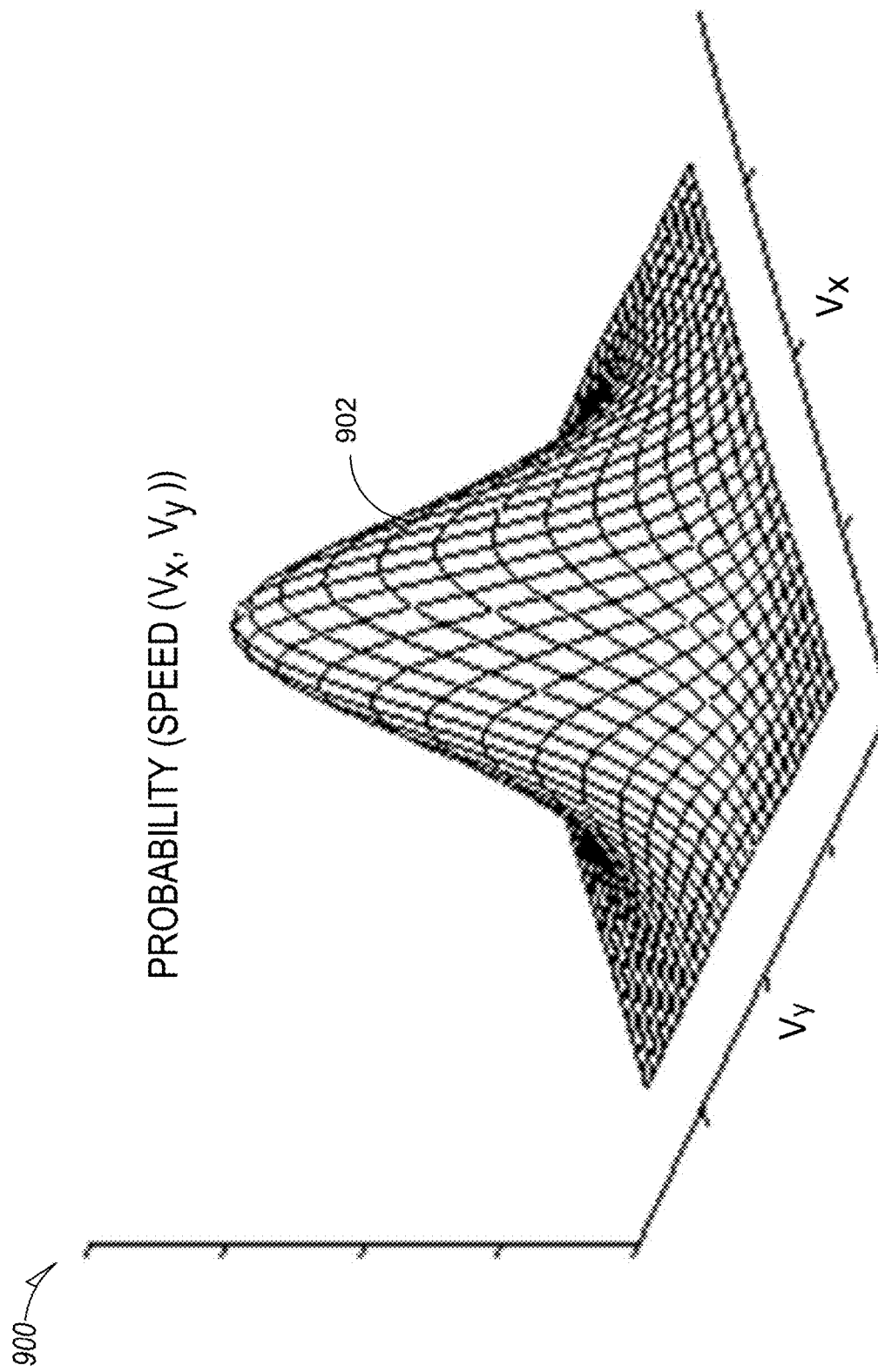
FIG. 9 illustrates a two-dimensional motion (Vx, & Vy) probability surface.

FIG. 9 is a graph 900 illustrating an example two-dimensional motion probability surface 902. In some embodiments, each cell of the motion probability surface indicates a velocity and direction, for example, via a Vx, and Vy values. In some other embodiments, motion probability is calculated for a three-dimensional space, e.g., for Vx, Vy, and Vz.

Returning to the example of a two-dimensional motion probability surface, each cell of a motion probability surface also indicates a probability that the wireless terminal exhibits motion consistent with the motion estimates indicated by the cell. FIG. 9 shows a simplified two-dimensional representation of a motion probability surface, since it is difficult to clearly show a three-dimensional surface in a written document. A height of the motion probability surface 902 indicates a probability that the wireless terminal will exhibit the motion parameter values (e.g. $V_x$, $V_y$) corresponding to the cell.

Figure 10:
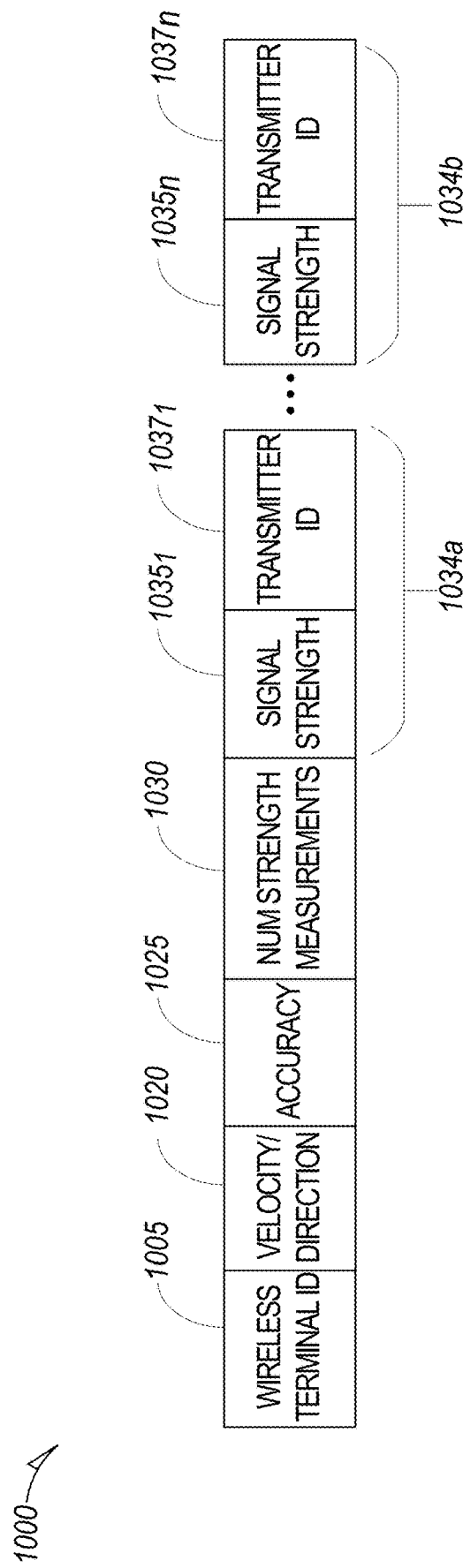
FIG. 10 shows an example message portion that is implemented in one or more of the disclosed embodiments.

FIG. 10 shows an example message portion that is implemented in one or more of the disclosed embodiments. The message portion is transmitted, in some embodiments, by a wireless terminal (e.g. 106) to a network management system (e.g. 110). The message portion 1000 includes a wireless terminal identifier field 1005, velocity/direction field 1020, an accuracy field 1025, and a number of signal strength measurements field 1030. A variable number of field pairs such as field pair 1034a and field pair 1034b follow the number of signal strength measurements field 1030. Each field pair includes a signal strength field, e.g.

$1035_1 \ldots 1035_n$ and a transmitter id field e.g. transmitter id field $1037_1 \ldots$ transmitter id field $1037_n$.

The wireless terminal identifier field 1005 uniquely identifies a wireless terminal (e.g. 106) (e.g. via a station address of the wireless terminal). The velocity/direction field 1020 indicates a velocity and direction (e.g. $V_x$, $V_y$, $V_z$) of the wireless terminal identified via the wireless terminal identifier field 1005. The accuracy field 1025 indicates a variability or accuracy of the velocity/direction information included in the field 1020. In some embodiments, a wireless terminal is configured with parameters that define the accuracy field 1025. In some embodiments, the wireless terminal obtains the accuracy information stored by the accuracy field 1025 via hard coded values, for example, values hard coded and obtained from a built in accelerometer. In some embodiments, the accuracy field 1025 indicates value used to generate a probability distribution of motion values, as discussed herein with respect to a motion probability surface and, for example, FIG. 15 below.

Alternatively, the velocity/direction field provides an indication of the acceleration along the X, Y, and Z which the mobile device obtains from its internal accelerometers such as gyros.

Figure 11:
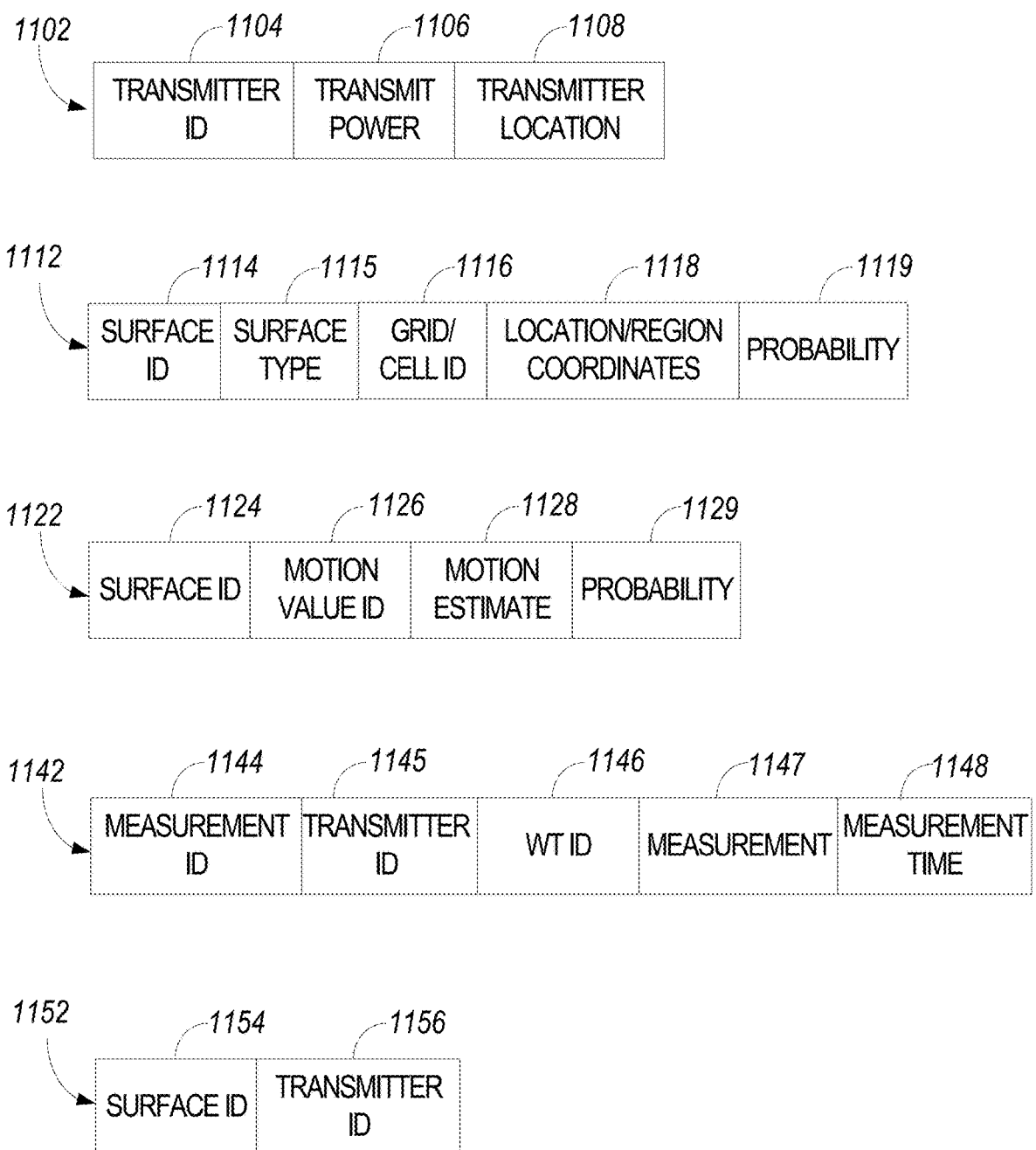
FIG. 11 shows example data structures that are implemented in one or more of the disclosed embodiments.

FIG. 11 shows example data structures that are implemented in one or more of the disclosed embodiments. While the data structures are discussed as relational database tables, one of skill would understand that the disclosed embodiments can use a variety of different data structure types, including traditional in-memory data structures such as linked lists, arrays, graphs, trees, or a non-structured data structure, hierarchical data store, object oriented data store, serialized data storage, or any other data structure architecture.

FIG. 11 shows a wireless transmitter table 1102, location probability surface table 1112, a motion probability surface table 1122, a signal table 1142, and a surface mapping table 1152. The wireless transmitter table 1102 indicates locations of known wireless transmitters. The wireless transmitter table 1102 includes, transmitter identifier field 1104, transmit power field 1106, and transmitter location field 1108. The transmitter identifier field 1104 uniquely identifies a wireless transmitter. The transmit power field 1106 indicates a power level used by the transmitter (identified via field 1104). The transmit power information included in the transmit power field 1106 is used by at least some of the disclosed embodiments to determine an expected signal strength of the wireless transmitter in different regions of different distances from the wireless transmitter. The transmitter location field 1108 indicates a geographic location of the wireless transmitter (e.g. latitude, longitude, and height e.g., above floor level, values). The transmitter location information included in the transmitter location field 1108 is used by at least some of the disclosed embodiments to calculate a distance between the wireless transmitter and different regions (e.g. 114*a-c*) within a geographic area (e.g. 112).

The location probability surface table 1112 includes a surface identifier field 1114, surface type field 1115, grid/cell identifier field 1116, location/region coordinates field 1118, and a probability field 1119. The surface identifier field 1114 uniquely identifies a surface. The identified surface can be a location probability surface (based on signal strength information from a single wireless transmitter), or a composite location probability surface (based on multiple location probability surfaces), a predicted location probability surface, or a blended location probability surface. The surface type field 1115 indicates a type of surface. For example, the surface type field 1115 indicates, in various embodiments, whether the surface (identified via field 1114) is a location probability surface, predicted location probability surface, blended location probability surface, or composite location probability surface. The grid/cell identifier field 1116 uniquely identifies a cell/grid or region included in the surface. For example, in some embodiments, the field 1116 identifies one of the regions 114*a-c* shown in FIG. 1. The location/region coordinates field 1118 defines boundaries of a region corresponding to the grid or cell identified in field 1116. For example, in some embodiments, the field 1118 defines coordinates of center of a geographic region (e.g. any one of 114*a-c*). The probability field 1119 stores a probability value that a wireless terminal is located within the region (represented by the grid/cell identified via grid/cell identifier field 1116). Note that each row of the example location probability surface table 1112 represents a single cell in a probability surface. Thus, surfaces, which typically include multiple cells, are represented by the location probability surface table 1112 via multiple rows, each row having an equivalent surface identifier field 1114 value, but different grid/cell id field 1116 values. Other methods of representing a probability surface are contemplated by the disclosed embodiments and are not limited by the example representation provided by FIG. 11.

The motion probability surface table 1122 includes a motion probability surface identifier field 1124, motion estimate identifier field 1126, motion estimate field 1128, and probability field 1129. The motion probability surface identifier field 1124 uniquely identifies a motion probability surface. For example, in some embodiments, a motion probability surface for a particular wireless terminal is generated at each time reference, such as the time references T0-T4 illustrated in FIG. 3. In some embodiments, the motion probability surface surface ID 1124 is equivalent to a unique wireless terminal ID such as WT ID 1005 of FIG. 10. Some embodiments generate motion probability surfaces for a plurality of different wireless terminals. Each of these different motion probability surfaces would be distinguished and identified via the motion probability surface identifier field 1124 which identifies the specific wireless terminal associated with said motion probability surface. The motion estimate identifier field 1126 uniquely identifies a particular cell or motion estimate/probability included in the motion probability surface. The motion estimate field 1128 indicates one possible motion estimate of a wireless terminal at a specific time. The motion estimate field 1128 is represented, in some embodiments, via a $V_x$, $V_y$, and $V_z$ value. Other embodiments represent motion using other parameters. The probability field 1129 stores a probability that the wireless terminal exhibits motion according to that specified by the motion estimate field 1128 at the specific time. Note that each row of the motion probability surface table 1122 represents a single cell in a motion probability surface. Thus, motion probability surfaces, which typically include multiple cells, are represented by the motion probability surface table 1122 via multiple rows, each row having the same surface identifier field 1124 value, but different motion value id fields 1126. Other methods of representing a motion probability surface are contemplated by the disclosed embodiments and are not limited by the example representation provided by FIG. 11.

The signal table 1142 includes a measurement identifier field 1144, transmitter identifier field 1145, wireless terminal identifier field 1146, measurement field 1147, and a measurement time field 1148. The measurement identifier field 1144 uniquely identifies a particular signal measurement.

The transmitter identifier field 1145 identifies a wireless transmitter generating the signal. The wireless terminal identifier field 1146 identifies a wireless terminal measuring the signal. The measurement field 1147 stores a value of the signal (generated by transmitter identified via transmitter identifier field 1145) measurement by the wireless terminal (identified via 1146). The measurement time field 1148 identifies a time at which the measurement was either performed or received by a network management system (e.g. 110).

The surface mapping table 1152 includes a surface identifier field 1154, and a wireless transmitter identifier field 1156. The surface identifier field 1154 uniquely identifies a probability surface. In some embodiments, the surface identifier field 1154 is cross-referenced with the surface identifier field 1114. The wireless transmitter identifier field 1156 identifies a wireless transmitter. In some embodiments, the wireless transmitter identifier field 1156 identifies a wireless transmitter from which signals are measured to generate the surface that is identified by the surface identifier field 1154.

Figure 12:
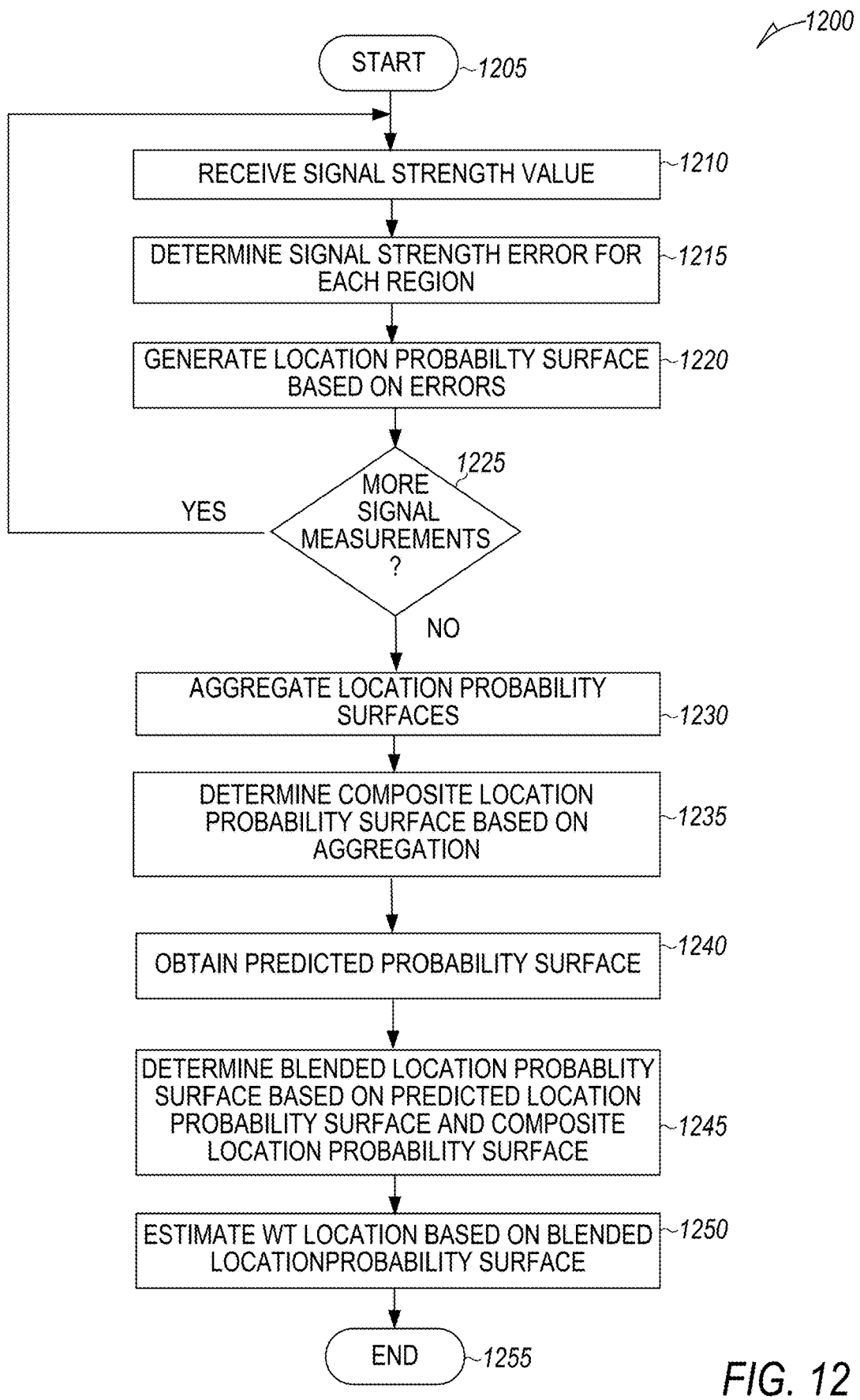
FIG. 12 is a flowchart of a method for estimating a location of a wireless terminal.

FIG. 12 is a flowchart of a method for estimating a location of a wireless terminal. In some embodiments, one or more of the functions discussed below with respect to FIG. 12 and the method 1200 is performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below.

After start operation 1205, the method 1200 moves to operation 1210, where a signal strength value is received. In some embodiments, the signal strength value is represented via a received signal strength indication (RSSI). The signal strength represents strength of a signal received by the wireless terminal originating from a wireless transmitter. The signal strength is measured by a wireless terminal (e.g. 106). For example, as discussed above with respect to FIG. 1, the wireless terminal 106 receives signals from one or more wireless transmitters such as one or more of the access points 102*a-d*. The signal strength value is received, in some embodiments, by the network management system 110 from a wireless terminal (e.g. 106). The signal strength value is received in a message in some embodiments. The message is received, in some embodiments, indirectly from the wireless terminal via an access point (e.g. 102*a-d*).

In operation 1215, a signal strength error is determined for a plurality of regions in a geographic area. For example, as discussed above with respect to FIG. 1, a geographic area is divided into a plurality of regions (e.g. 114*a-c*). An expected signal strength for each region is determined based on a distance between the wireless transmitter and a center point or other representative point of the respective region. The expected signal strength is further based, in some embodiments, on a transmit power of the wireless transmitter. For example, in some embodiments, the network management system 110 receives transmit power information from one or more of the access points 102*a-d*. In some embodiments, the network management system, e.g., 110, controls a transmission power of the AP. This transmit power information is then used to determine the expected signal strength for each region based on the distance between the wireless transmitter and the region. Operation 1215 then relates the received signal strength value of operation 1210 to the expected signal strength to determine a signal strength error for the region. For example, in some embodiments, a difference between the received signal strength and the expected signal strength for the region is determined. The difference is the signal strength error in some embodiments. In some embodiments, an absolute value of the difference is the signal strength error. In some embodiments, the error for each region is determined according to Equation 2, discussed above. Thus, when determining probabilities that a wireless terminal is located in each region corresponding to a cell or grid location of a location probability surface, each probability of the location probability surface is based on a respective difference between the signal strength measurement upon which the surface is based and an expected signal strength of the wireless terminal when located in a region corresponding to the respective probability.

In operation 1220, a probability surface is generated based on the errors. A probability surface defines a correspondence between each region (e.g. any one of 114*a-c*) and a probability that the wireless terminal is located in the region. Thus, the probability surface defines a probability for each region of the surface. In some embodiments, the probability is inversely proportional to the error for the region. Thus, regions having low error are more likely to represent a location of the wireless terminal than regions having higher errors. Some embodiments use a Gaussian estimation to generate a probability of a region based on the error of the region.

Decision operation 1225 determines if there are additional signal measurements available. For example, additional signal measurements may be made of signals generated by other wireless transmitters (e.g. a different wireless transmitter for each iteration of operations 1210, 1215, and 1220. If there are additional signal measurements, the method 1200 returns to operation 1210, and generates an additional location probability surface. Otherwise, the method 1200 moves from decision operation 1225 to operation 1230, which aggregates the location probability surfaces generated in the iterations of operation 1210, 1215, and 1220 described above. For example, some embodiments aggregate corresponding probabilities in a first location probability surface and a second location probability surface. Aggregating the location probability surfaces includes, in some embodiments, multiplying probabilities in corresponding cells or grids of each surface (e.g. probabilities relating to the same region, grid, or cell of the different probability surfaces).

In operation 1235, a composite location probability surface is determined based on the aggregation. In other words, a composite location probability surface is comprised of the aggregated probabilities of operation 1230. Thus, corresponding cells of the location probability surfaces are aggregated, and the resulting value (probability) is stored in a corresponding cell of the composite location probability surface.

In operation 1240, a predicted location probability surface is obtained. Generation of a predicted location probability surface is explained further with respect to FIG. 14 below. As discussed above with respect to FIG. 3, a predicted location probability surface is generated based on a motion probability surface (or motion estimates of the WT) and one or more blended location probability surfaces from prior time periods or references. Equation 6 provides one example embodiment of how a predicted location probability surface is generated.

As discussed above, a motion probability surface defines possible motion directions and magnitudes along with a probability that the wireless terminal has each of the defined directions and magnitudes at the respective time. Thus, each cell or grid of the motion probability surface indicates a velocity direction and magnitude, (e.g. Vx, Vy, Vz), and a probability that the wireless terminal moved at that velocity magnitude and direction over a relevant time period. Motion probability surfaces are discussed in this disclosure. While some embodiments represent possible motion values using a motion probability surface, other data structures are used in other embodiments. For example, a multi-dimensional array is used in some embodiments, with a probability and motion value defined by each "row" of the multi-dimensional (e.g. column) array.

In operation 1245, a blended location probability surface is determined. The blended location probability surface is based on the composite location probability surface determined in operation 1235. As discussed above, for example with respect to FIG. 3, the blended location probability surface is also based on a predicted location probability surface One embodiment of generating a predicted location probability surface based on the motion probability surface is discussed below with respect to FIG. 14. Other methods are also within the scope of the disclosed embodiments.

In operation 1250, a location of the wireless terminal is determined based on the blended location probability surface. For example, in some embodiments, as discussed above, a region having a highest indicated probability associated with it in the blended location probability surface is used as the estimated location. If multiple regions have the same highest probability, an area that aggregates the two regions may be used as the estimated location. In some embodiments, regions represented by the blended location probability surface are ranked according to their associated probabilities. A predetermined number of regions or a predetermined percentage of regions having the largest probabilities are identified. The identified regions are then used in determining the location estimate, with other regions excluded from the location estimate. In other embodiments, a weighted mean of contiguous regions is used to estimate the location of the wireless terminal. After the location of the wireless terminal is estimated, the method 1200 moves to end block 1255.

Figure 13A:
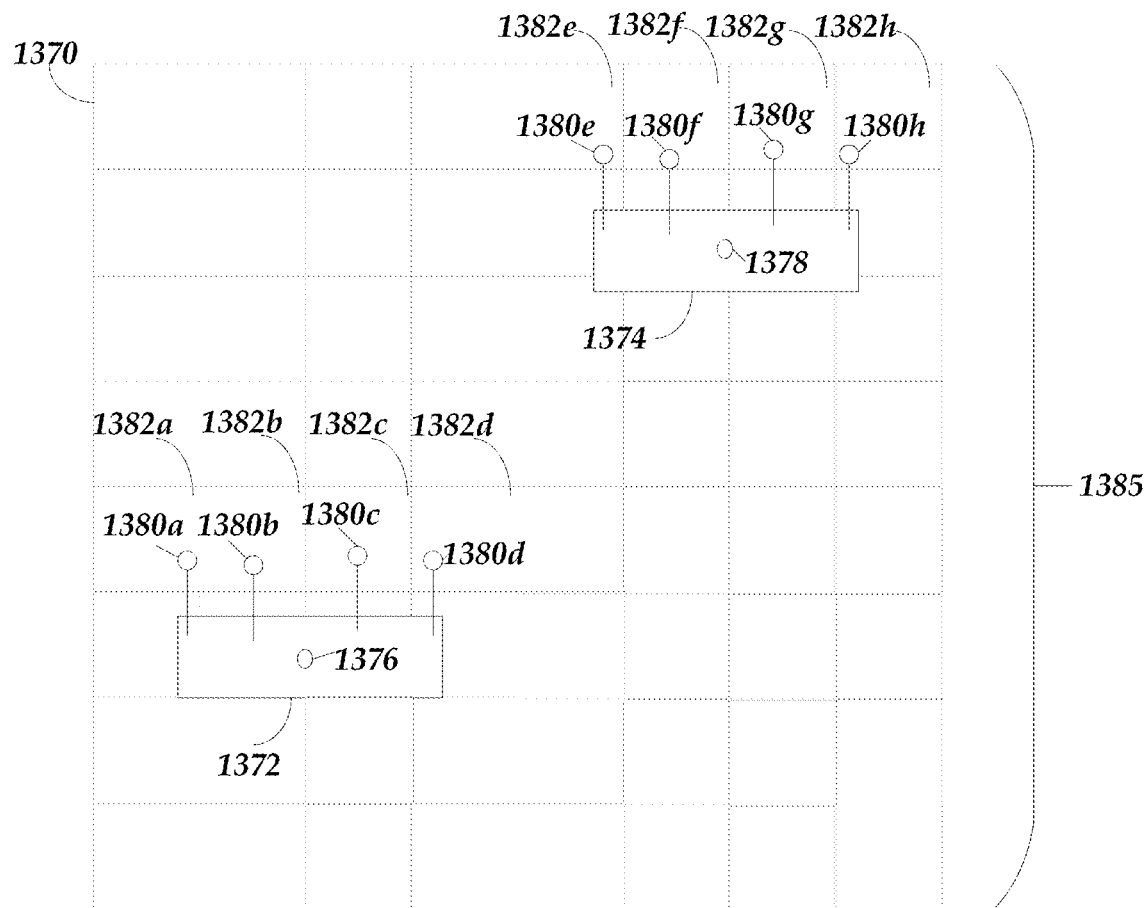
FIG. 13A shows a transmitting device and a receiving device within a plurality of regions.
Figure 13B:
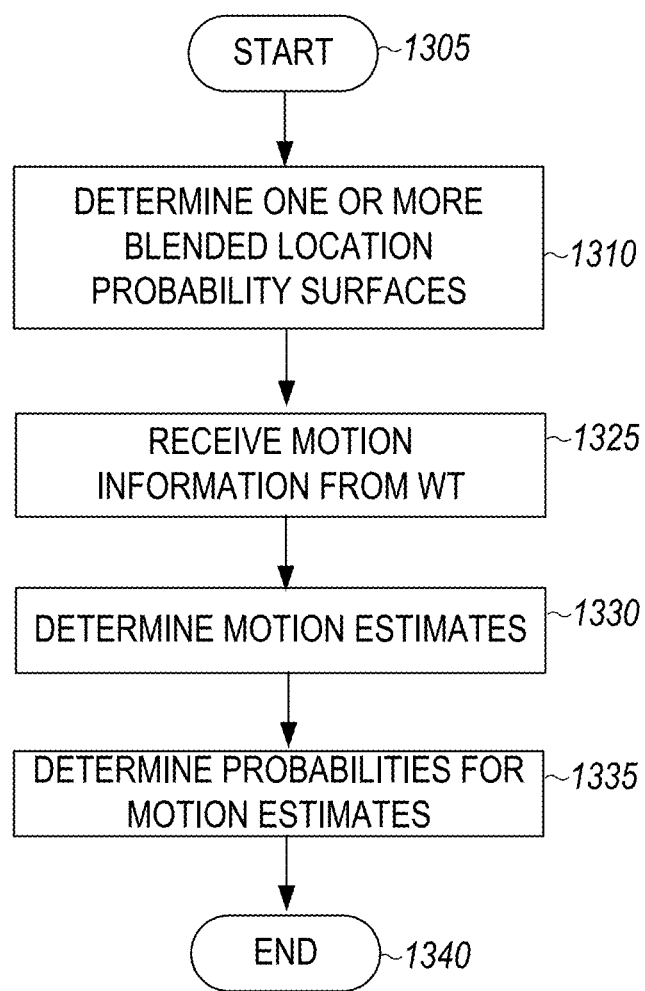
FIG. 13B is a flowchart of a method for determining a motion probability surface.

FIG. 13A shows a transmitting device and a receiving device within a plurality of regions. FIG. 13A shows a geographic area 1385 that is divided into a plurality of regions, such as region 1370. FIG. 13A also shows two devices, a transmitting device 1372 and a receiving device 1374. The transmitting device 1372 includes a plurality of transmit elements. In the illustrated embodiment of FIG. 13A, the transmitting device 1372 includes four transmit elements, transmit element 1380a, transmit element 1380b, transmit element 1380c, and transmit element 1380d. The receiving device 1374 includes a plurality of receive elements. In the illustrated embodiment, the receiving device include four receive elements, including receive element 1380e, receive element 1380f, receive element 1380g, and receive element 1380h. In at least some embodiments, each of the plurality of transmit elements are located in a different one of the plurality of regions. For example, FIG. 13A shows that transmit element 1380a is located in region 1382a. Transmit element 1380b is located in region 1382b. Transmit element 1380c is located in region 1382c. Transmit element 1380d is located in region 1382d. Similarly, each of the plurality of receive elements are located in a separate region of the plurality of regions 1385. Receive element 1380e is located in region 1382e. Receive element 138f is located in region 1382f. Receive element 1380g is located in region 1382g. Receive element 1380h is located in region 1382h.

FIG. 13A also shows that each of the transmitting device 1372 and receiving device 1374 have corresponding reference points, shown as reference point 1376 for transmitting device 1372 and reference point 1378 for receiving device 1374. Some of the disclosed embodiments maintain layout information for each of the devices 1372 and 1374. Layout information for the transmitting device 1372 defines relative positions of each of the transmitting elements 1380a-d and the reference point 1376. Layout information for the receiving device 1374 defines relative positions of each of the receive elements 1380e-h and the reference point 1378.

As discussed above, in at least some embodiments, the transmitting device 1372 transmits one or more signals to the receiving device 1374. The signals are received at each of the receive elements 1382e-h. Because the receive elements are located at different distances from any one of the transmit elements 1380a-d, the signals are received at each of the receive element 1382e-h with different phases. Thus, phase difference information is generated, in some embodiments, that describes the differences in phase of signals received from one or more of the transmit elements 1380a-d by the receive elements 1380e-h.

In at least some embodiments, locations of each of the receive elements 1380e-h are known. In other words, some embodiments store data indicating that receive element 1380e is located in region 1382e, receive element 1380f is located in region 1382f, receive element 1380g is located in region 1382g, and receive element 1380h is located in region 1382h. In another example embodiment, data indictive of the x, y, and z coordinates and the orientation of the receiving wireless device is stored. Based on these known locations of each of the receive elements 1382e-h, some embodiments generate, for each of the plurality of regions 1385, expected phase differences that would be experienced by the receiving device 1374 resulting from a signal transmitted from each of the plurality of regions 1385. Thus, in some embodiments, the transmitting device transmits at least one signal from each of the transmit elements 1382a-d, which are received by at least two of the receive elements 1380e-h. By comparing phase differences of the received signals to expected phase differences generated for each of the plurality of regions 235, the disclosed embodiments are able to identify in which region each of the transmit elements 1382a-d are located.

Once locations of each of the transmit elements 1380a-d is known (e.g. the regions 1382a-d respectively), some of the disclosed embodiments determine an orientation of the transmitting device 1372 based on the known locations of the transmit elements 1380a-d.

For example, a distance between a time of arrival of the waveform at the respective receive elements of the receivers is given by $$\Delta t = t1 - t2 = (D1 - D2)/S_{wave} = \Delta D/S_{wave} \qquad \text{Eq. 11}$$

where:

$\Delta t$ difference in time of arrival of the waveform at two receive elements, $\Delta D$ difference between travel distances of the signal/wave, t1 travel time of waveform from a transmit element to a first receive element, t2 travel time of waveform from the transmit element to a second receive element, D1 distance from the transmit element to the first receive element, D2 distance from the transmit element to the second receive element, $S_{wave}$ speed of the waveform via the medium The speed of the wave through a medium is related to the frequency of the wave by $$S_{wave} = f_{wave} * \lambda \qquad \text{Eq. 12}$$

where:
$S_{wave}$ speed of the waveform via the medium,
$f_{wave}$—frequency of the wave,
$\lambda$ wavelength of the wave.
The time duration of a wave is related to its frequency by:

$$T = 1/f_{wave} \qquad \text{Eq. 13}$$

where the time duration of the wave can be also expressed in angle as 360 degrees or $2\pi$.
Substituting Equation 13 in Equation 12 results in $$\Delta t = t1 - t2 = \Delta D / S_{wave} = \Delta D / (f_{wave} * \lambda) \qquad \text{Eq. 14}$$

And using the relationship of equation 13 results in $$\Delta t = \Delta D * T / \lambda = \Delta D * 2\pi / \lambda \qquad \text{Eq. 15}$$

Or $$\Delta D = \lambda * \Delta t / T = \lambda * \Delta \phi / 2\pi \qquad \text{Eq. 16a}$$

Or $$\Delta \phi = 2\pi * \Delta D / \lambda \qquad \text{Eq. 16b}$$

where:
$\Delta \phi$ difference in arrival phase of the waveform at the two receive elements.
Some embodiments rely on Equation 17 below to determine the position of a wireless device:

$$\text{Position} = \text{Position Min}\left(\sum_{i=1}^{n} f(di)\right) \qquad \text{Eq. 17}$$

where:
Position description of the location of device antennas,
Position Min ( ) positions of antennas that minimize the term in the ( ), and
$f(d_i)$ function of the distances between the estimated positions of the antennas and the physical distances of the antennas.
In some embodiments, the function f(di) is a mean square of the distances function. In another embodiment the function f(di) is an absolute value. Other functions are contemplated by the disclosed embodiments.

FIG. 13B is a flowchart of a method for determining motion estimates for a wireless terminal. The motion estimates define a plurality of possible distinct motion parameter sets for a wireless terminal. For example, in some embodiments, each of the motion parameter sets indicate a direction and magnitude (e.g. via Vx, Vy, and Vz values) of the wireless terminal. Associated with each of the motion estimates is a probability that a wireless terminal exhibits motion in accordance with the motion estimate. In some embodiments the plurality of motion estimates and probabilities for a wireless terminal at a particular time are represented as a motion probability surface. A motion probability surface generally defines possible motion of a wireless terminal at a specific time. For example, if a first and second blended location probability surface are determined for a first and second time period respectively, a motion probability surface can determine possible motion of the wireless terminal during a time spanning the first and second time periods to help explain how the wireless terminal moved between the location estimate provided by the first blended probability surface and a second location estimate provided by the second blended location probability surface.

In some embodiments, one or more of the functions discussed below with respect to FIG. 13B and the method 1300 are performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below.

After start operation 1305, one or more blended location probability surfaces for the wireless terminal are determined in operation 1310. For example, as discussed above with respect to FIG. 3, blended location probability surfaces 308a and 308b are provided as input when generating motion probability surface 306c or motion estimates and probabilities organized in another form. An example of a determination of a blended location probability surface is described above with respect to FIG. 12 and operation 1245.

In operation 1325, motion information is received from the wireless terminal. This motion information indicates, in various embodiments, one or more of a speed of the wireless terminal, acceleration information for the wireless terminal, and a direction of the wireless terminal. The motion information indicates accelerations of the wireless terminal in three dimensions, in at least some embodiments. The motion information also indicates, in some embodiments, a variability or accuracy of the direction, speed, and/or acceleration information.

In operation 1330, the motion estimates are generated based on the received motion information and the one or more blended location probability surfaces. In some embodiments, the motion estimates determine velocity in two or three dimensions based on location estimates derived from each of the blended location probability surfaces (e.g. highest probability region in each surface, or other methods discussed above). These velocity estimates are then augmented by integrating the acceleration information within a time period to which the velocity estimates pertain. In some embodiments, the acceleration information received from the wireless terminal (e.g. via operation 1325) is integrated over half of the applicable time period and added to the velocity estimates derived from the blended probability surfaces. Given the accelerometer in wireless terminals is subject to drift, augmenting the velocity estimates provided by the blended location probability surfaces by integrating the acceleration over a single time period prevents a built up of error which could otherwise accumulate if acceleration was integrated over multiple time periods.

As discussed above, in some embodiments, the motion estimates generated in operation 1330, along with their associated probabilities, are represented as a motion probability surface. One embodiment of operation 1330 is discussed below with respect to FIG. 15 and the method 1500. In operation 1335, probabilities for each of the motion estimates are determined. In some embodiments, operation 1335 collectively conforms the probabilities for the motion estimates to a predetermined distribution, such as a Gaussian distribution. After operation 1335 completes, the method 1300 moves to end operation 1340.

FIG. 14 is a flowchart of a method for generating a predicted location probability surface. As discussed above with respect to FIG. 3, a predicted location probability surface is generated at a first time reference (or period), and predicts a probability surface of a wireless terminal at a future time reference (or time period). For example, FIG. 14 shows a blended location probability surface for a time T1. A motion probability surface for time T1 is referenced, and a predicted location probability surface for time T2 is referenced. These different time references associated with these various surfaces is consistent with the explanation of FIG. 3 above, which shows a blended location probability surface 308c from time reference T2 and motion estimates 306c (represented as a motion probability surface in at least some embodiments) from time reference T2 used to generate a predicted location probability surface 307d for time reference T3.

In some embodiments, one or more of the functions discussed below with respect to FIG. 14 and the method 1400 is performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below.

After start operation 1405, the method 1400 moves to operation 1410, which selects a region or location cell in a blended location probability surface The blended location probability surface is generated for a time T=1.

In operation 1415, a cell in a motion probability surface is selected. The motion probability surface is for a time T=1. In operation 1420, a probability defined by the selected motion cell is obtained. A motion estimate of the wireless terminal defined by the cell is also obtained. In various embodiments, the motion estimate defines velocities in one or more of an x, y, and z direction (e.g. $V_x$, $V_y$, $V_z$).

In operation 1425, a new location is determined based on the selected location cell and the motion information. For example, operation 1425 determines the new location or resulting region by determining in which region the wireless terminal would be located if it exhibited the motion defined by the motion estimate for a time interval. The time interval, in some embodiments, is an elapsed time between two sequentially determined blended location probability surfaces (e.g. elapsed time between t=1 and t=2).

In operation 1430, a probability that the wireless terminal moves to the new location cell is determined. This probability is based on two probabilities. A first probability is a probability associated with the selected location cell (e.g. from operation 1410). A second probability is associated with the selected cell of the motion probability surface (e.g. via operation 1415). These two probabilities are aggregated (e.g. multiplied in some embodiments) to arrive at a probability of a wireless terminal in the selected location exhibiting the motion and moving to the new location. In operation 1435, the resulting probability is associated with the cell corresponding to the new location.

Decision operation 1440 determines if there are additional motion estimates (e.g. cells in the motion probability surface) for the wireless terminal. If there are, processing returns to operation 1415 and a different motion estimate (e.g. cell in the motion probability surface) is selected. Otherwise, the method 1400 moves from decision operation 1440 to decision operation 1445.

Decision operation 1445 determines if there are additional regions or cells in the blended location probability surface to process. If not, the method 1400 moves to operation 1450. Otherwise, processing returns to operation 1410 and a different region or cell is selected.

In operation 1450, corresponding probabilities determined by operation 1430/1435 are aggregated. In other words, probabilities associated with the same region or cell in the new predicted location probability surface are aggregated (e.g. added). In other words, if two or more motion estimates included in the motion probability surface have equivalent resulting regions, probabilities associated with those motion estimates are aggregated and assigned to a corresponding region in the predicted location probability surface. Thus, the predicted location probability surface indicates a probability that a wireless terminal will be located in a particular region based on an aggregated probability of the region. The new predicted location probability surface corresponds to location of WT at time T2. (e.g. one time period subsequent to the blended location probability surface of operation 1410 and one time period subsequent to the motion estimates or motion probability surface of operation 1415). After operation 1450, the method 1400 moves to end operation 1455.

Figure 15:
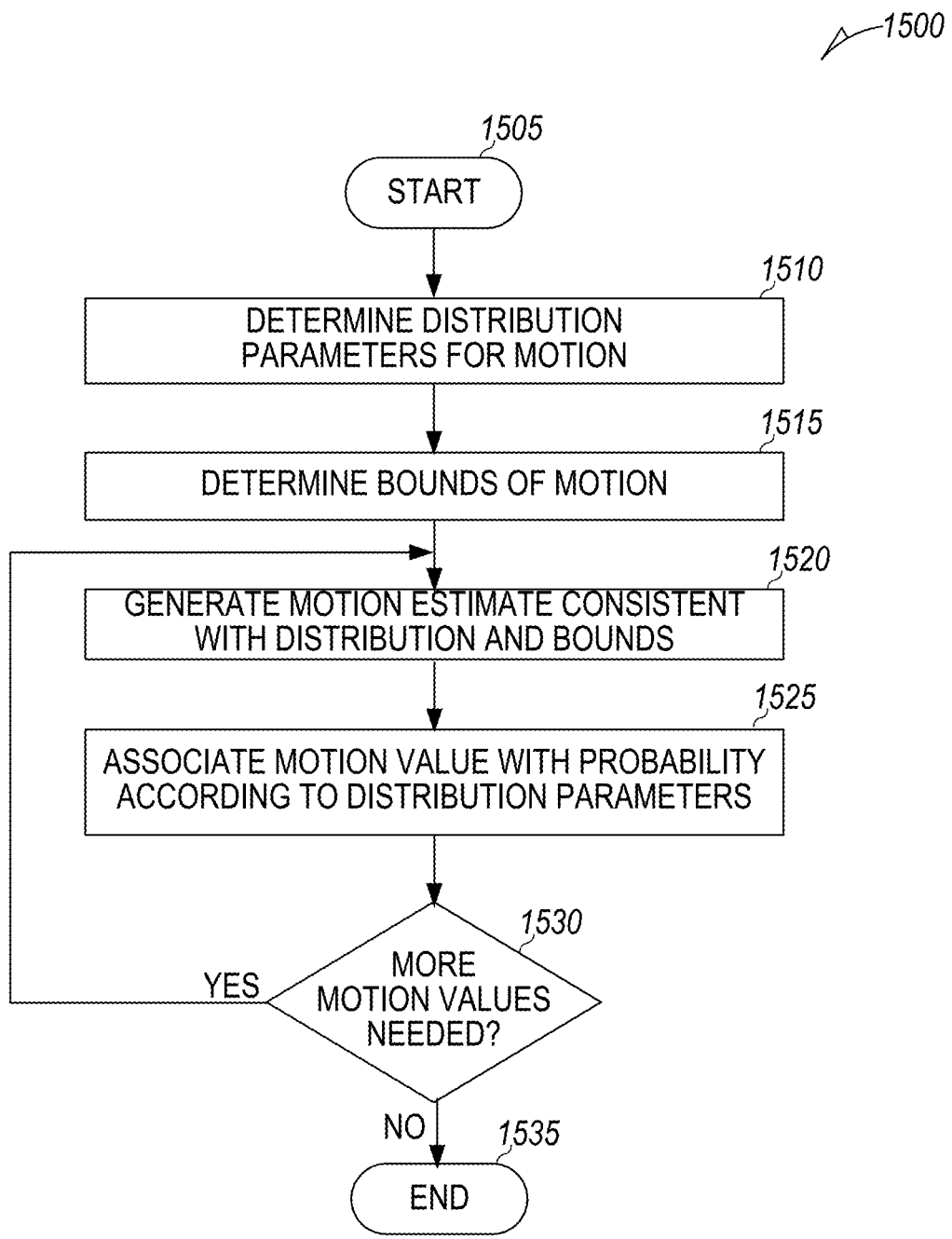
FIG. 15 is a flowchart of a method for determining a motion probability surface.

FIG. 15 is a flowchart of a method for determining a plurality of different motion estimates for a wireless terminal. In some embodiments, these motion estimates are represented as a motion probability surface. In other embodiments, the motion estimates of a wireless terminal are represented as a group of data values defining the motion estimates and the probabilities that the WT moves at the specific speed and direction, for example, using an array or other data structure configured to store a plurality of data values. In some embodiments, one or more of the functions discussed below with respect to FIG. 15 and the method 1500 is performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below.

After start operation 1505, the method 1500 moves to operation 1510. In operation 1510, probability distribution parameters for motion of a wireless terminal are determined. In some aspects, the probability distribution parameters are determined based on variability information in the motion of the wireless terminal. For example, in some aspects, the probability distribution parameters are based on the accuracy field 1025. In some aspects, the probability distribution parameters define a type of probability distribution. For example, the probability distribution parameters define, in some embodiments whether the probability distribution is a Gaussian distribution, a Cauchy distribution, a Behrens-Fisher distribution, a Laplace distribution, or any other type of probability distribution.

In operation 1515, bounding parameters on the motion are determined. For example, in some embodiments, an average motion value or mean motion value is determined. In some embodiments, limits on the motion are determined. For example, some embodiments of operation 1515 determines motion values (e.g. motion estimate field 1128) that define lower and upper percentiles of the distribution. In some embodiments, motion estimate limits are based on the lower and upper percentiles. In some embodiments, the limits are based on multiples of a standard deviation of motion values. For example, some embodiments limit the generated motion estimates to no more than five standard deviations from a mean motion estimate.

In operation 1520, a motion estimate is generated (e.g. as stored in motion estimate field 1128). The motion estimate is generated based on the determined bounds of motion and the distribution parameters in some embodiments. In some embodiments, the motion estimate is generated based on one or more blended location probability surfaces, as described above with respect to FIG. 3 (e.g. blended location probability surfaces 308a and 308b are used to generate motion estimates 306c (in some embodiments represented as a motion probability surface). This is also referenced above with respect to operation 1310. In some embodiments, the motion estimate is generated based on acceleration information provided by the wireless terminal (e.g. as described above with respect to operation 1325).

In operation 1525, a motion value is associated with a motion probability according to the distribution parameters. For example, in a normal or Gaussian distribution, values closer to the mean are more numerous than values further from the mean. Thus, operation 1525 associates motion values with their probability of occurrence so as to build a probability distribution of motion values in accordance with the motion parameters (variance, bounds, median, or mean), and distribution parameters. Thus, a result of operation 1525 is a motion estimate and associated motion probability. Thus, the motion estimates included in a motion probability surface have associated motion probabilities.

Decision operation 1530 determines whether more motion values are needed to complete the distribution. If more values are needed, the method 1500 returns to operation 1520. Otherwise, the method 1500 moves from decision operation 1530 to end operation 1535.

Figure 16:
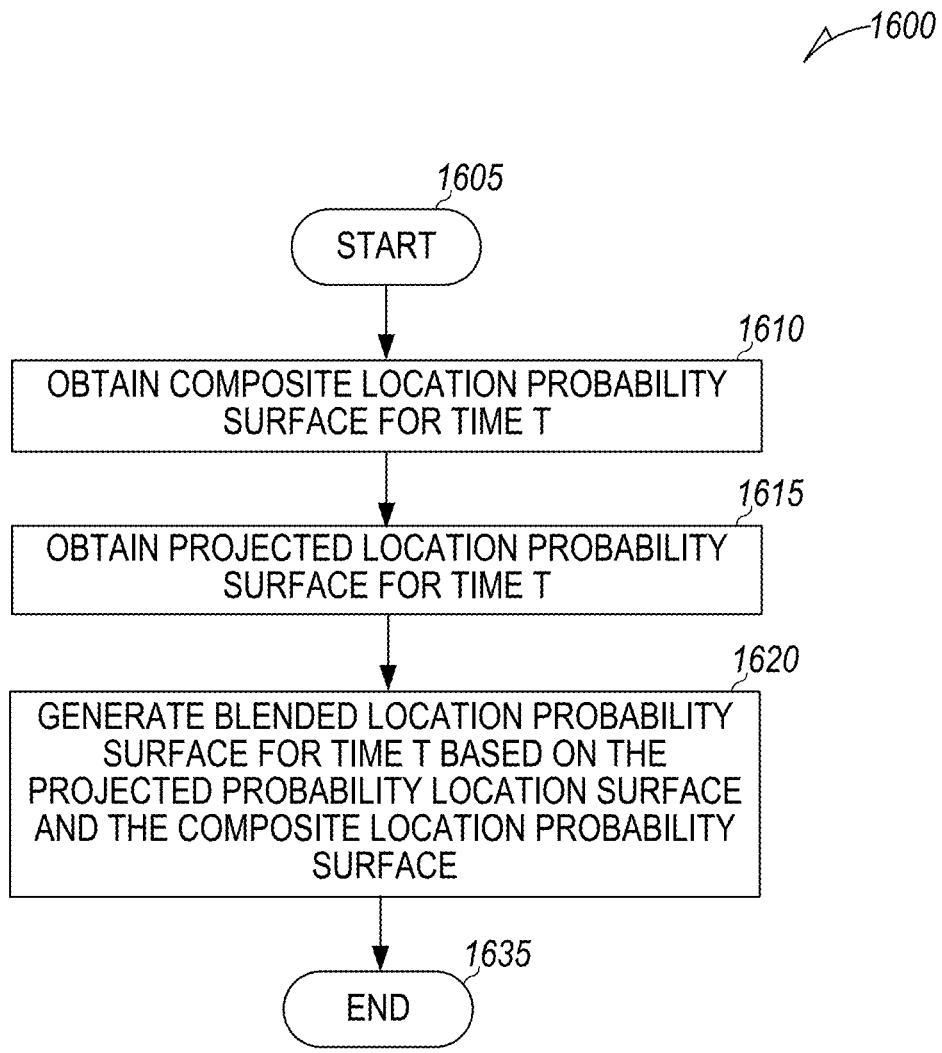
FIG. 16 is a flowchart of a method for determining a blended location probability surface.

FIG. 16 is a flowchart of a method for determining blended probably surface for a wireless terminal based on a predicted location probability surface and a composite location probability surface. For example, the method 1600 discussed below with respect to FIG. 16 represents one example embodiments of how the blended location probability surface 308d is generated based on predicted location probability surface 307d and composite location probability surface 304d.

In some embodiments, one or more of the functions discussed below with respect to FIG. 16 and the method 1600 is performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below.

After start operation 1605, the method 1600 moves to operation 1610. In operation 1610, a composite location probability surface is obtained. For example, in some embodiments operation 1610 includes operations 1210-1235, discussed above with respect to FIG. 12.

Operation 1615 obtains a predicted location probability surface. In some embodiments, operation 1615 obtains a predicted location probability surface according to the method 1400, discussed above with respect to FIG. 14. For example, a predicted location probability surface for time T is based, in some embodiments, on one or more blended location probability surfaces for times T-1, T-2, etc. and a motion surface generated at time T-1 or motion estimates for the mobile terminal at time T-1.

Operation 1620 generates a blended location probability surface for time T based on the predicted location probability surface and the composite location probability surface. In some embodiments, operation 1620 averages corresponding cells or regions of each of the composite location probability surface and the predicted location probability surface to generate a corresponding cell or region of the blended location probability surface. Corresponding cells in this context are cells representing equivalent geographical regions. In some embodiments, a weighted average is used to generate the blended location probability surface, with probabilities indicated by the composite location probability surface given a first weight and probabilities indicated by the predicted location probability surface given a second different weight. After operation 1620 completes, the method 1600 moves to end operation 1635.

Figure 17:
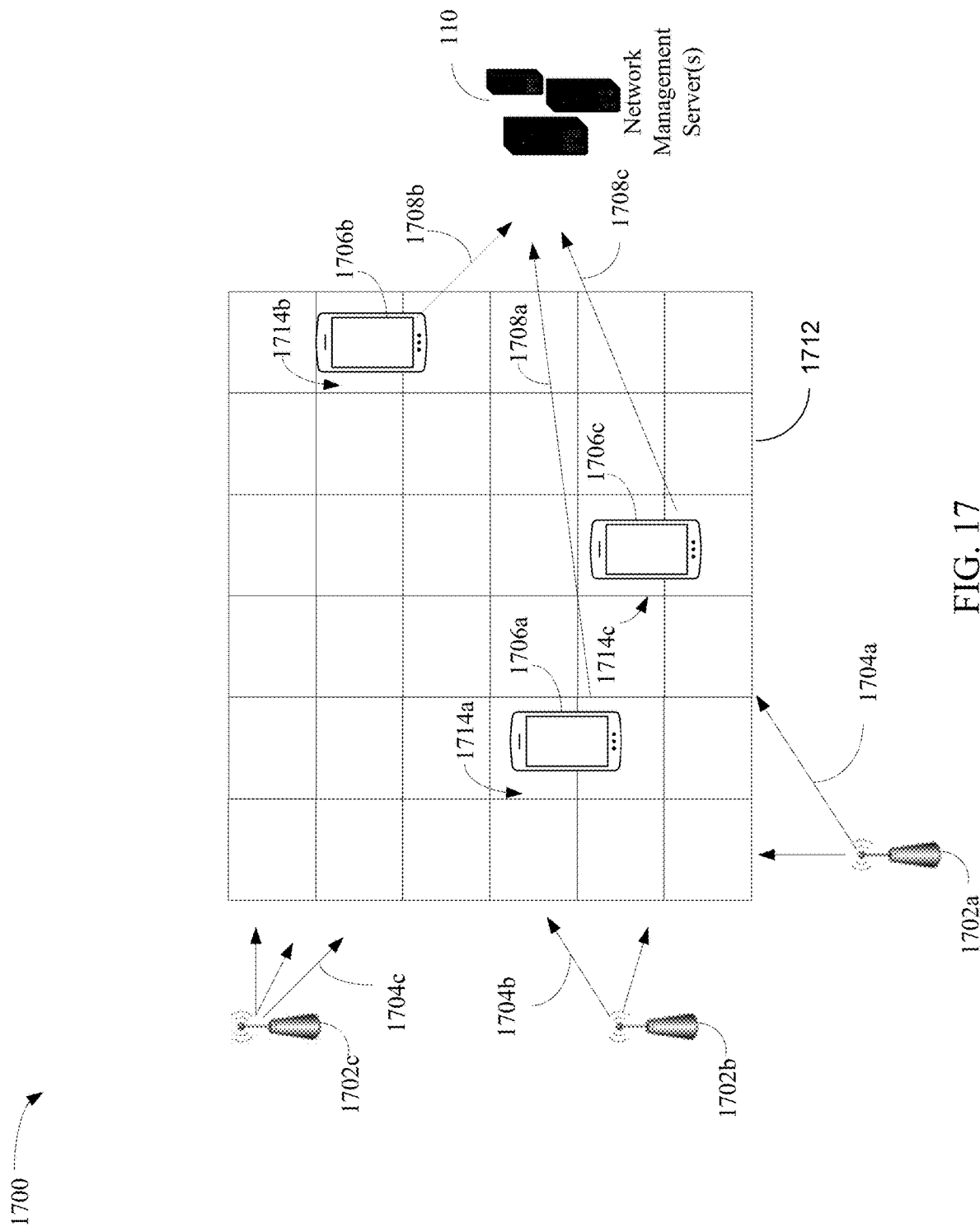
FIG. 17 is an overview diagram of a system that is implemented in one or more of the disclosed embodiments.

FIG. 17 is an overview diagram of a system 1700 that is implemented in one or more of the disclosed embodiments. The system 1700 includes three access points (APs) 1702a-c. Each of the four access points 1702a-c generates corresponding wireless signals 1704a-c. Signal 1704a, signal 1704b, and signal 1704c are received by wireless terminals 1706a-c. The wireless terminals 1706a-c measure a strength of each of the signals 1704a-c and generates messages 1708a-c indicating strengths of signals transmitted by one or more of the APs 1702a-c. For example, FIG. 17 shows the message 1708a indicating a signal strength (e.g. RSSI) by wireless terminal 1706a of signals transmitted by each of the access points 1702a-c. Message 1708b is transmitted by wireless terminal 1706b, and indicates signals strength information of signals received by the wireless terminal 1706b from one or more of the access points 1702a-c. Message 108c is transmitted by wireless terminal 1706c and indicates signal strength information of signals received by the wireless terminal 1706c from access points 1702a-c. RSSI is just one example of a signal strength measurement and other embodiments use different measurements for signal strength. In some example implementations wireless terminals 1706a-c use messages 1708a-c to convey accelerometer and or velocity information to the NMS 110.

The wireless terminals 1706a-c transmit the messages 1708a-c to a NMS 110. Though the messages are drawn as being sent directly to the proximity servers, it is understood that the message actually pass through the APs with which devices 1706a-s are associated. The NMS 110 utilizes the signal strength measurements included in the messages 1708a-c to estimate a position or geographic location of each one of the wireless terminals 1706a-c. In some embodiments, the NMS 110 divides a geographic area 1712 into a plurality of regions 1714a-n. Region 1714a, region 1714b, and region 1714c are illustrated in FIG. 17, while other regions within the geographic area 1712 are not labeled to preserve figure clarity. In some of the disclosed embodiments, the NMS 110 calculates for each wireless terminal 1706a-c a probability that the wireless terminal 1706 is located in each of the plurality of regions (including the regions 1714a-c). These probabilities are based on the signals 1704a-c received by the wireless terminals 1706a-c. In particular, the probabilities are based on strengths of the signals 1704a-c as measured by the wireless terminals. In some embodiments, the access points 1702a-c are at known locations. Thus, a distance between each access point 1702a-c and each region (e.g. 1714a-c) can be determined. From these distances, an expected signal strength of a signal received from each of the access points 1702a-c at each of the regions (e.g. 1714a-c) is determined. By comparing an expected received signal strength to a signal strength as measured by the wireless terminal, a probability that the wireless terminal is in the region can be determined.

In some embodiments, these probabilities are refined via additional probabilities of the wireless terminal's location that are based on motion information for the wireless terminal. For example, in some embodiments, the wireless terminal provides motion information, e.g., information extracted from the accelerometer inside the device, to the NMS 110 in a message (e.g. 1708*a*-*c*). In other embodiments, a different message is used to provide motion information from the wireless terminals 1706*a*-*c* to the NMS 110. The wireless terminals 1706*a*-*c* derive the motion information from, in some embodiments, an accelerometer that is integrated into one or more of the wireless terminals 1706*a*-*c*.

In some embodiments, motion of any one or more of the wireless terminal 1706*a*-*c* is determined by the NMS 110 based on changes in sequential determinations of the wireless terminal's location, as explained in the incorporated disclosures.

Figure 18A:
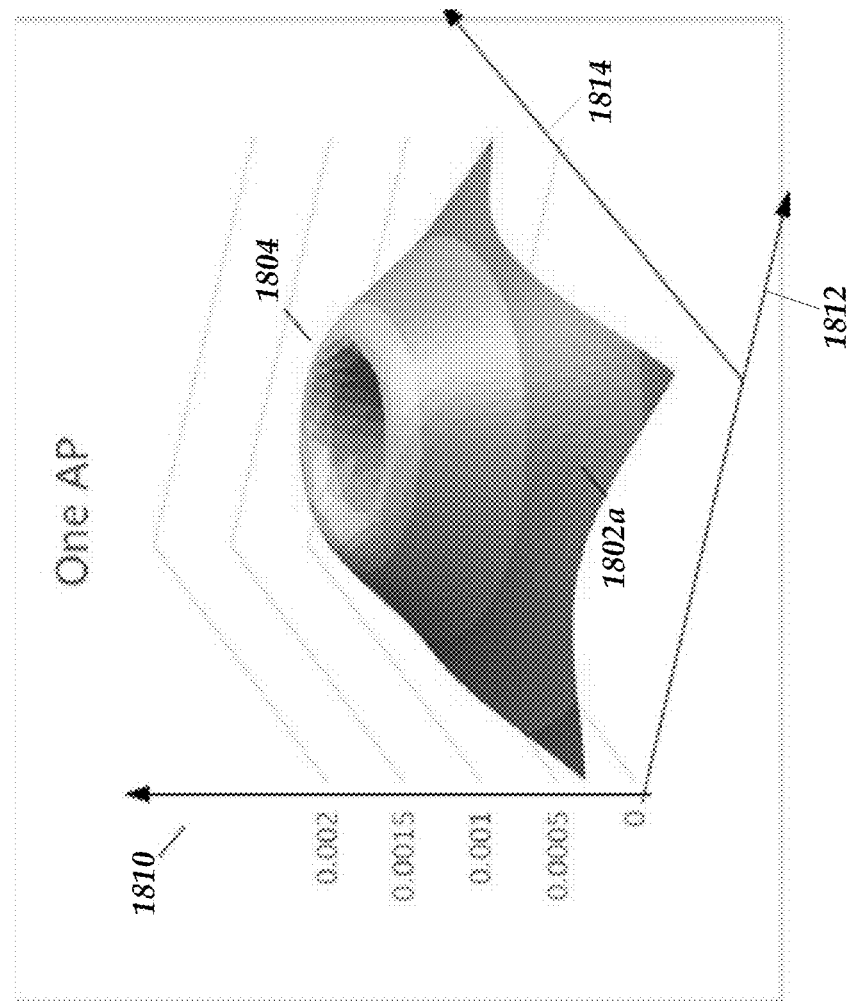
FIGS. 18A-C shows aggregation of a plurality of location probability surfaces.

FIG. 18A is a graphical representation 1800*a* of probabilities of an example two-dimensional location probability surface based on received signal strength from a single AP. The X axis 1812 and Y axis 1814 define the location or region in which the device is estimated to be located. The Z axis 1810 represents the probability that the device is in the said region or location. The probability surface 1802*a* exhibits a donut shape. The donut shape illustrates a ring 1804 of relatively high probability locations for a subject device, with surrounding regions exhibiting lower probabilities.

Figure 18B:
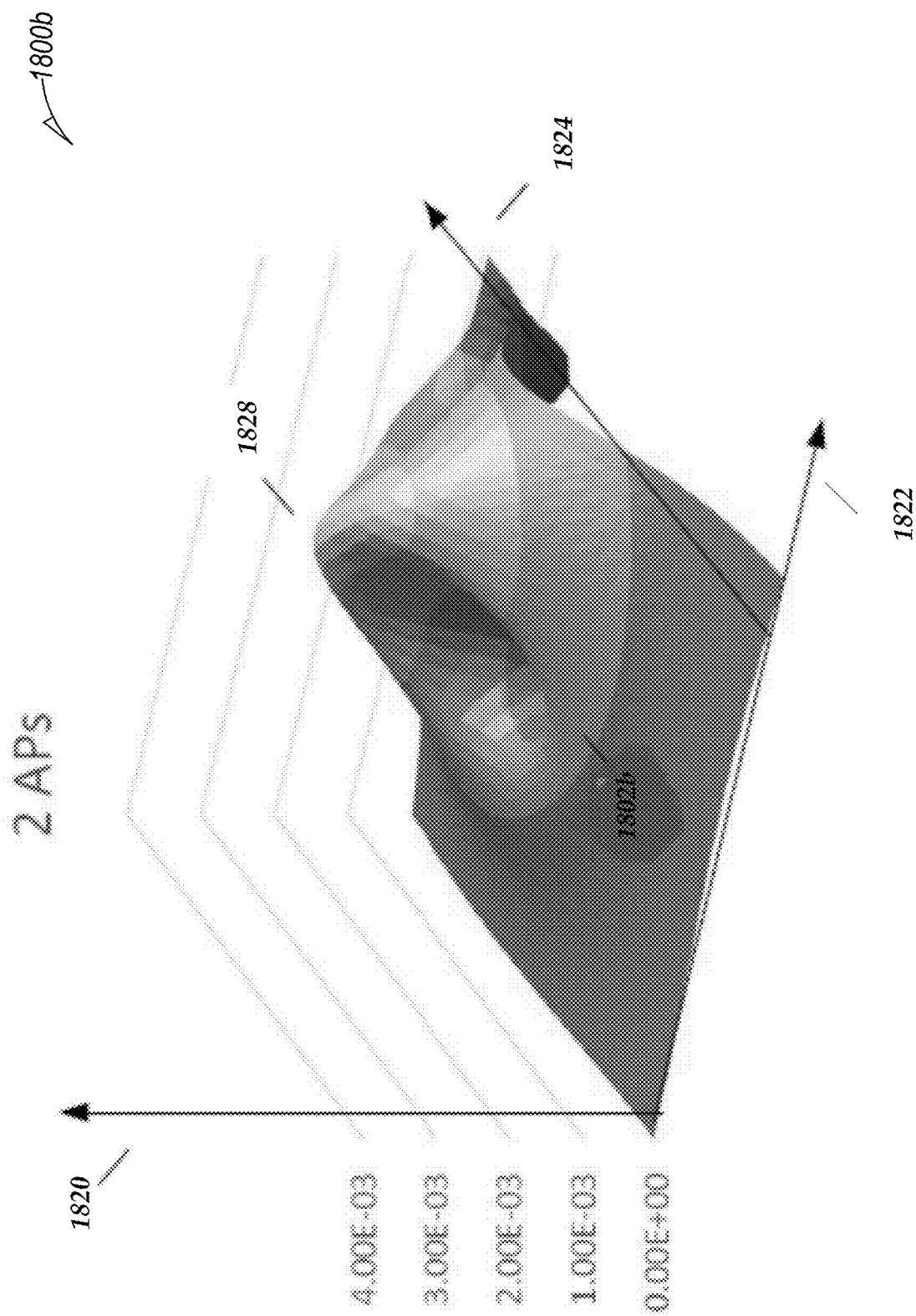

FIG. 18B is a graphical representation 1800*b* of probabilities of an example two-dimensional location probability surface based on received signal strength from two APs. The X axis 1822 and Y axis 1824 define the location or region in which the device is estimated to be located. The Z axis 1820 represents the probability that the device is in the said region or location. The probability surface 1802*b* exhibits a ridge shape. The ridge shape illustrates a peak 1828 of relatively high probability locations for a subject device, with surrounding regions exhibiting lower probabilities. It should be noted that the addition of the second AP increases the probability that a device is in a specific region and as such the probability associated with the peak of the ridge is higher than the probabilities associated with the ring of FIG. 18A.

Figure 18C:
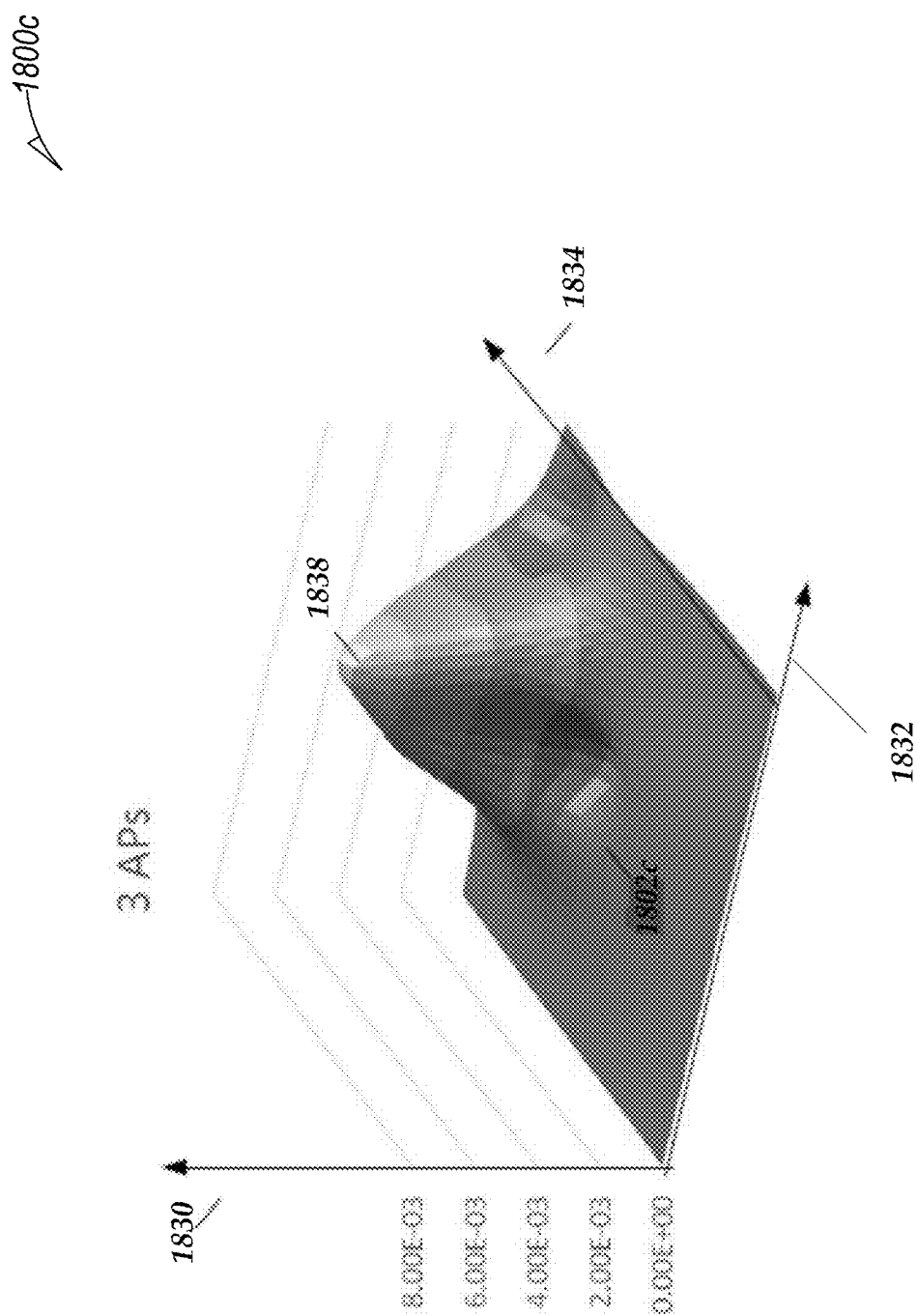

FIG. 18C is a graphical representation 1800*c* of probabilities of an example two-dimensional location probability surface based on received signal strength measurements of signals received from three APs. The X axis 1832 and Y axis 1834 define the location or region in which the device is estimated to be located. The Z axis 1830 represents the probability that the device is in the said region or location. The probability surface 1802*c* exhibits a peak. The peak illustrates a maximum 1838 of relatively high probability locations for a subject device, with surrounding regions exhibiting lower probabilities. It should be noted that the addition of the third AP increases the probability that a device is in a specific region and as such the probability associated with the peak is higher than the probabilities associated with the ridge of FIG. 18B.

Figure 18D:
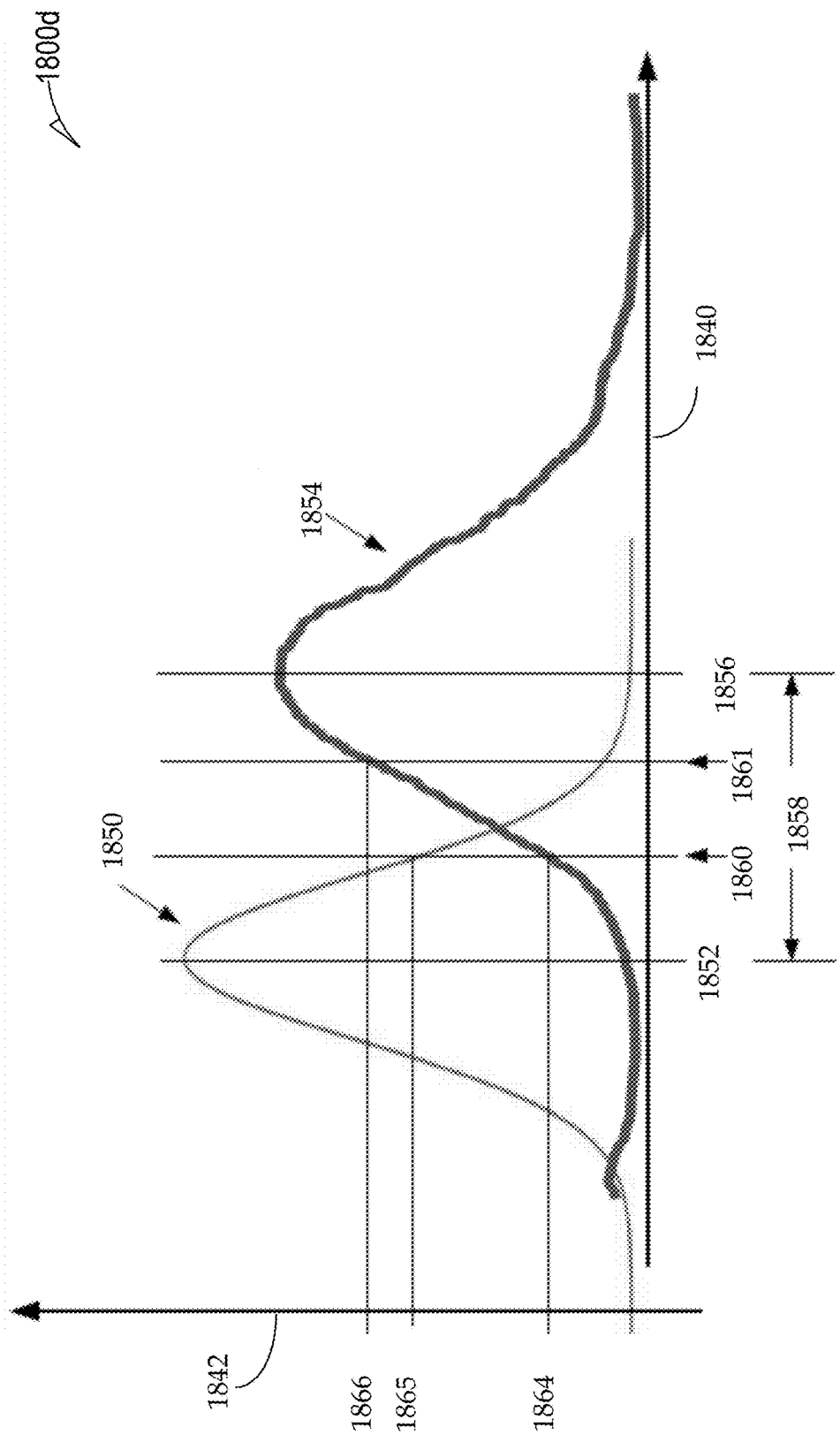
FIG. 18D is a simplified graphical representation of proximity probabilities of an example one-dimensional location probability curves.

FIG. 18D is a simplified graphical representation of proximity probabilities of an example one-dimensional location probability curve. As explained above, a network management system, such as the NMS 110 of FIG. 17, determines, in some embodiments, a location probability surface, such as probability surfaces 1802*a*, 1802*b*, 1802*c* for each one of the wireless devices, such as devices 1706*a*-*c*.

FIG. 18D includes an X axis 1840, and a Y axis 1842. The Y axis 1842 represents a magnitude of a probability that a device is in a location indicated by the X axis 1840. The graph 1800*d* shows a location probability curve 1850 that a first device (e.g. wireless terminal 1706*a* of FIG. 17) is located in a plurality of locations represented by the X axis 1840. The probability peaks at location 1852 and as such the location 1852 is the highest probability location of the first device. A second probability curve 1854 represents probabilities associated with a location of a second device (e.g. wireless terminal 1706*b* of FIG. 17). The second probability curve 1854 peaks at location 1856 and, thus, in some embodiments, the location 1856 is estimated to be the location of the second device.

A distance 1858 represents the distance between the highest probability location 1852 of the first device and the highest probability location 1856 of the second device. In some embodiments, the distance 1858 is compared to a predefined threshold to determine whether the first and second devices are neighbor devices.

FIG. 18D identifies that there is a large area with a probability of the first device being in that area that is non-zero. A probability of the second device being in the proximity of that area is also non-zero. A probability 1861 is shown, representing a probability that the first device is located in location 1860, and a probability 1866 that the second device is located in location 1861, where location 1860 and location 1861 are within a close proximity to each other. Therefore, there is a non-zero probability that the first device and the second device are in close proximity to each other. Not only that the two devices may be in proximity to each other, but there is a non-zero probability that they are at the same location. Specifically, for example, the location probability curve 1850 of the first device indicates that the first device has a probability 1861 of being located at location 1860. The second device has a probability 1864 of being at location 1860. Since both probability 1861 and probability 1864 are non-zero, FIG. 18D illustrates that there is a non-zero probability that the first and second wireless devices are proximate to each other.

Figure 19:
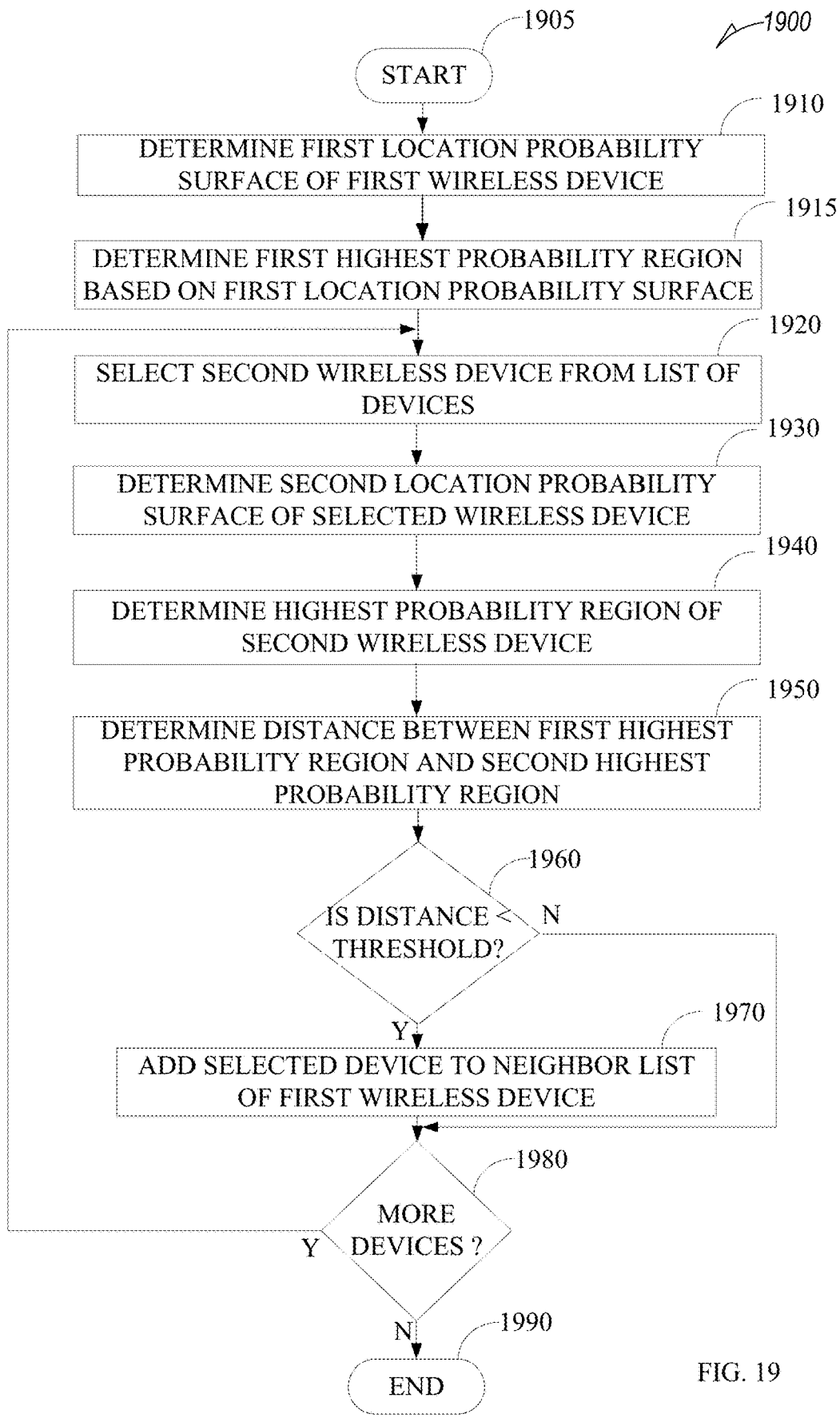
FIG. 19 is a flowchart of an example method for identifying neighbors.

FIG. 19 is a flowchart of a method for identifying neighbor devices. In some embodiments, one or more of the functions discussed below with respect to FIG. 19 and the method 1900 is performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below with respect to FIG. 19.

After start operation 1905, method 1900 moves to operation 1910. In operation 1910, a first location probability surface of a first wireless device is determined. For example, as discussed above, in some embodiments, the first location probability surface includes a plurality of probabilities indicating a probability that the first wireless device is located in a corresponding first plurality of geographic regions. In some embodiments, the probabilities that the first wireless device is located in each of the regions is based on phase differences of signals transmitted by and/or received from the first wireless device. In some embodiments, the probabilities are based on signal strength measurements made by the first wireless device of signals received from a plurality of access points, with the access points being at known locations.

In operation 1915, a first highest probability region is determined from the first location probability surface. The first highest probability region represents a region having a highest probability of the first device location, when compared to other regions of the first plurality of geographic regions.

In operation 1920, a second device is selected from a list of devices. In some embodiments, the list of devices includes devices managed by the NMS 110. For example, the devices include one or more of the wireless terminals 1706a-c in some embodiments.

In operation 1930, a second location probability surface is determined of the selected second wireless device. Similar to the first location probability surface discussed above, the second location probability surface is based on signal strength measurements and/or phase difference measurements associated with the selected (second) wireless device. The second location probability surface specifies probabilities that the second wireless device is located in each of a second plurality of regions.

In operation 1940, a second highest probability region is determined based on the second location probability surface. The second highest probability region represents a region, of the second plurality of regions, that is most likely to include the selected (second) wireless device.

In operation 1950, a distance between the first highest probability region of the first wireless device and the second highest probability region of the selected second device is determined.

Decision operation 1960 evaluates whether the determined distance is below a predefined distance threshold. If the distance is less than the threshold, method 1900 moves to operation 1970, which adds the selected device to a neighbor list of the first wireless device. Otherwise, method 1900 moves from decision operation 1960 to decision operation 1980 without performing operation 1970.

In decision operation 1980, a determination is made as to whether additional devices are to be evaluated with respect to whether any remaining devices are neighbors of the first wireless devices. For example, some embodiments of decision operation 1980 evaluate whether all of the devices in a list of devices maintained by the NMS 110 have been evaluated with respect to the first wireless device and method 1900. If devices remain, method 1900 returns to operation 1920, and a different second wireless device is selected for evaluation. If there are no further devices that need to be evaluated, method 1900 moves from 1980 to end operation 1990.

In some embodiments, method 1900 operates periodically to determine a an updated list of neighbors of the first wireless device. In some embodiments, method 1900 operates for each wireless device managed by the NMS 110 during each iteration. In some embodiments, the periodicity is ten seconds. In some embodiments, each iteration utilizes Equation 20, discussed below, to determine a probability that two devices are located within a predefined distance $T_1$, resulting in a probability time series such as the one described below with respect to FIG. 20.

Figure 20:
FIG. 20 is a graphical representation of an example time series of proximity probabilities and a time series of a composite proximity probability.

FIG. 20 is a graphical representation 2000 of a time series of proximity probabilities and an aggregated proximity probability. Time is shown horizontally with respect to an X axis 420. Four time periods $T_0$, $T_1$, $T_2$, and $T_3$ are shown. Also shown are five different time series, labeled as 2002a-e. Time series 2002a, shown horizontally, represents probabilities that devices D1 and D2 are within a proximity defined by a threshold $Dist_1$, during each of the time periods $T_0$, $T_1$, $T_2$, and $T_3$.

FIG. 20 also illustrates a sliding aggregation window 2040. While the aggregation window 2040 in the illustration include three time periods probabilities, e.g. resulting in an aggregation of probabilities determined during time periods $T_0$, $T_1$, and $T_2$). Other summation window sizes are contemplated.

Some embodiments generate an alert if a first user associated with a wireless device (e.g. D1 in the illustration of FIG. 20), is within a threshold proximity to a second user associated with a second wireless device (e.g. D2 in the illustration of FIG. 20). Some embodiments maintain a risk associated with each of the first and the second users. The risk assessment is then applied along with a probability that the first user was within a proximity of the second user to determine a risk to each user of a contagious disease. For some diseases, e.g., Covid-19, transmission happens only if a first user was in close proximity to a second person, who was identified as relatively high risk, for a time duration longer than a predefined time, e.g., time span of n time periods within the example time series shown in FIG. 20. Some embodiments generate an alert if an aggregation of probabilities within the aggregation window 2040 exceeds a threshold $Thres_2$.

$$\text{Alert}(i) = \text{True}\left(\left(\sum_{k=t-n+1}^{k=t} Pi, j(k)\right) * Pj > Thres_2\right) \quad \text{Eq. 18}$$

where:
Alert (i)=True ( ) indicates that an alert of user i at time t is generated when the term in the brackets is true,
$Thres_2$ a threshold for generating cumulative proximity alert,
Pi,j(k) a probability that user i was in proximity of user j at time k, and $$\left(\sum_{k=t-n+1}^{k=t} Pi, j(k)\right)$$

a sum of probabilities over a sliding summation window of size n,
Pj risk associated with user j (e.g. as indicated in field 2206 discussed below)

Some embodiments compare an aggregation of proximity probabilities within a time series against a predefined threshold. An alert is generated if the aggregated value exceeds the predefined threshold. In some embodiments, the aggregation includes a filter that assesses a cumulative impact over a longer time. In a specific implementation the aggregating filter is a low-pass filter such as:

$$\text{Alert}(i)=\text{True}(O(t)>T_3) \quad \text{Eq. 19a}$$

and $$O(t)=\alpha*Pi,j(t)*Pj+(1-\alpha)*O(t-1) \quad \text{Eq. 19b}$$

where:
Alert (i)=True ( ) alert user i at time t when the term in the brackets is true,
O(t) an output of the low-pass filter at time t,
$T_3$ a threshold for generating cumulative proximity alert,
Pi,j(t) a probability that user i was in proximity of user j at time t.; and
α a coefficient of the low-pass filter, α<1 in some embodiments,
Pj risk associated with a user of device j (e.g. as discussed below with respect to field 2206).

Some embodiments track a relationship between a first wireless device and multiple other wireless devices during a single time period, e.g. such as a single one of the time periods $T_0$, $T_1$, $T_2$, or $T_3$. shown in FIG. 20. For example, some embodiments aggregate probabilities of exposure to multiple devices within a single time period. Appropriate threshold are then applied to these aggregated probabilities within the single time period to determine whether a user associated with the first wireless device is associated with a relatively higher amount of risk. Some embodiments then generate an alert based on this determination.

Referring back to FIG. 17, a risk associated with a first user of wireless terminal 1706a relates, at least in part, to the first user being within a proximity of second and third users of wireless terminals 1706b and 1706c respectively. Thus, being within a relatively close proximity of multiple users within a single time period represents a greater risk than being within the relative close proximity of multiple users during different (non-overlapping) time periods. Further, in some embodiments, a first risk associated with being within a proximity of multiple users during a single time period is greater than a second risk associated with being within a proximity of those multiple users during different time periods.

As illustrated in FIG. 20, multiple time series of probabilities are generated in some embodiments. FIG. 20 shows four time series that indicate a proximity probability of the device D1 with each of other devices D2 (time series 2002a), device D3 (time series 2002b), device D4 (time series 2002c), and device D5 (time series 2002d).

Equation 20 below describes determination of a proximity measurement that two devices are within a distance $T_1$ of each other:

$$P(d(i,j)<T_1) = \Sigma_{all\ k} \Sigma_{all\ k\ \&\ l} (Pi(reg.\ k)*Pj(reg.\ l)) \quad \text{Eq. 20}$$

where:
d(i,j) distance between neighboring devices i and j,
$T_1$ proximity threshold,
k & l indices of regions located within distance $T_1$ (or smaller) to each other,
Pi(reg. k) measure of probability that device i is located in region k,
Pj(reg. l) measure of probability that device j is located in region l,
$P(d(i,j)<T_1)$ measure of probability that distance between device i and j is smaller than the proximity threshold.

Some embodiments determine a probability that a particular first wireless device was proximate to at least one device during a time period according to Equation 21 below:

$$\text{Proximate}_i(t) = 1 - (1-P_{i,j}(t))*(1-P_{i,j+1}(t))* \ldots * (1-P_{i,j+m-1}(t))) \quad \text{Eq. 21}$$

where:
$\text{Proximate}_i(t)$ a measure of probability that device i was proximate to at least one other device during time t
m a number of devices that are neighbors (or some other measure of proximity) of device i (e.g. within a threshold distance of device i),
$P_{i,j}(t)$ a probability that device i was in proximity of device j at time t,
proximity a proximity criterion. E.g. devices are in close proximity when $P_{i,j}(t)$>predefined threshold,
j, ... j+m−1 j through j+m−1 are indices of the m devices in proximity to device i, and
$(1-P_{i,j}(t))$ a probability that devices i and j were not in close proximity at time t.

To assess a cumulative risk introduced by being in close proximity to one or more users, some embodiments enhance Equation 21 by incorporating a risk associated with each of the other devices with which the first wireless device may have been proximate. A risk assessment of the first wireless device (e.g. device i) is thus determined by evaluating Equation 22 below, in at least some embodiments:

$$\text{Risk}(i) = 1-(1-R_j(t)*P_{i,j}(t))*(1-R_{j+1}(t)*P_{i,j+1}(t))* \ldots * (1-R_{j+m-1}(t)*P_{i,j+m-1}(t))) \quad \text{Eq. 22}$$

where:
Risk (i) a measure of risk associated with device i (and its associated user),
Rj (t) risk associated with device j (e.g. and/or its associated user) at time t (e.g. as discussed below with respect to field 2206), and
Other terms As described above with respect to Equation 14.

The risk assessment of Equation 22 is then used, in some embodiments (e.g. via Equation 18) to generate an alert to the user of a device i. In some embodiments, the alert is generated when the condition below evaluates to a true value:

$$\text{Alert}(i) = \text{True}\left(\left(\sum_{k=t-n+1}^{k=t} \text{Risk}\,i(k)\right) > Thres_4\right) \quad \text{Eq. 23}$$

where:
Alert (i)=True ( ) defines a condition under which an alert function alert( ) returns a true value. The alert function receives an input parameter i identifying a user at time t,
$Thres_4$ a threshold for generating a cumulative proximity alert,
Risk i(k) a measure of risk at time k of device i, and $$\left(\sum_{k=t-n+1}^{k=t} \text{Risk}\,i(k)\right)$$

a sum of risks over a sliding summation window of size n.

FIG. 20 shows a time series 2002e of probabilities that a device is proximate to any other device. Each probability in the series is labeled $\text{Prox}_t$ where t is the applicable time period. In some embodiments, each $\text{Prox}_t$ element of the time series 2002e is determined according to Equation 21, discussed above.

The proximity probabilities included in the time series 2002e can be processed by a filter that incorporates a plurality of previous proximity probabilities such as the low-pass filter used in Equation 19a and 19b above. Thus, one embodiment generates an alert according to Equations 24a-b below:

$$\text{Alert}(i) = \text{True}(O(t) > T_5) \quad \text{Eq. 24a}$$

and $$O(t) = \alpha * \text{Proximate}\,i(k) + (1-\alpha)*O(t-1) \quad \text{Eq. 24b}$$

where:
Alert (i)=True ( ) alert user i at time t when the term in the brackets is true,
O(t) output of the low-pass filter at time t,
$T_5$ threshold for generating cumulative proximity alert,
Proximate i(k) probability that device i was in proximity of one or more devices (e.g. see Eq. 21 above), and
α coefficient of the low-pass filter when α<1.

FIG. 20 also shows a time series 2002f. The time series 2002f has elements representing a measure of risk associated with a particular wireless device, and, in some embodiments, by implication, a measure of risk associated with a user of the particular wireless device. In some embodiments, the measure of risk is a measure of infection by COVID-19. In some embodiments, each element of the time series 2002f is determined via Equation 22, discussed above.

Figure 21:
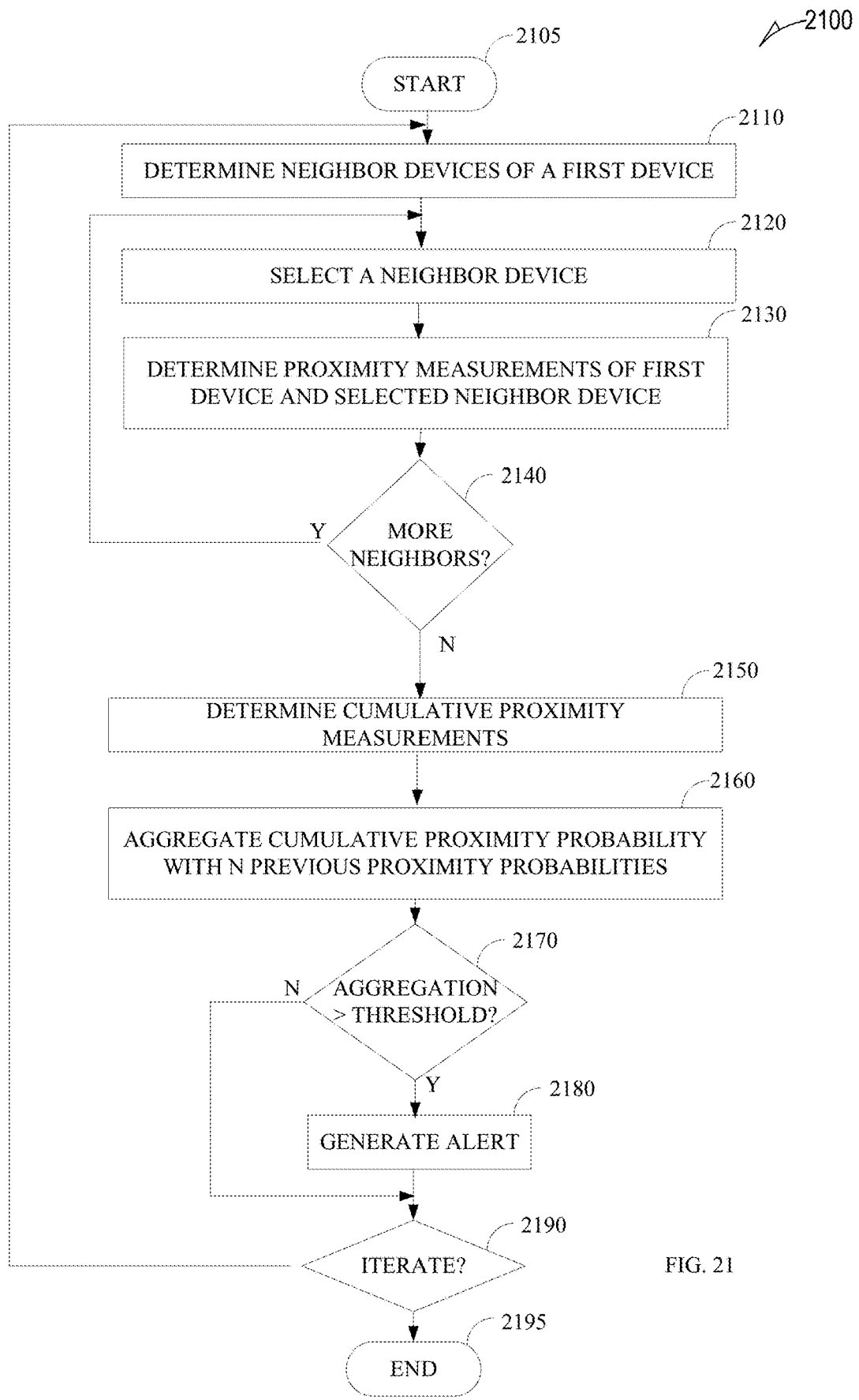
FIG. 21 is a flowchart of an example method of estimating a proximity probability between device and one or more of its neighboring devices.

FIG. 21 is a flowchart of a method for estimating a proximity probability between device and one or more of its neighboring devices. In some embodiments, one or more of the functions discussed below with respect to FIG. 21 and the method 2100 is performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below with respect to FIG. 21.

Method 2100 begins at start operation 2105 and then moves to operation 2110. In operation 2110, neighbor devices of a first wireless device are determined. In some embodiments, operation 2110 operates according to method 1900, discussed above with respect to FIG. 19. Some embodiments consider relationships between the first wireless device and other wireless devices that are not necessarily neighbor devices of the first wireless device.

In operation 2120, a neighbor device is selected from the neighbor devices determined in operation 2110. In operation 2130, a proximity probability of the first device and the selected neighbor device is determined. In some embodiments, the proximity probability is determined according to the discussion of FIG. 20 above, for example, with respect to one or more of the time series 2002a-d.

Decision operation 2140 determines if additional neighbor devices of the first wireless device are to be processed by method 2100. If additional neighbor devices need to be processed (e.g. not all neighbor devices have yet been evaluated by method 2100), the method 2100 moves from decision operation 2140 to operation 2120, where an additional neighbor device is selected. Otherwise, method 2100 moves from decision operation 2140 to operation 2150, which determines a cumulative proximity measurement. In some embodiments, operation 2150 operates consistent with any one or more of the methods discussed above with respect to FIG. 20 above and any of the time series 2002a-e.

In operation 2160, an aggregation of cumulative proximity measurements is determined. For example, in some embodiments, operation 2160 aggregates cumulative proximity probabilities of a device (e.g. device D1 of FIG. 20) within an aggregation window, such as the aggregation window 2040 illustrated above with respect to FIG. 20. In accordance with another example implementation, the aggregation applies a time weighting to the elements of the time series, e.g., using a filter such as the one described with respect to Equation 19 and/or Equations 24a-b above. For example, some embodiments discount less recent elements relative to more recent elements.

Decision operation 2170 determines whether the aggregation determined in operation 2160 is greater than a predefined threshold. If not, method 2100 moves from decision operation 2170 to decision operation 2190. If the aggregation exceeds the threshold, method 2100 moves to operation 2180, which generates an alert based on the aggregation. In some embodiments, the alert utilizes any known messaging technology, such as email, text, social networking based messages, or any other message technology. In some embodiments, the alert is generated to the user of the first wireless device.

Decision operation 2190 determines whether method 2100 should continue to iteratively operate. In some embodiments, the decision or whether to iterate or not is based on whether a shutdown event or a reconfiguration event has been detected. If no further iteration is needed, method 2100 moves to end operation 2195. Otherwise, method 2100 returns to operation 2110. While method 2100 provides an example of an evaluation, with respect to a single first device, whether an aggregation of cumulative proximity probabilities exceeds a threshold, in some embodiments, the method 2100 is performed for a plurality of wireless devices managed by the NMS 110.

Figure 22:
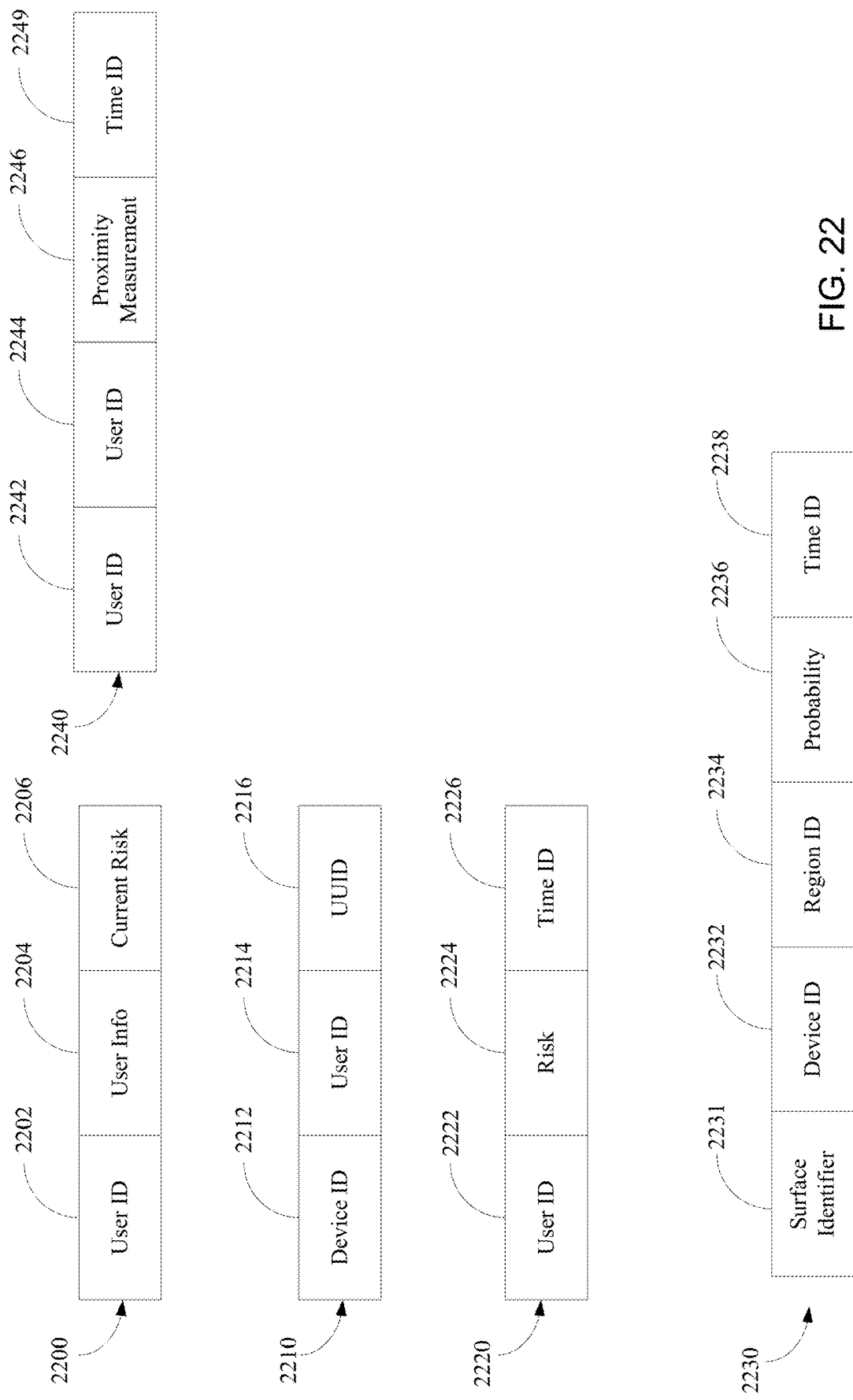
FIG. 22 shows example data structures implemented in one or more of the disclosed embodiments.

FIG. 22 shows example data structures implemented in one or more of the disclosed embodiments. While the example data structures in FIG. 22 are described as relational database tables, the disclosed embodiments contemplate the use of any data structure architecture and FIG. 22 is provided as only one possible implementation.

FIG. 22 shows a user table 2200, device table 2210, risk table 2220, location probability surface table 2230, and a pair table 2240. The user table 2200 includes a user identifier field 2202, user information field 2204, and a current risk field 2206. The user identifier field 2202 uniquely identifies a particular user. The user information field 2204 includes user information for the user. For example, authentication credentials of the user identified via the user identifier field 2202 are stored in the user information field 2204 in some embodiments. The current risk field 2206 stores a current assessment of an infectious disease risk of the user identified by the user identifier field 2202. In some embodiments, a risk associated with a first user is incorporated into a risk assessment of a second user who is determined to be within a proximity of the first user.

The device table 2210 includes a device identifier 2212, a user identifier field 2214, and a unique user identifier field 2216. The device identifier field 2212 uniquely identifies a wireless device, such as any of the wireless terminals 1702a-c of FIG. 17. The user identifier field 2214 identifies a user that is associated with the device identified via field 2212. The user identifier field 2214 is cross referenceable with the user identifier field 2202 in at least some embodiments.

The risk table 2220 includes a user identifier field 2222, risk field 2224, and a time identifier field 2226. The user identifier field 2222 uniquely identifies a user. The user identifier field 2222 is cross referenceable with other user identifier fields, such as the user identifier field 2202, and/or user identifier field 2214. The risk field 2224 identifies a historical risk assessment of the user (identified via field 2222) during a time period identified by the time identifier field 2226. In some embodiments, a moving window of risk assessments is used to determine a user's current risk. For example, in some embodiments, a moving window of risk over a previous fourteen days is used to assess a current risk of a user. Multiple rows in the risk table 2220 for a particular user are used, in some embodiments, to store risk assessments included in the moving window of risk. For example, some embodiments periodically determine risk assessment for one or more users, and store these periodically determined risk assessments in the risk table 2220. Each periodic determination also consults prior risk determinations when determining a "current" risk or a risk for a "current" periodic determination. In some embodiments, operation 2330, discussed below, performs these functions to determine a risk associated with the user.

The location probability surface table 2230 includes a surface identifier field 2231, device identifier field 2232, region identifier field 2234, probability field 2236, and a time identifier field 2238. The surface identifier field 2231 uniquely identifies a particular surface. The device identifier field 2232 uniquely identifies a particular wireless device. The region identifier field 2234 uniquely identifies a particular region in a plurality of regions. In some embodiments, the region identifier field 2234 defines geographic coordinates of a region. The probability field 2236 stores a probability that the device, identified by the device identifier field 2232, is located in the region identified by the region identifier field 2234. The time identifier field 2238 indicates a time period during which the probability is valid. In some embodiments, the time identifier field 2238 identifies which time period of a time series the probability applies. For example, with respect to FIG. 20, the time identifier field 2238 identifies one of $T_0$, $T_1$, $T_2$, or $T_3$. As is common for relational database table implementations, such as the example of FIG. 22, multiple rows in a relational database table, such as the location probability surface table 2230, represent multiple entries in the identified surface. Thus, for example, a location probability surface having a plurality of regions is represented, in some embodiments, via multiple rows of the location probability surface table 2230, a row for each region.

The pair table 2240 stores information relating to pairs of devices. In particular, as discussed above with respect to FIG. 20, some embodiments generate a time series of proximity measurements. An entry in the pair table 2240 stores a single proximity measurement between a pair of devices in some embodiments. The pair table 2240 includes a first device identifier field 2242 and a second device identifier field 2244. Each of the first and second device identifier fields identify devices included in a pair of devices. The proximity measurement field 2246 stores a proximity measurement between the pairs of devices. In some embodiments, the proximity measurement stored in the proximity measurement field 2246 is generated in accordance with any of the methods described above with respect to FIG. 20. The time identifier field 2249 identifies a time period for which the determined proximity measurement of field 2246 is applicable. For example, with reference to FIG. 20, the time identifier field 2249 identifies one of $T_0$, $T_1$, $T_2$, or $T_3$.

Figure 23:
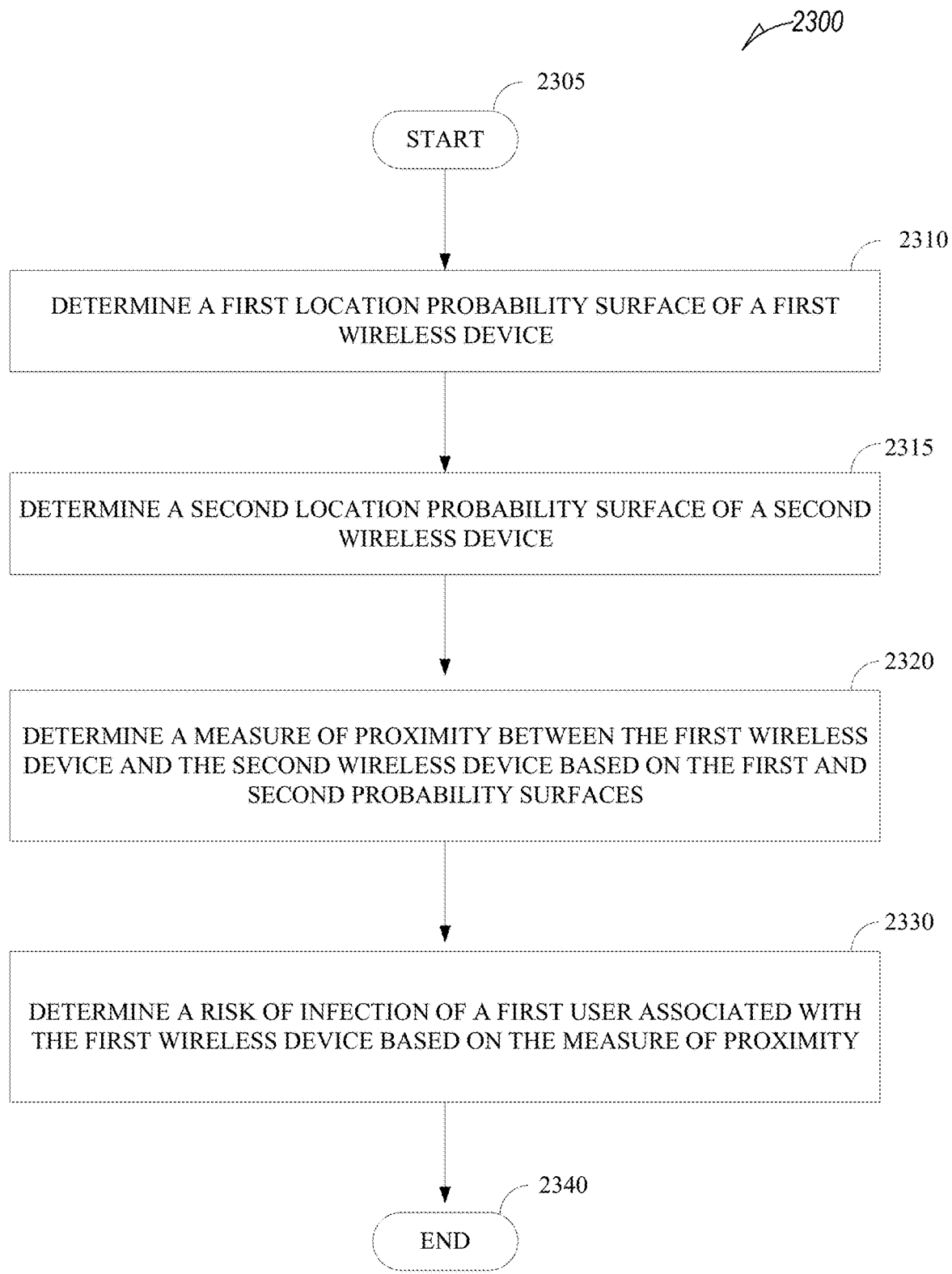
FIG. 23 is a flowchart of an example method for determining a risk of infection.

FIG. 23 is a flowchart of a method for determining a risk of infection of a user. In some embodiments, one or more of the functions discussed below with respect to FIG. 23 and the method 2300 is performed by hardware processing circuitry. For example, in some embodiments, instructions (e.g. 2424 discussed below with respect to FIG. 24) stored in an electronic memory (e.g. 2404 and/or 2406 discussed below with respect to FIG. 24) configure hardware processing circuitry (e.g. 2402 discussed below with respect to FIG. 24) to perform one or more of the functions discussed below with respect to FIG. 23.

After start operation 2305, method 2300 moves to operation 2310. In operation 2310, a first location probability surface of a first wireless device is determined. The first location probability surface is determined, in some embodiments, based on signal strength measurements of signals associated with the first wireless device. In some embodiments, the first wireless device transmits and/or receives the signals upon which the measurements are based. In some embodiments, the first location probability surface is generated in accordance with the data flow described above with respect to FIG. 3. The first location probability surface indicates probabilities that the first wireless device is located in each of a first plurality of regions. In some embodiments, the first location probability surface is based on phase differences of one or more of the signals as received at multiple antennas of a device.

In operation 2315, a second location probability surface of a second wireless device is determined. The second location probability surface is determined, in some embodiments, based on signal strength measurements of signals associated with the second wireless device. In some embodiments, the second wireless device transmits and/or receives the signals upon which the measurements are based. In some embodiments, the second location probability surface is generated in accordance with the data flow described above with respect to FIG. 3. The second location probability surface indicates probabilities that the second wireless device is located in each of a second plurality of regions. In some embodiments, the second location probability surface is based on phase differences of one or more of the signals as received at multiple antennas of a device.

In operation 2320, a measure of proximity between the first wireless device and the second wireless device is determined. The measure of proximity is based on the first and second location probability surfaces. In some embodiments, the measure of proximity aggregates a time series of probability determinations with respect to proximity of the first and second wireless devices. As discussed above, in some embodiments, the aggregation of the time series of proximity determinations utilizes a filter such as the filter discussed above with respect to Equations 19a-b and/or Equation 24. In some embodiments, less recent proximity determinations are discounted relative to more recent proximity determinations.

Some embodiments generate pairs of regions. A first region of the pair identifies a region in the first plurality of regions. A second region in each pair identifies a region in the second plurality of regions. In some embodiments, the pairs of regions that are generated include regions within a predefined threshold distance from each other (pairs of regions further away from each other are not represented by the generated pairs). A first probability that the first wireless device is located in the first region of the pair is then multiplied by a second probability that the second wireless device is located in the second region of the pair. This multiplication is performed for each pair, and the products aggregated. In some embodiments, the measure of proximity is based on the aggregation of the products.

In some embodiments, the measure of proximity is a proximate probability, that is based on a proximity of the first wireless devices to multiple other wireless device including the second wireless device. For example, the proximity probability may further incorporate measures of proximity between the first wireless device and a third, fourth and/or fifth wireless device. In some embodiments, the proximate probability indicates a probability that the first wireless device is proximate to at least one other device.

In some embodiments, method 2300 determines a highest probability location of the first wireless device and a second highest probability location of the second wireless device. The highest probability location of the first wireless device, in some embodiments, is a region having a highest associated probability as defined by the first location probability surface. The highest probability location of the second wireless device, in some embodiments, is a second region having a highest associated probability as defined by the second location probability surface. In some embodiments, the determination of the measure of proximity is based on whether the highest probability location of the first wireless device and the highest probability location of the second wireless device are within a predefined distance threshold of each other. For example, some embodiments first screen pairs of devices based on their highest probability locations (e.g. regions). For example, as discussed above with respect to FIG. 19, if a distance between the highest probability locations of two devices is less than a distance threshold, the devices are considered neighbors. If devices are not considered neighbors, then measures of proximity between the two devices are not determined, for example, in operation 2320. In this case, operation 2330 also does not operate with respect to these pairs of devices, at least in some embodiments.

In operation 2330, a first risk of infection of a first user associated with the first wireless device is determined. In some embodiments, the first user is identified via a device table, such as the device table 2210 discussed above with respect to FIG. 22. In some embodiments, the first risk of infection is further based on a second risk associated with a second user. The second user is associated with the second wireless device. In some embodiments, the first risk is further based on a prior assessment of risk of the first user (e.g. a third risk). Some embodiments determine the first risk according to Equation 22, discussed above. Some embodiments consider risk associated with a plurality of different users beyond the first user and second user discussed above. For example, if the first user was within a predefined threshold proximity of 5, 10, 20 or 50 users, or any number in between, risk associated with each of those users is also considered in the determination of the first risk. Each of the risks of each of these users is discounted, according to Equation 22 in some embodiments, based on a probability that the first user was within a distance of the respective user, with the probability derived from location probability surfaces of the first user and the respective user.

Some embodiments generate an alert based on the first risk of infection. For example, some embodiments generate an email, text message, or other message if the first risk is above a predefined threshold risk level. Some embodiments generate the alert according to Equations 23a and/or 23b, and/or Equations 24a and/or 24b, discussed above.

Some embodiments of method 2300 operate iteratively, and thus generate a time series of measures of proximity between the first wireless and second wireless device, and/or other additional wireless devices. In some embodiments, a risk associated with a user of the first wireless device is also iteratively determined in these embodiments. Thus, a time series of risk assessments of a user of the first wireless device is then generated by the iterative performance of method 2300. For example, FIG. 20, and in particular, time series 2002e, demonstrates periodic or iterative performance of method 2300 so as to generate a time series of proximity determinations. Time series 2002f also demonstrates periodic or iterative performance of method 2300 so as to generate a time series of risk determinations. Note that in some embodiments, method 2300 generates the time series of risk determinations based on corresponding time series of probability measurement determinations with respect to one or more other wireless devices. For example, some embodiments determine a risk associated with the first user at time $T_0$ based on one or more of a proximity determination between the first wireless device and a second wireless device at time $T_0$ (e.g. analogous the $P_{OD_1D_2}$ in FIG. 20), a proximity determination between the first wireless device and a third wireless device at time $T_0$ (e.g. analogous the $P_{OD_1D_3}$ in FIG. 20), a proximity determination between the first wireless device and a fourth wireless device at time $T_0$ (e.g. analogous the $P_{OD_1D_4}$ in FIG. 20). Analogous risk determinations are then made for the first user in periodic time periods, as illustrated in FIG. 20 with respect to time periods $T_1$, $T_2$, and $T_3$.

Thus, in some embodiments, time series of measurements are generated periodically or at least during a plurality of non-overlapping time periods. Some embodiments then aggregate these measures of proximity across the time series (e.g. time series 2002e). Thus, for example, a time series of measures of proximity between the first wireless device and a second wireless device are aggregated in some embodiments. A second time series of measures of proximity between the first wireless device and a third wireless device are aggregated in some embodiments. In some embodiments, corresponding measures in the first and second time series are aggregated to generate a time series of proximate measures of probability, as discussed above (e.g. Equation 21). After operation 2330 completes, method 2300 moves to end operation 2340.

Figure 24:
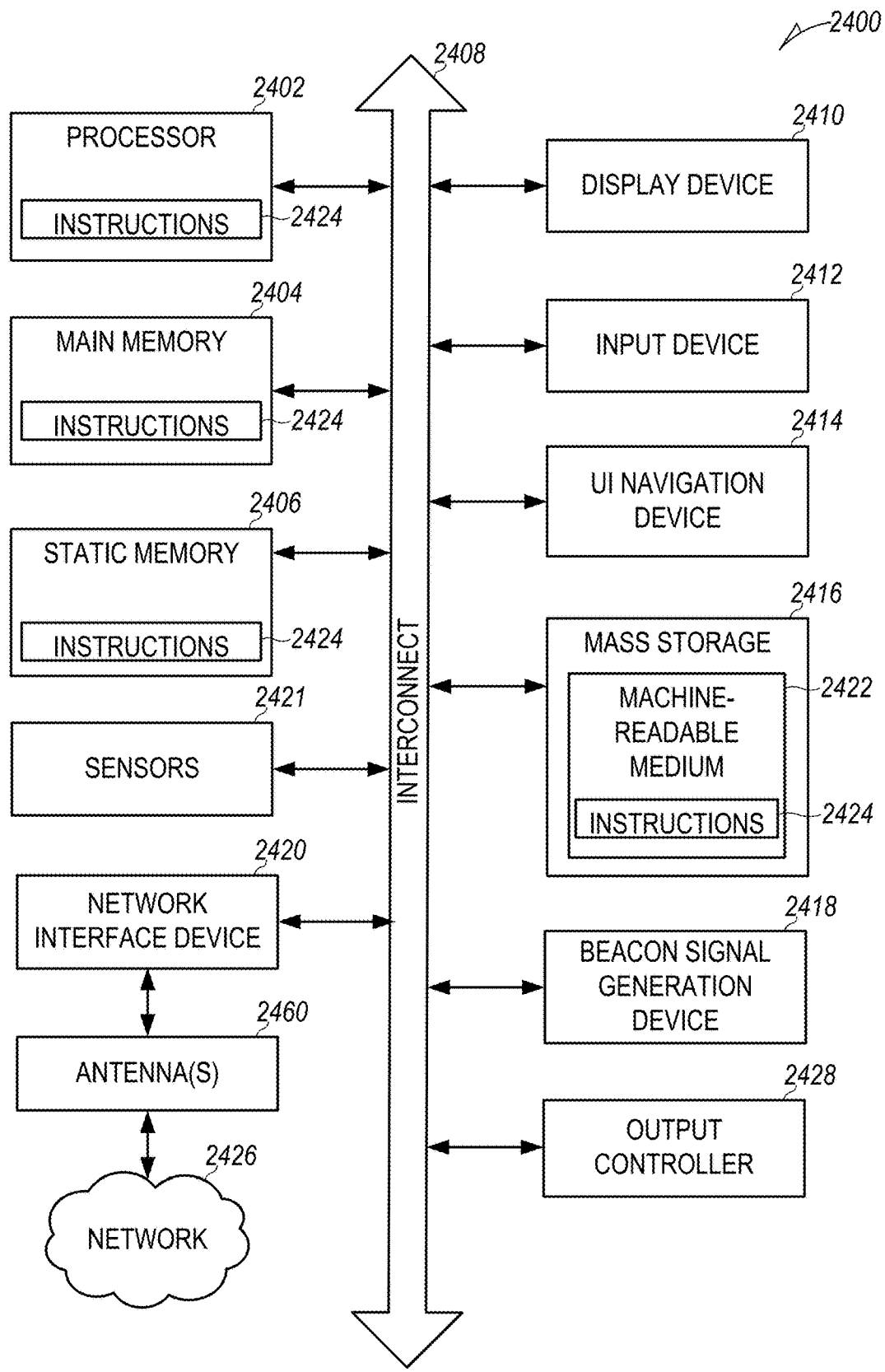
FIG. 24 illustrates a block diagram of an example machine upon which any one or more of the techniques (e.g., methodologies) discussed herein may be performed.

FIG. 24 illustrates a block diagram of an example machine 2400 upon which any one or more of the techniques (e.g., methodologies) discussed herein may perform. Machine 2400 (e.g., computer system) may include a hardware processor 2402 (e.g., a central processing unit (CPU), a graphics processing unit (GPU), a hardware processor core, or any combination thereof), a main memory 2404 and a static memory 2406, some or all of which may communicate with each other via an interlink 2408 (e.g., bus).

Specific examples of main memory 2404 include Random Access Memory (RAM), and semiconductor memory devices, which may include, in some embodiments, storage locations in semiconductors such as registers. Specific examples of static memory 2406 include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; RAM; and CD-ROM and DVD-ROM disks.

The machine 2400 may further include a display device 2410, an input device 2412 (e.g., a keyboard), and a user interface (UI) navigation device 2414 (e.g., a mouse). In an example, the display device 2410, input device 2412 and UI navigation device 2414 may be a touch screen display. The machine 2400 may additionally include a mass storage device (e.g., drive unit) 2416, a beacon signal generation device 2418, a network interface device 2420, and one or more sensors 2421, such as a global positioning system (GPS) sensor, compass, accelerometer, or other sensor. The machine 2400 may include an output controller 2428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.). In some embodiments the hardware processor 2402 and/or instructions 2424 may comprise processing circuitry and/or transceiver circuitry.

The mass storage device 2416 may include a machine readable medium 2422 on which is stored one or more sets of data structures or instructions 2424 (e.g., software) embodying or utilized by any one or more of the techniques or functions described herein. The machine readable medium 2422 is a non-transitory computer readable storage medium in at least some embodiments. The instructions 2424 may also reside, completely or at least partially, within the main memory 2404, within static memory 2406, or within the hardware processor 2402 during execution thereof by the machine 2400. In an example, one or any combination of the hardware processor 2402, the main memory 2404, the static memory 2406, or the mass storage device 2416 may constitute machine readable media.

Specific examples of machine-readable media may include: non-volatile memory, such as semiconductor memory devices (e.g., EPROM or EEPROM) and flash memory devices; magnetic disks, such as internal hard disks and removable disks; magneto-optical disks; RAM; and CD-ROM and DVD-ROM disks.

While the machine readable medium 2422 is illustrated as a single medium, the term "machine readable medium" may include a single medium or multiple media (e.g., a centralized or distributed database, and/or associated caches and servers) configured to store the instructions 2424.

An apparatus of the machine 2400 may be one or more of a hardware processor 2402 (e.g., a central processing unit (CPU), a graphics processing unit (GPU), a hardware processor core, or any combination thereof), one or more hardware memories, including one or more of a main memory 2404 and a static memory 2406. The apparatus of the machine 2400 also includes, in some embodiments, one or more sensors 2421, network interface device 2420, one or more antennas 2460, a display device 2410, an input device 2412, a UI navigation device 2414, a mass storage device 2416, instructions 2424, a beacon signal generation device 2418, and an output controller 2428. The apparatus may be configured to perform one or more of the methods and/or operations disclosed herein. The apparatus may be intended as a component of the machine 2400 to perform one or more of the methods and/or operations disclosed herein, and/or to perform a portion of one or more of the methods and/or operations disclosed herein. In some embodiments, the apparatus may include a pin or other means to receive power. In some embodiments, the apparatus may include power conditioning hardware.

The term "machine readable medium" may include any medium that is capable of storing, encoding, or carrying instructions for execution by the machine 2400 and that cause the machine 2400 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); and CD-ROM and DVD-ROM disks. In some examples, machine readable media may include non-transitory machine readable media. In some examples, machine readable media may include machine readable media that is not a transitory propagating signal.

The instructions 2424 may further be transmitted or received over a communications network 2426 using a transmission medium via the network interface device 2420 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others.

In an example, the network interface device 2420 may include one or more physical jacks (e.g., Ethernet, coaxial, or phone jacks) or one or more antennas to connect to the communications network 2426. In an example, the network interface device 2420 may include one or more antennas 2460 to wirelessly communicate using at least one of single-input multiple-output (SIMO), multiple-input multiple-output (MIMO), or multiple-input single-output (MISO) techniques. In some examples, the network interface device 2420 may wirelessly communicate using Multiple User MIMO techniques. The term "transmission medium" shall be taken to include any intangible medium that is capable of storing, encoding or carrying instructions for execution by the machine 2400, and includes digital or analog communications signals or other intangible medium to facilitate communication of such software.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

The techniques of various embodiments may be implemented using software, hardware and/or a combination of software and hardware. Various embodiments are directed to apparatus, e.g., management entities, e.g., a network monitoring node, routers, gateways, switches, access points, DHCP servers, DNS servers, AAA servers, user equipment devices, e.g., wireless nodes such as mobile wireless terminals, base stations, communications networks, and communications systems. Various embodiments are also directed to methods, e.g., method of controlling and/or operating a communications device or devices, e.g., a network management node, an access point, wireless terminals (WT), user equipment (UEs), base stations, control nodes, DHCP nodes, DNS servers, AAA nodes, Mobility Management Entities (MMEs), networks, and/or communications systems. Various embodiments are also directed to non-transitory machine, e.g., computer, readable medium, e.g., ROM, RAM, CDs, hard discs, etc., which include machine readable instructions for controlling a machine to implement one or more steps of a method.

It is understood that the specific order or hierarchy of steps in the processes disclosed are provided as example approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

In various embodiments devices and nodes described herein are implemented using one or more modules to perform the steps corresponding to one or more methods, for example, signal generation, transmitting, processing, analyzing, and/or receiving steps. Thus, in some embodiments various features are implemented using modules. Such modules may be implemented using software, hardware or a combination of software and hardware. In some embodiments each module is implemented as an individual circuit with the device or system including a separate circuit for implementing the function corresponding to each described module. Many of the above described methods or method steps can be implemented using machine executable instructions, such as software, included in a machine readable medium such as a memory device, e.g., RAM, floppy disk, etc. to control a machine, e.g., general purpose computer with or without additional hardware, to implement all or portions of the above described methods, e.g., in one or more nodes. Accordingly, among other things, various embodiments are directed to a machine-readable medium e.g., a non-transitory computer readable medium, including machine executable instructions for causing a machine, e.g., processor and associated hardware, to perform one or more of the steps of the above-described method(s). Some embodiments are directed to a device including a processor configured to implement one, multiple or all of the operations of the disclosed embodiments.

In some embodiments, the processor or processors, e.g., CPUs, of one or more devices, e.g., communications devices such as routers, switches, network attached servers, network management nodes, wireless terminals (UEs), and/or access nodes, are configured to perform the steps of the methods described as being performed by the devices. The configuration of the processor may be achieved by using one or more modules, e.g., software modules, to control processor configuration and/or by including hardware in the processor, e.g., hardware modules, to perform the recited steps and/or control processor configuration. Accordingly, some but not all embodiments are directed to a communications device, e.g., user equipment, with a processor which includes a module corresponding to each of the steps of the various described methods performed by the device in which the processor is included. In some but not all embodiments a communications device includes a module corresponding to each of the steps of the various described methods performed by the device in which the processor is included. The modules may be implemented purely in hardware, e.g., as circuits, or may be implemented using software and/or hardware or a combination of software and hardware.

Some embodiments are directed to a computer program product comprising a computer-readable medium comprising code for causing a computer, or multiple computers, to implement various functions, steps, acts and/or operations, e.g. one or more steps described above. Depending on the embodiment, the computer program product can, and sometimes does, include different code for each step to be performed. Thus, the computer program product may, and sometimes does, include code for each individual step of a method, e.g., a method of operating a communications device, e.g., a network management node, an access point, a base station, a wireless terminal or node. The code may be in the form of machine, e.g., computer, executable instructions stored on a computer-readable medium such as a RAM (Random Access Memory), ROM (Read Only Memory) or other type of storage device. In addition to being directed to a computer program product, some embodiments are directed to a processor configured to implement one or more of the various functions, steps, acts and/or operations of one or more methods described above. Accordingly, some embodiments are directed to a processor, e.g., CPU, configured to implement some or all of the steps of the methods described herein. The processor may be for use in, e.g., a communications device or other device described in the present application.

While described in the context of a communications system including wired, optical, cellular, Wi-Fi, Bluetooth and BLE, at least some of the methods and apparatus of various embodiments are applicable to a wide range of communications systems including IP and non IP based, OFDM and non-OFDM and/or non-cellular systems.

Numerous additional variations on the methods and apparatus of the various embodiments described above will be apparent to those skilled in the art in view of the above description. Such variations are to be considered within the scope. The methods and apparatus may be, and in various embodiments are, used with IP based and non-IP, wired and wireless such CDMA, orthogonal frequency division multiplexing (OFDM), Wi-Fi, Bluetooth, BLE, optical and/or various other types of communications techniques which may be used to provide communications links between network attached or associated devices or other devices including receiver/transmitter circuits and logic and/or routines, for implementing the methods.

Example 1 is a method performed by hardware processing circuitry, comprising: determining, based on wireless signals associated with a first wireless device, a first location probability surface, the first location probability surface defining a first plurality of probabilities that the first wireless device is located in a first plurality of corresponding regions; determining, based on wireless signals associated with a second wireless device, a second location probability surface, the second probability surface defining a second plurality of probabilities that the second wireless device is located in a second plurality of corresponding regions; multiplying a first probability associated with a first region of the first plurality of regions with a second probability associated with a second region of the second plurality of regions; determining, based on the multiplying, a third probability that the first wireless device and the second wireless device are within a threshold distance of each other; determining a measure of proximity between the first wireless device and the second wireless device based on the third probability; and determining a first risk of infection of a first user associated with the first wireless device based on the measure of proximity.

In Example 2, the subject matter of Example 1 optionally includes generating an alert based on the first risk.

In Example 3, the subject matter of any one or more of Examples 1-2 optionally include obtaining a second risk of infection of a second user associated with the second wireless device, wherein the determining of the risk of infection of the first user is based on the second risk.

In Example 4, the subject matter of any one or more of Examples 1-3 optionally include determining a third risk of infection of the first user over a plurality of time periods, wherein the first risk is based on the third risk.

In Example 5, the subject matter of any one or more of Examples 1-4 optionally include determining a highest probability first geographic location of the first wireless device based on the first location probability surface; determining a highest probability second geographic location of the second wireless device based on the second location probability surface; and determining a geographic distance between the highest probability first geographic location and the highest probability second geographic location, wherein the determining of the measure of proximity is in response to the geographic distance.

In Example 6, the subject matter of any one or more of Examples 1-5 optionally include determining pairs of regions, each pair including a first region of the first plurality of regions and a second region of the second plurality of regions, the pairs determined such that a distance between the first region and the second region is less than a predefined threshold distance; for each pair of regions: determining, based on the first location probability surface, a first probability that the first wireless device is located in the first region, determining, based on the second location probability surface, a second probability that the second wireless device is located in the second region, multiplying the first probability and the second probability, and determining a product of the pair based on the multiplying; and first aggregating the products of the pairs, wherein the determining of the measure of proximity is based on the first aggregation.

Example 7 is a system, comprising: hardware processing circuitry; and one or more hardware memories storing instructions that when executed configure the hardware processing circuitry to perform operations comprising: determining, based on wireless signals associated with a first wireless device, a first location probability surface, the first location probability surface defining a first plurality of probabilities that the first wireless device is located in a first plurality of corresponding regions; determining, based on wireless signals associated with a second wireless device, a second location probability surface, the second probability surface defining a second plurality of probabilities that the second wireless device is located in a second plurality of corresponding regions; multiplying a first probability associated with a first region of the first plurality of regions with a second probability associated with a second region of the second plurality of regions; determining, based on the multiplying, a third probability that the first wireless device and the second wireless device are within a threshold distance of each other; determining, a measure of proximity between the first wireless device and the second wireless device based on the third probability; and determining a first risk of infection of a first user associated with the first wireless device based on the measure of proximity.

In Example 8, the subject matter of Example 7 optionally includes the operations further comprising generating an alert based on the first risk.

In Example 9, the subject matter of any one or more of Examples 7-8 optionally include the operations further comprising obtaining a second risk of infection of a second user associated with the second wireless device, wherein the determining of the risk of infection of the first user is based on the second risk.

In Example 10, the subject matter of any one or more of Examples 7-9 optionally include the operations further comprising determining a third risk of infection of the first user over a plurality of time periods, wherein the first risk is based on the third risk.

In Example 11, the subject matter of any one or more of Examples 7-10 optionally include the operations further comprising: determining a highest probability first geographic location of the first wireless device based on the first location probability surface; determining a highest probability second geographic location of the second wireless device based on the second location probability surface; and determining a geographic distance between the highest probability first geographic location and the highest probability second geographic location, wherein the determining of the measure of proximity is in response to the geographic distance.

In Example 12, the subject matter of Example 11 optionally includes the operations further comprising determining the distance is below a predefined second threshold distance, wherein the determining of the measure of proximity is in response to the determining.

In Example 13, the subject matter of any one or more of Examples 7-12 optionally include the operations further comprising obtaining first phase differences of signals associated with the first wireless device, wherein the first location probability surface is based on the first phase differences.

In Example 14, the subject matter of any one or more of Examples 7-13 optionally include the operations further comprising obtaining RSSI measurements of signals associated with the first wireless device, wherein the determining of the first location probability surface is based on the RSSI measurements.

In Example 15, the subject matter of any one or more of Examples 7-14 optionally include the operations further comprising: periodically determining the probability that the first wireless device is in the first region and the second wireless device is in the second region; and aggregating the periodic probability determinations, wherein the measure of proximity is in response to the aggregating.

In Example 16, the subject matter of Example 15 optionally includes wherein the aggregating includes discounting less recent probability determinations relative to more recent probability determinations.

In Example 17, the subject matter of any one or more of Examples 7-16 optionally include the operations further comprising: determining pairs of regions, each pair including a first region of the first plurality of regions and a second region of the second plurality of regions, the pairs determined such that a distance between the first region and the second region is less than a predefined threshold distance; for each pair of regions: determining, based on the first location probability surface, a first probability that the first wireless device is located in the first region, determining, based on the second location probability surface, a second probability that the second wireless device is located in the second region, multiplying the first probability and the second probability, and determining a product of the pair based on the multiplying; and first aggregating the products of the pairs, wherein the determining of the measure of proximity is based on the first aggregation.

In Example 18, the subject matter of Example 17 optionally includes the operations further comprising: determining a third location probability surface based on third signal strength measurements associated with a third wireless device, the third probability surface defining a third plurality of probabilities that the third wireless device is located in a third plurality of corresponding regions; determining a first region of the first plurality of regions is within the predefined threshold distance of a third region of the third plurality of regions; determining a fourth probability that the first wireless device is in the first region and the third wireless device is in the second region, and wherein the determining of the measure of proximity is further based on the fourth probability.

In Example 19, the subject matter of any one or more of Examples 17-18 optionally include the operations further comprising: determining second pairs of regions, each second pair including a first region of the first plurality of regions and a third region of the third plurality of regions, the second pairs determined such that a distance between the first region and the third region is less than a predefined threshold distance; for each second pair of regions: determining, based on the first location probability surface, a first probability that the first wireless device is located in the first region, determining, based on the third location probability surface, a third probability that the third wireless device is located in the third region, multiplying the first probability and the third probability, and determining a second product of the second pair based on the multiplying; second aggregating the second products of the pairs; and wherein the determining of the measure of proximity is based on the first aggregation and the second aggregation.

Example 20 is a non-transitory computer readable storage medium storing instructions that when executed configure hardware processing circuitry to perform operations comprising: determining based on wireless signals associated with a first wireless device, a first location probability surface, the first location probability surface defining a first plurality of probabilities that the first wireless device is located in a first plurality of corresponding regions; determining, based on wireless signals associated with a second wireless device, a second location probability surface, the second probability surface defining a second plurality of probabilities that the second wireless device is located in a second plurality of corresponding regions; multiplying a first probability associated with a first region of the first plurality of regions with a second probability associated with a second region of the second plurality of regions; determining a third probability that the first wireless device and the second wireless device are within a threshold distance of each other; determining a measure of proximity between the first wireless device and the second wireless device based on the third probability; and determining a first risk of infection of a first user associated with the first wireless device based on the measure of proximity.

Although the discussion above describes, in some instances, determining location of a wireless terminal in a two-dimensional space, the features described above may be applied equally to locating a wireless terminal in a three-dimensional space. As such, in a three-dimensional space, rather than determining a location of a WT in a specific cell or region, some of the disclosed embodiments determine a location of a WT within a three-dimensional region when considering a plurality of three-dimensional regions.

The invention claimed is:

1. A method performed by hardware processing circuitry, comprising:
    determining, based on wireless signals associated with a first wireless device, a first location probability surface, the first location probability surface defining a first plurality of probabilities that the first wireless device is located in a first plurality of corresponding regions;
    determining, based on wireless signals associated with a second wireless device, a second location probability surface, the second probability surface defining a second plurality of probabilities that the second wireless device is located in a second plurality of corresponding regions;
    multiplying a first probability associated with a first region of the first plurality of regions with a second probability associated with a second region of the second plurality of regions;
    determining, based on the multiplying, a third probability that the first wireless device and the second wireless device are within a threshold distance of each other;
    determining a measure of proximity between the first wireless device and the second wireless device based on the third probability; and
    determining a first risk of infection of a first user associated with the first wireless device based on the measure of proximity.

2. The method of claim 1, further comprising generating an alert based on the first risk.

3. The method of claim 1, further comprising obtaining a second risk of infection of a second user associated with the second wireless device, wherein the determining of the risk of infection of the first user is based on the second risk.

4. The method of claim 1, further comprising determining a third risk of infection of the first user over a plurality of time periods, wherein the first risk is based on the third risk.

5. The method of claim 1, further comprising:
    determining a highest probability first geographic location of the first wireless device based on the first location probability surface;
    determining a highest probability second geographic location of the second wireless device based on the second location probability surface; and
    determining a geographic distance between the highest probability first geographic location and the highest probability second geographic location, wherein the determining of the measure of proximity is in response to the geographic distance.

6. The method of claim 1, further comprising:
    determining pairs of regions, each pair including a first region of the first plurality of regions and a second region of the second plurality of regions, the pairs determined such that a distance between the first region and the second region is less than a predefined threshold distance;
    for each pair of regions:
        determining, based on the first location probability surface, a first probability that the first wireless device is located in the first region,
        determining, based on the second location probability surface, a second probability that the second wireless device is located in the second region,
        multiplying the first probability and the second probability, and
        determining a product of the pair based on the multiplying; and
    first aggregating the products of the pairs, wherein the determining of the measure of proximity is based on the first aggregation.

7. A system, comprising:
    hardware processing circuitry; and
    one or more hardware memories storing instructions that when executed configure the hardware processing circuitry to perform operations comprising:
        determining, based on wireless signals associated with a first wireless device, a first location probability surface, the first location probability surface defining a first plurality of probabilities that the first wireless device is located in a first plurality of corresponding regions;
        determining, based on wireless signals associated with a second wireless device, a second location probability surface, the second probability surface defining a second plurality of probabilities that the second wireless device is located in a second plurality of corresponding regions;

multiplying a first probability associated with a first region of the first plurality of regions with a second probability associated with a second region of the second plurality of regions;

determining, based on the multiplying, a third probability that the first wireless device and the second wireless device are within a threshold distance of each other;

determining, a measure of proximity between the first wireless device and the second wireless device based on the third probability; and determining a first risk of infection of a first user associated with the first wireless device based on the measure of proximity.

8. The system of claim 7, the operations further comprising generating an alert based on the first risk.

9. The system of claim 7, the operations further comprising obtaining a second risk of infection of a second user associated with the second wireless device, wherein the determining of the risk of infection of the first user is based on the second risk.

10. The system of claim 7, the operations further comprising determining a third risk of infection of the first user over a plurality of time periods, wherein the first risk is based on the third risk.

11. The system of claim 7, the operations further comprising:

determining a highest probability first geographic location of the first wireless device based on the first location probability surface;

determining a highest probability second geographic location of the second wireless device based on the second location probability surface; and determining a geographic distance between the highest probability first geographic location and the highest probability second geographic location, wherein the determining of the measure of proximity is in response to the geographic distance.

12. The system of claim 11, the operations further comprising determining the distance is below a predefined second threshold distance, wherein the determining of the measure of proximity is in response to the determining.

13. The system of claim 7, the operations further comprising obtaining first phase differences of signals associated with the first wireless device, wherein the first location probability surface is based on the first phase differences.

14. The system of claim 7, the operations further comprising obtaining RSSI measurements of signals associated with the first wireless device, wherein the determining of the first location probability surface is based on the RSSI measurements.

15. The system of claim 7, the operations further comprising:

periodically determining the probability that the first wireless device is in the first region and the second wireless device is in the second region; and aggregating the periodic probability determinations, wherein the measure of proximity is in response to the aggregating.

16. The system of claim 15, wherein the aggregating includes discounting less recent probability determinations relative to more recent probability determinations.

17. The system of claim 7, the operations further comprising:

determining pairs of regions, each pair including a first region of the first plurality of regions and a second region of the second plurality of regions, the pairs determined such that a distance between the first region and the second region is less than a predefined threshold distance;

for each pair of regions:
determining, based on the first location probability surface, a first probability that the first wireless device is located in the first region,
determining, based on the second location probability surface, a second probability that the second wireless device is located in the second region,
multiplying the first probability and the second probability, and
determining a product of the pair based on the multiplying; and first aggregating the products of the pairs, wherein the determining of the measure of proximity is based on the first aggregation.

18. The system of claim 17, the operations further comprising:

determining a third location probability surface based on third signal strength measurements associated with a third wireless device, the third probability surface defining a third plurality of probabilities that the third wireless device is located in a third plurality of corresponding regions;

determining a first region of the first plurality of regions is within the predefined threshold distance of a third region of the third plurality of regions;

determining a fourth probability that the first wireless device is in the first region and the third wireless device is in the second region, and wherein the determining of the measure of proximity is further based on the fourth probability.

19. The system of claim 17, the operations further comprising:

determining second pairs of regions, each second pair including a first region of the first plurality of regions and a third region of the third plurality of regions, the second pairs determined such that a distance between the first region and the third region is less than a predefined threshold distance;

for each second pair of regions:
determining, based on the first location probability surface, a first probability that the first wireless device is located in the first region,
determining, based on the third location probability surface, a third probability that the third wireless device is located in the third region,
multiplying the first probability and the third probability, and
determining a second product of the second pair based on the multiplying;

second aggregating the second products of the pairs; and wherein the determining of the measure of proximity is based on the first aggregation and the second aggregation.

20. A non-transitory computer readable storage medium storing instructions that when executed configure hardware processing circuitry to perform operations comprising:

determining based on wireless signals associated with a first wireless device, a first location probability surface, the first location probability surface defining a first plurality of probabilities that the first wireless device is located in a first plurality of corresponding regions;

determining, based on wireless signals associated with a second wireless device, a second location probability surface, the second probability surface defining a second plurality of probabilities that the second wireless device is located in a second plurality of corresponding regions;

multiplying a first probability associated with a first region of the first plurality of regions with a second probability associated with a second region of the second plurality of regions;

determining a third probability that the first wireless device and the second wireless device are within a threshold distance of each other;

determining a measure of proximity between the first wireless device and the second wireless device based on the third probability; and determining a first risk of infection of a first user associated with the first wireless device based on the measure of proximity.

* * * * *